(12) United States Patent
Loh et al.

(10) Patent No.: US 8,227,645 B2
(45) Date of Patent: Jul. 24, 2012

(54) CYCLISATION PROCESS OF FORMING A MULTIPLE RING COMPOUND

(75) Inventors: Teck Peng Loh, Singapore (SG); Yu Jun Zhao, Singapore (SG)

(73) Assignee: Nanyang Technological University, Singapore (SG)

( * ) Notice: Subject to any disclaimer, the term of this patent is extended or adjusted under 35 U.S.C. 154(b) by 690 days.

(21) Appl. No.: 12/280,158

(22) PCT Filed: Feb. 22, 2007

(86) PCT No.: PCT/SG2007/000055
§ 371 (c)(1),
(2), (4) Date: Aug. 20, 2008

(87) PCT Pub. No.: WO2007/097719
PCT Pub. Date: Aug. 30, 2007

(65) Prior Publication Data
US 2010/0228058 A1    Sep. 9, 2010

Related U.S. Application Data

(60) Provisional application No. 60/775,363, filed on Feb. 22, 2006.

(51) Int. Cl.
*C07C 41/30* (2006.01)
(52) U.S. Cl. .......... 568/633; 568/659; 568/660
(58) Field of Classification Search ............ None
See application file for complete search history.

(56) References Cited

U.S. PATENT DOCUMENTS

2005/0261513 A1    11/2005    Womack

OTHER PUBLICATIONS

Nakamura et al., Enantioselective Biomimetic Cyclization of Isoprenoids Using Lewis Acid-Assisted Chiral Bronsted Acids: Abnormal Claisen Rearrangements and Successive Cyclizations, J. Am. Chem. Soc. Aug. 2000, vol. 122, pp. 8131-8140.*
Abad et al., Conversion of Dehydroabietic Acid into 20-Keto-C-aryl-18-norsteroids. Formation of the D Ring, J. Org. Chem. 53:3761-3765 (1988).
Allenmark, S.G., Chiroptical methods in the stereochemical analysis of natural products, Nat. Prod. Rep. 17:145-155 (2000).
Brannon et al., Hydroxylation of Some Dehydroabietanes with *Corticium sasakii*, J. Org. Chem. 33(12): 4462-4466 (1968).
Burnell et al., Approaches to the Synthesis of Aromatic Diterpenes Oxygenated in Ring A: Synthesis of Margocilin O-Methyl Ether, J. Nat. Prod. 56(4): 461-472 (1993).
Chang et al., Production of isoprenoid pharmaceuticals by engineered microbes, Nature Chemical Biology 2(12): 674-681 (2006).
Harper et al., Stereochemical Analysis by Solid-State NMR: Structural Predictions in Ambuic Acid, J. Org. Chem. 68(12):4609-4614 (2003).
Jakupovic et al., Malabaricane Derivatives from *Pyrethrum santolinoides*, Phytochemistry 26(5): 1536-1538 (1987).
Johnson et al., Stereospecific Tricyclization of a Polyolefinic Acetal, J. Am. Chem. Soc. 88:3861-3862 (1966).
Johnson, W.S., Nonenzymic Biogenetic-like Olefinic Cyclizations, Accounts of Chemical Research, 1(1):1-7 (1968).
Johnson, W. S., Biomimetic Polyene Cyclizations, Angew. Chem., Int. Ed., 15(1):9-16 (1976).
Kurihara, M. and Hakamata, W., Convenient Preparation of Cyclic Acetals, Using Diols, TMS-source, and a Catalytic Amount of TMSOTf, J. Org. Chem. 68:3413-3415 (2003).
Ravi, B.N. and Wells, R.J., Malabaricane Triterpenes from a Fijian Collection of the Sponge *Jaspis stellifera*, J. Org. Chem. 46:1998-2001 (1981).
Riccio et al, Stereochemical analysis of natural products. Approaches relying on the combination of NMR spectroscopy and computational methods, Pure Appl. Chem. 75(2-3): 295-308 (2003).

(Continued)

*Primary Examiner* — Rosalynd Keys
(74) *Attorney, Agent, or Firm* — Seed IP Law Group PLLC

(57) ABSTRACT

The present invention relates to a cyclization process of forming a multiple ring compound from an isoprenoid compound. The cyclization process involves reacting the isoprenoid compound with an acetal initiator under conditions sufficient to form the multiple ring compound. The isoprenoid compound is contacted with an initiator an optionally with a catalyst. Cyclization occurs by reaction of the initiator with the isoprenoid compound. Cyclic acetal compounds wherein the acetal forms part of 6-membered unsaturated ring are also defined.

34 Claims, 24 Drawing Sheets

(1)

(2)    (3)

OTHER PUBLICATIONS

Rosales et al., Regioselective Palladium-Catalyzed Alkylation of Allylic Halides with Benzylic Grignard Reagents. Two-Step Synthesis of Abietane Terpenes and Tetracyclic Polyprenoid Compounds, J. Org. Chem. 67:1167-1170 (2002).

Sontag et al., Chromogenic Triterpenoids from *Cortinarius fulvoincarnatus, C. sodagnitus* and Related Toadstools (Agaricales), Eur. J. Org.Chem. 255-260 (1999).

Tsunoda, T., Suzuki, M. and Noyori, R., A Facile Procedure for Acetalization Under Aprotic Conditions, Tetrahedron Letters, 21:1357-1358 (1980).

Ulubelen, A. & Miski, M., A New Diterpene Acid from *Salvia tomentosa*, J. Nat. Prod. 44:119-124 (1981).

Ziegler et al., New Dammarane and Malabaricane Triterpenes from *Caloncoba echinata*, J. Nat. Prod. 65:1764-1768 (2002).

International Search Report for PCT Patent Application No. PCT/SG2007/000055, Apr. 2007.

Nakamura et al., Lewis acid-activated chiral leaving group: Enantioselective electrophilic addition to prochiral olefins. J. Org. Chem. 67(15): 5124-5137, 2002.

Zhao et al., Lewis acid-promoted intermolecular acetal-initiated cationic polyene cyclizations. Journal of the American Chemical Society, 129(3): 492-493, 2007.

Fukuzawa et al., Direct synthesis of chiral acetals from carbonyl compounds and chiral diols: Sequential one-pot asymmetric silylcyanation reaction catalysed by scandium (III) triflate. Synlett, 10:1077-1078, 1995.

Kurihara et al., Convenient preparation of cyclic acetals, using diols, TMS-Source, and a catalytic amount of TMSOTf. Journal of Organic Chemistry, 68(9): 3413-3415, 2003.

Chemical Abstracts Online Accession No. 121:8252 Ishihara et al, Highly diastereoselective acetal cleavages using novel reagents prepared from organoaluminium and pentafluorophenol. Journal of the American Chemical Society, 115(23): 10695-10704, 1993.

Chemical Abstracts Online Accession No. 114:197004 JP 02-289541, Dainippon Ink and Chemicals, Inc., Nov. 29, 1990.

Chemical Abstracts Online Accession No. 112:235239 Kaino et al., Chiral aryl Grignard reagents-generation and reactions with carbonyl compounds. Bulletin of the Chemical Society of Japan, 62(11): 3736-3738, 1989.

Chemical Abstracts Online Accession No. 102:61960 Lindell et al., Asymmetric synthesis via chiral acetal templates. 8. Reactions with organometalllic reagents. Tetrahedron Letters, 25(36): 3947-3950, 1984.

Chemical Abstracts Online Accession No. 91:141269 Schacht et al., Synthesis and characterization of 2,6-dichlorobenzaldehyde-generating polymers. In Polym. Drugs (Proc. Int. Symp.), 1978 Meeting Date 1977, New York: Academic Press: p. 331-347.

Snider et al., Lewis acid induced asymmetric prins reactions of chiral acetals with alkenes. Synthetic Communications, 16(12): 4151-4160, 1986.

Isihara et al., Enantio-and diastereoselective stepwise cyclization of polyprenoids induced by chiral and achiral LBAs. A new entry to (−)-Ambrox, (+)-Podocarpa-8,11,13-triene ditepenoids, and(−)-Tetracyclic polyprenoid of sedimentary origin. Journal of the American Chemical Society, 124:3647-3655, 2002.

* cited by examiner

Fig. 1A
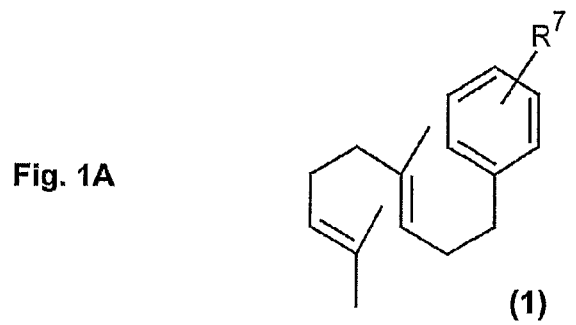
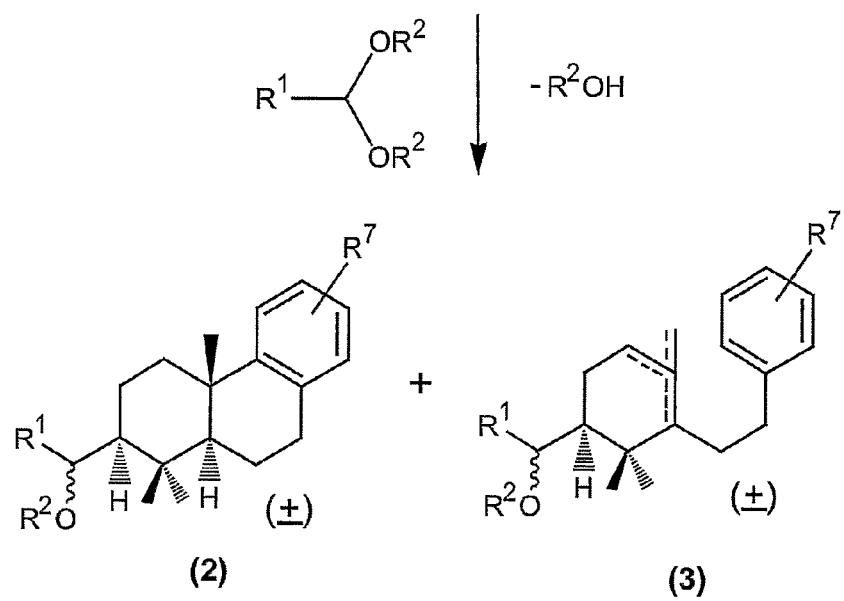
Fig. 1B ($R^7$ = H)
| Entry | Initiator | Product | Yield [%] ($2^a+3$)$^b$ | Ratio: $(2:3)^c$ |
|---|---|---|---|---|
| 1 | PhCH(OMe)$_2$ | 2a | 87 | 88:12 |
| 2 | PhCH(OEt)$_2$ | 2b | 90 | 86:14 |
| 3 | PhCH(OAllyl)$_2$ | 2c | 84 | 97:03 |
| 4 | PhCH(O$i$Pr)$_2$ | 2d | 94 | 84:16 |
| 5 | Ph-[dioxolane] | 2e | 72 | >99:01 |
| 6 | Ph-[dioxane] | 2f | 76 | >99:01 |

| Entry | Initiator | Product | Time/h | Yield/% | d.r. |
|---|---|---|---|---|---|
| 1 | Ph— | 4a | 0.5 | 74 | 88:12 |
| 2 | Br—C6H4— | 4b | 0.5 | 87 | 87:13 |
| 3 | Ph(CH2)2— | 4c | 0.5 | 71 | 81:19 |
| 4 | C7— | 4d | 0.5 | 74 | 85:15 |
| 5 | allyl-(CH2)2— | 4e | 0.5 | 62 | 88:12 |
| 6 | St— | 4f | 24 | 80 | 87:11:02 |

Fig. 3: Terminating Alcohol Moiety
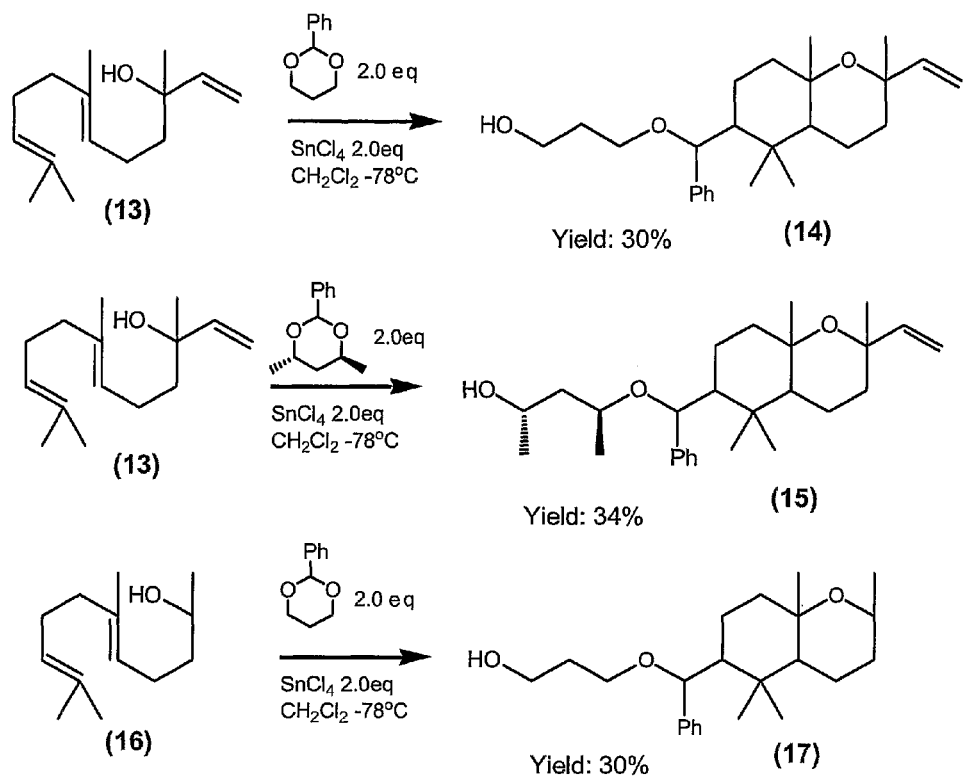
Fig. 4: Terminating Alkene Moiety
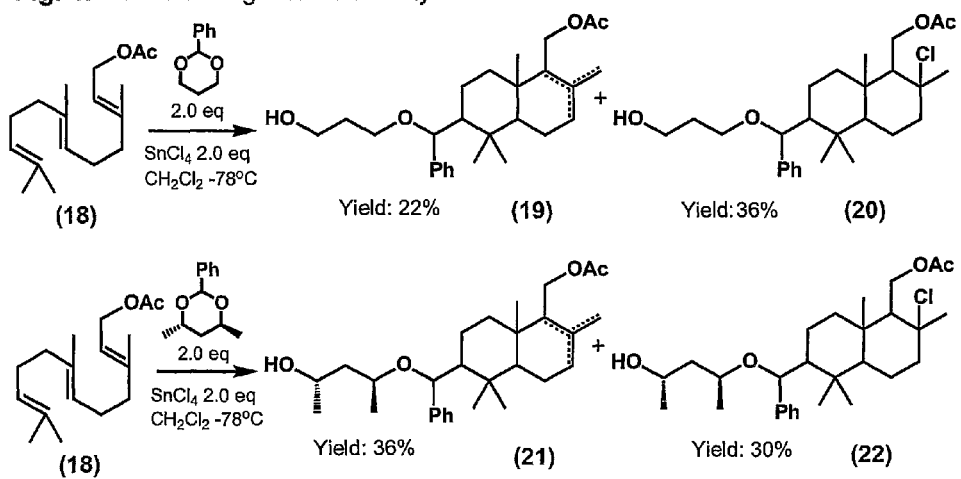

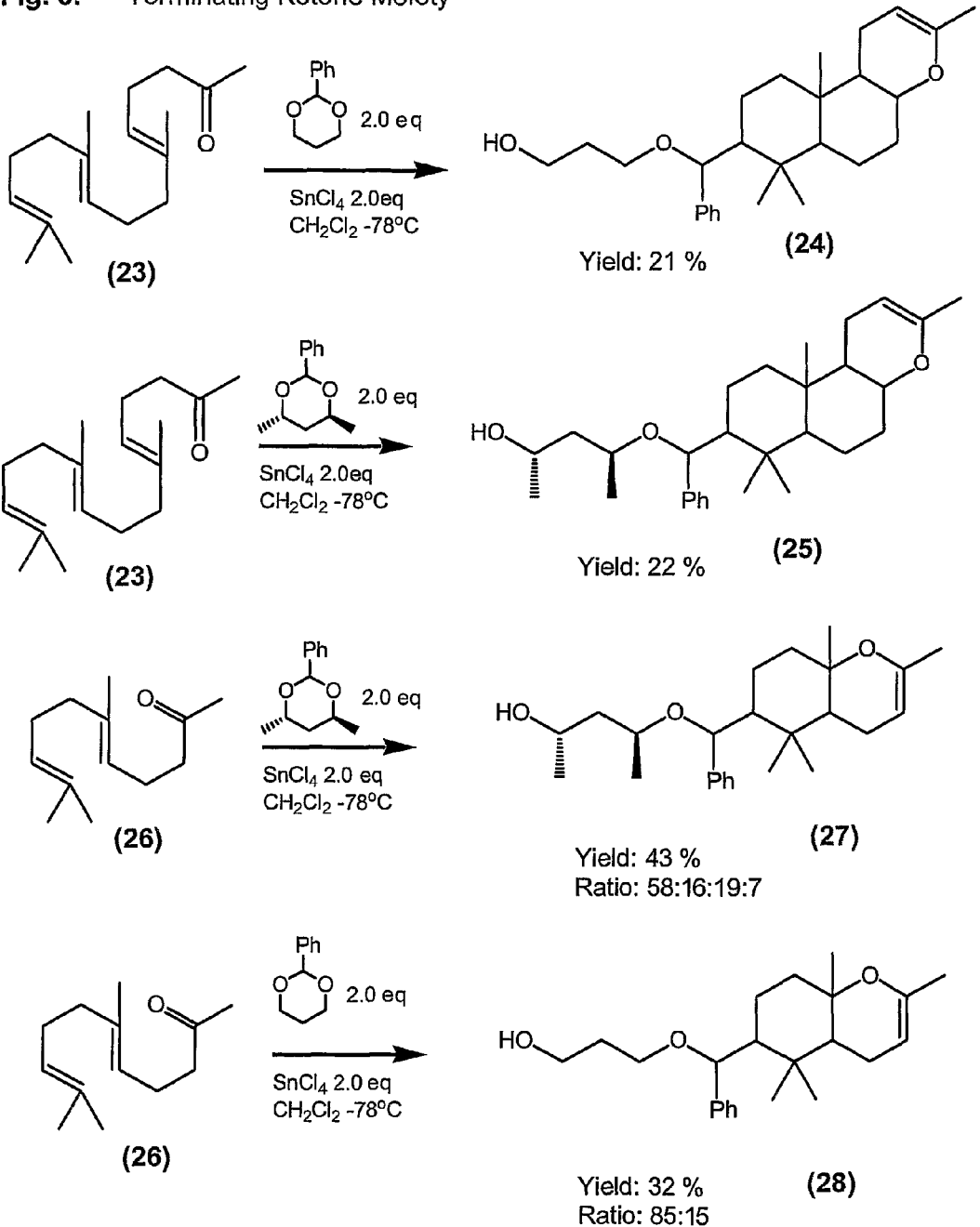
Fig. 5: Terminating Ketone Moiety

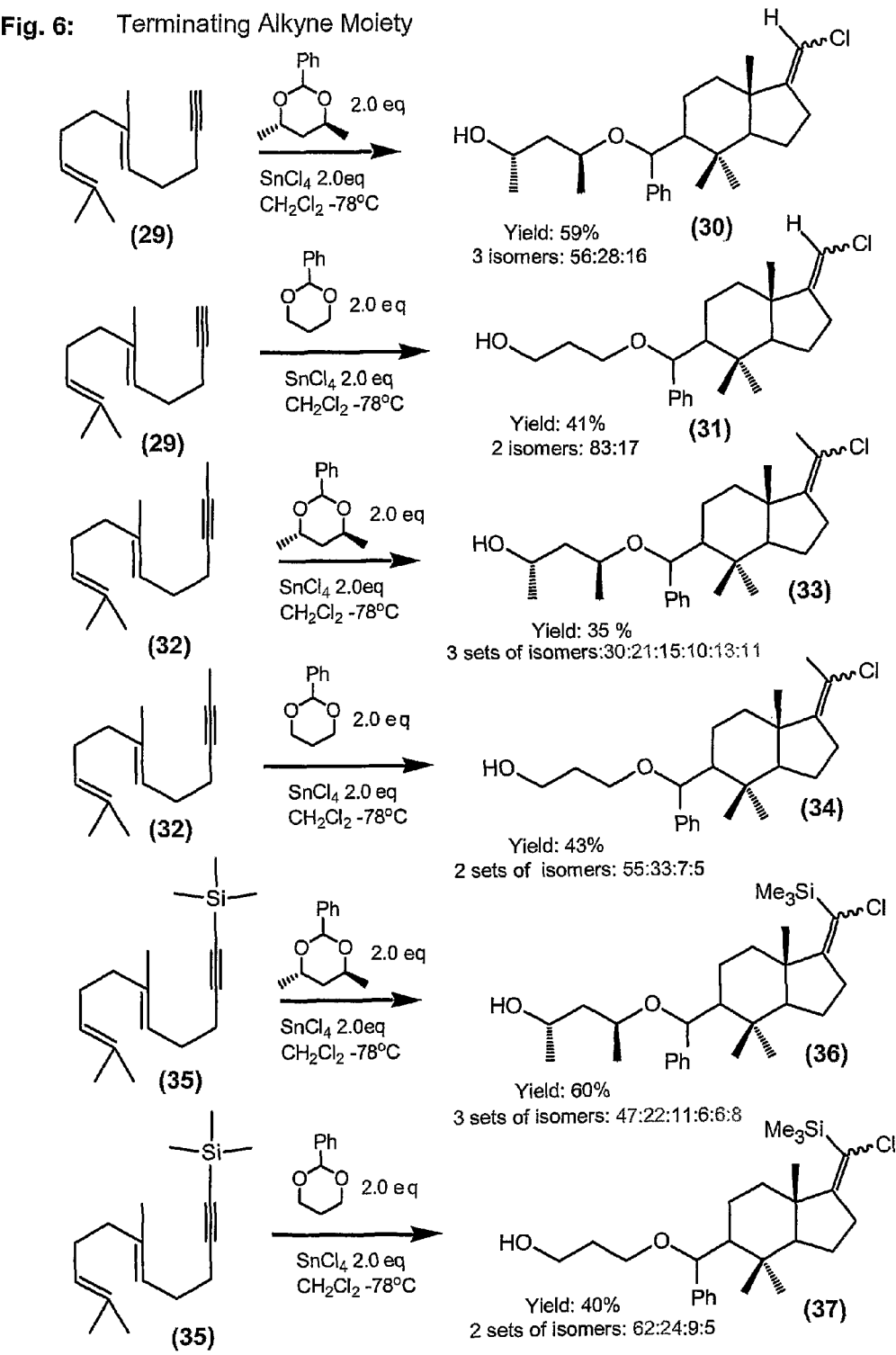
Fig. 6: Terminating Alkyne Moiety

Fig. 6: Terminating Alkyne Moiety (continued)
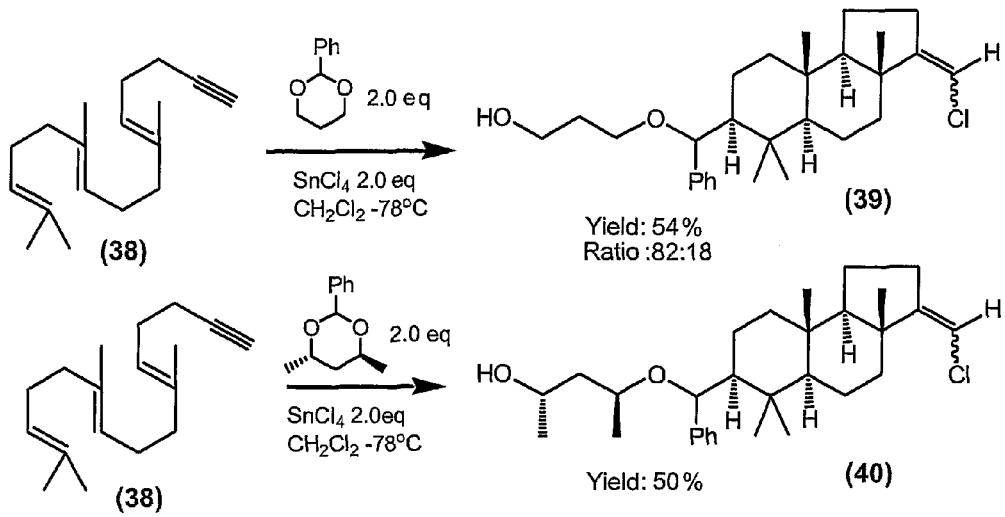
Fig. 7
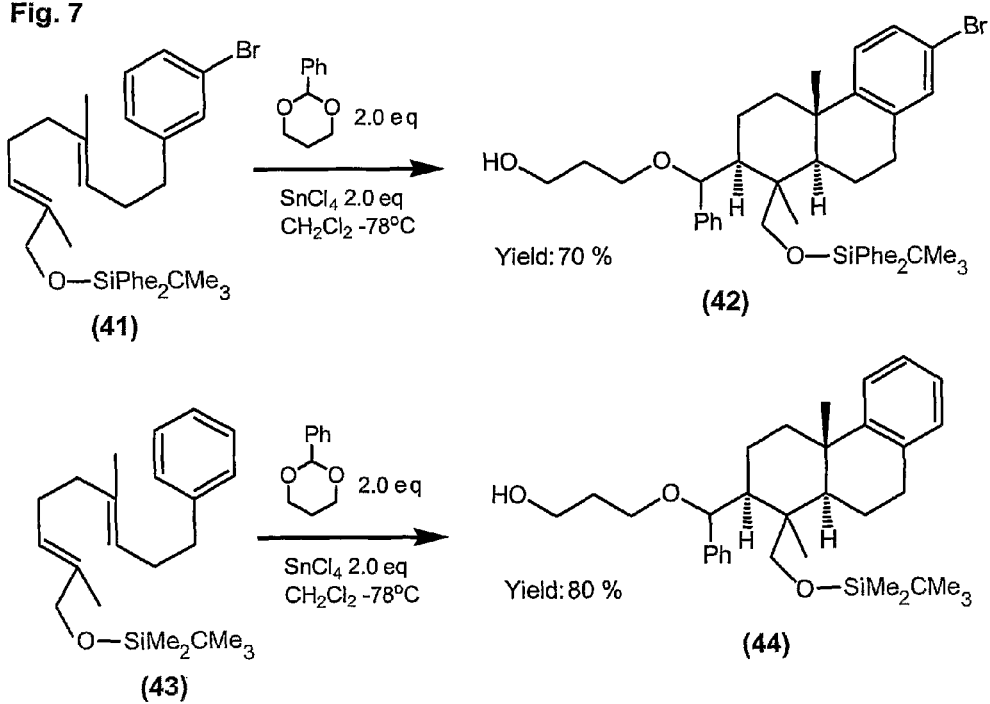

| Entry | R⁷ | Product | Yield [%] | d.r. |
|---|---|---|---|---|
| 1 | — | 6a | 73 | 66:18:10:6 |
| 2 | 4-Me | 6b | 66 | 66:17:14:3 |
| 3 | 3-Me | 6c | 75 | 73:14:12:1 |
| 4 | 2-Me | 6d | 76 | 71:20:8:1 |
| 5 | 4-OMe | 6e | 59 | 74:18:7:1 |
| 6 | 4-$i$Pr | 6f | 71 | 64:20:14:2 |

| Entry | chiral Initiator | Product | Yield [%] ($2^a$+3)$^b$ | Ratio: (2/2':3)$^c$ | dr$^c$ (2:2') |
|---|---|---|---|---|---|
| 1 | PhCH(O-CHMe-)$_2$ (±) | 2g/2g' | 88 | >99:1 | 61:39 |
| 2 | PhCH(O-C(CO$_2$Me)Me-)$_2$ | 2h/2h' | 80 | 69:31 | 88:12 |

| Entry | R[7] | Product | Initiator | Yield [%] (2+2'+2")[a,b] | Ratio[c] (2:2':2") | d.r.[d] (2+2":2') |
|---|---|---|---|---|---|---|
| 1[e] | — | 2i/i'/i" | (10) | 58 | 76:8:13:3 | 89:11 |
| 2 | — | 2j/j'/j" | (9) | 89 | 66:18:16 | 82:18 |
| 3 | 4-iPr | 2k/k'/k" | (9) | 88 | 73:14:13 | 86:14 |
| 4 | 4-OMe | 2l/l'/l" | (9) | 75 | 72:16:12 | 84:16 |
| 5[f] | 3-OMe | 2m/m'/m" | (9) | 65 | 66:19:15 | 81:19 |
| 6 | 4-Me | 2n/n'/n" | (9) | 87 | 66:17:17 | 83:17 |
| 7 | 3-Me | 2o/o'/o" | (9) | 85 | 71:18:11 | 82:18 |

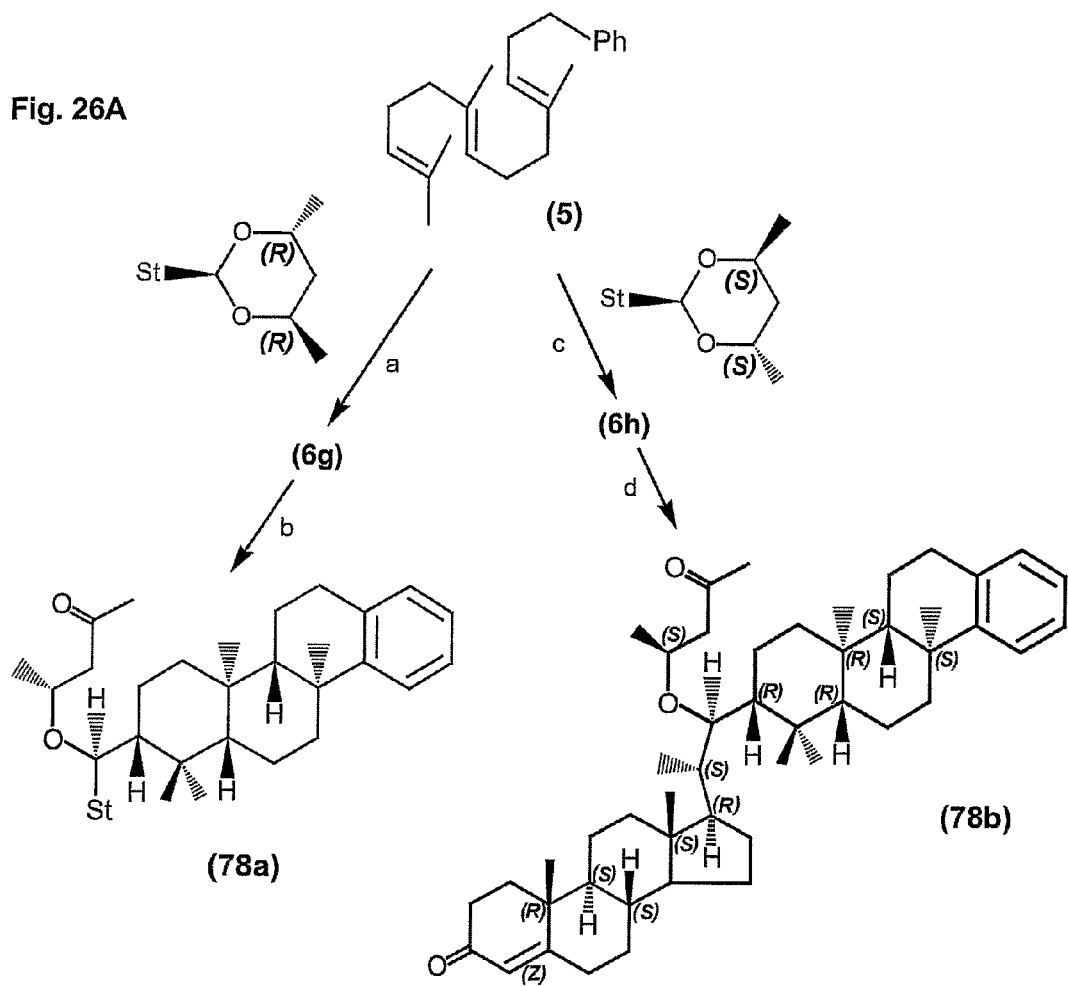
Fig. 26A
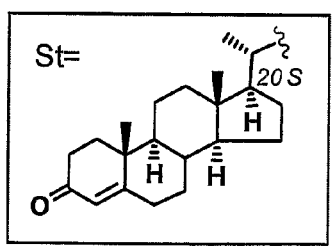
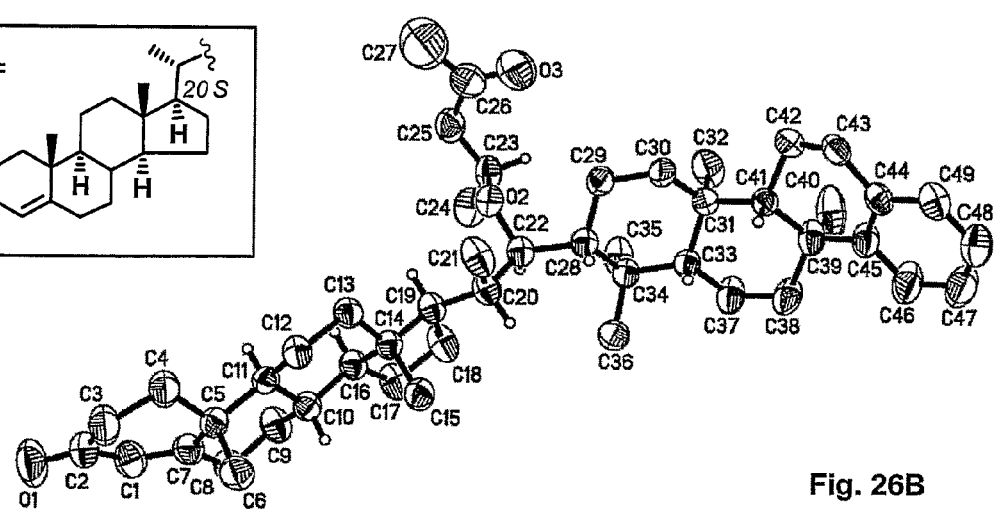
Fig. 26B

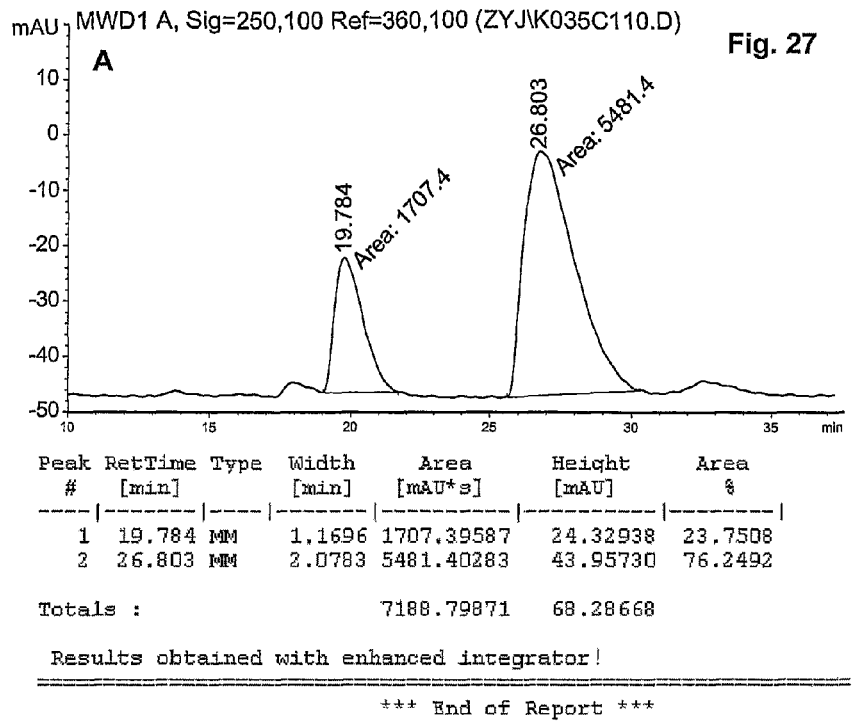
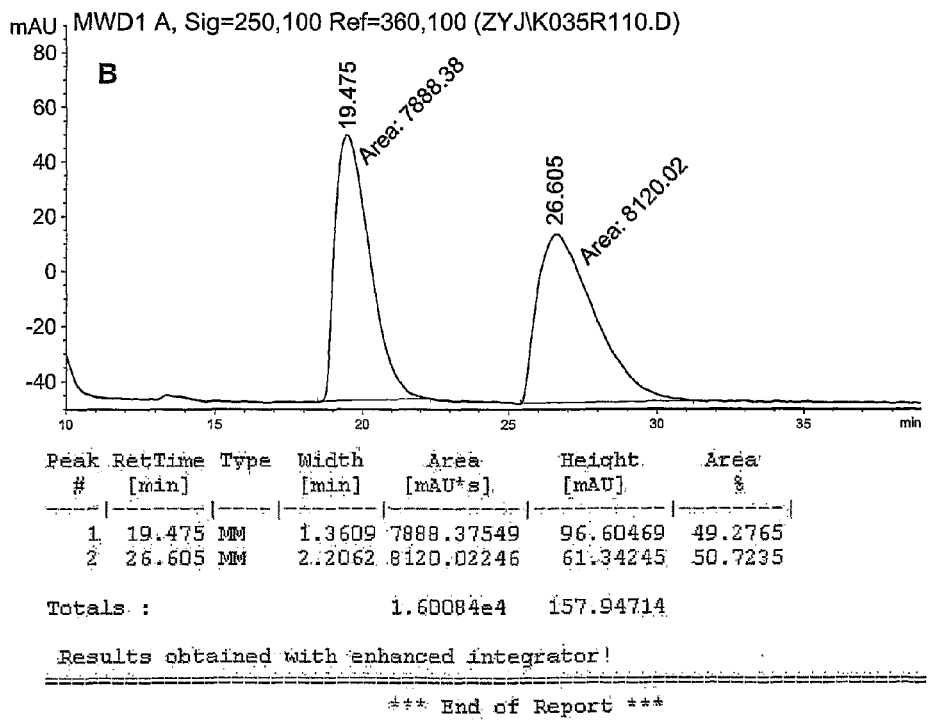
Fig. 27

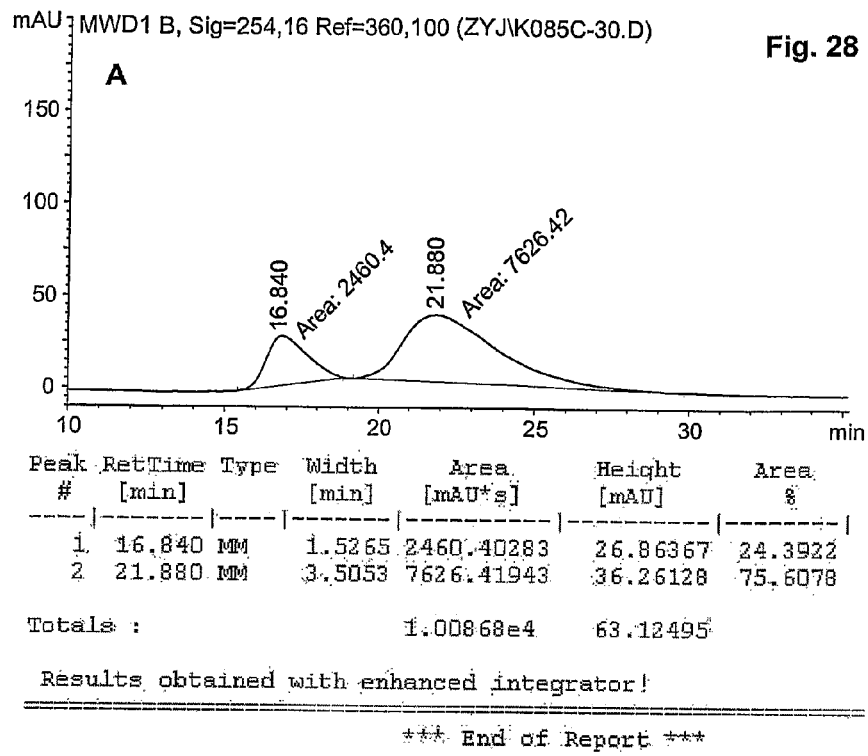
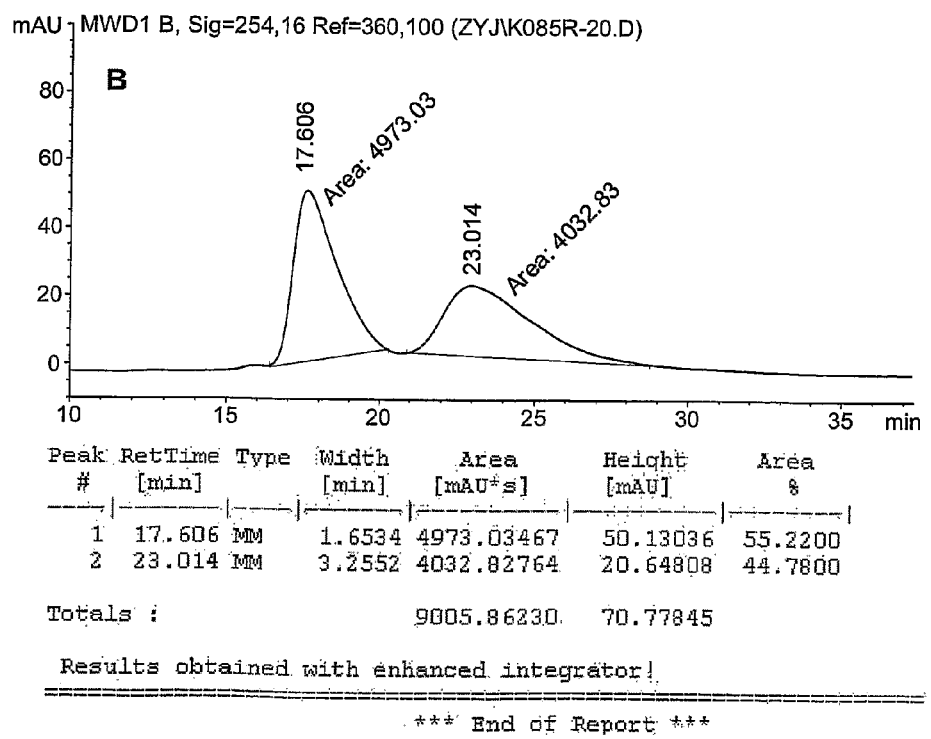
Fig. 28

CYCLISATION PROCESS OF FORMING A MULTIPLE RING COMPOUND

CROSS-REFERENCE TO RELATED APPLICATIONS

The present application claims the benefit of U.S. provisional application 60/775,363 filed Feb. 22, 2006, the contents of which is incorporated herein by reference in its entirety for all purposes.

FIELD OF THE INVENTION

The present invention relates to a cyclisation process of forming a multiple ring compound. The cyclisation process includes reacting an isoprenoid compound with an acetal initiator under conditions sufficient to form the multiple ring compound. Generally the cyclisation process includes contacting an isoprenoid compound with an initiator and the intramolecular cyclisation reaction of the isoprenoid compound.

BACKGROUND OF THE INVENTION

The cyclisation of acyclic isoprenoid compounds is a very powerful and effective cascade reaction because it can construct multiple rings in a single one step reaction. The reaction has therefore been a focus in the construction of polycyclic molecules due to its efficiency of C—C bond formation and stereospecificity. This contributes to increasing product yield, reducing processing time as well as waste production. Processes known in the art use various types of catalysts for the cyclisation reaction. A commonly used type of catalyst are Lewis acids. Using chiral Lewis acids terpene rings could be constructed asymmetrically.

The intramolecular acetal-initiated cationic isoprenoid cyclisation reaction was first introduced by W. S. Johnson (e.g. Johnson, W. S., & Kinnel, R. B., *J. Am. Chem. Soc.* (1966) 88, 3861-3862; Johnson, W. S., *Angew. Chem., Int. Ed.* (1976) 15, 9-16; Johnson, W. S., *Acc. Chem. Res.* (1968) 1, 1-8.). Since then, this method has been extensively developed to afford bicyclic, tricyclic, tetracyclic and even pentacyclic products in respectable to good yields. Asymmetric induction has also been achieved using chiral acetal templates, providing enantiomeric excess of up to 90%. However, there exist some disadvantages in using acetals for intramolecular polyene cyclisations. The need to incorporate the required acetal into the acyclic precursor introduces added synthetic complexity. In addition, the accommodation of the acetal moiety also diminishes the structural flexibility in the acyclic precursor. These two problems can reduce the scope and applicability of the method substantially.

It is therefore an object of the present invention to overcome these problems and to provide a new method of preparing a multiple ring compound.

SUMMARY OF THE INVENTION

The present invention relates to a cyclisation process of preparing a multiple ring compound. The cyclisation process includes reacting an isoprenoid compound with an acetal initiator under conditions sufficient to form the multiple ring compound.

According to some embodiments the cyclisation process includes contacting the isoprenoid compound with the acetal initiator and a catalyst.

According to some embodiments of the cyclisation process reacting the isoprenoid compound with the acetal initiator includes allowing the acetal initiator to form a covalent bond with the isoprenoid compound.

According to some embodiments the cyclisation process is an enantioselective cyclisation.

In a further aspect the present invention provides a cyclic acetal of the general formula

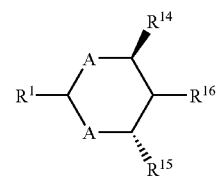

$R^1$, $R^{14}$, $R^{15}$ and $R^{16}$ are independently selected from the group consisting of aliphatic, cycloaliphatic, aromatic, arylaliphatic, and arylcycloaliphatic groups. $R^{16}$ may also be H. $R^1$, $R^{14}$, $R^{15}$ and $R^{16}$ include 0 to about 3 heteroatoms selected from the group N, O, S, Se and Si. A is selected from the group consisting of O, S and Se.

Other aspects and features of the invention will become apparent from the following description of specific embodiments of the invention in conjunction with the accompanying figures.

BRIEF DESCRIPTION OF THE FIGURES

The invention will be better understood with reference to the detailed description when considered in conjunction with the non-limiting examples and the accompanying drawings.

FIG. 1A shows an exemplary scheme of a cyclisation process of preparing a multiple ring compound. FIG. 1B shows a table summarising the obtained products using various acetals.

FIG. 3 shows exemplary reactions of a cyclisation process of preparing a multiple ring compound using an isoprenoid compound that includes an OH-group in its terminating moiety.

FIG. 4 shows exemplary reactions of a cyclisation process of preparing a multiple ring compound using an isoprenoid compound that includes a C═C double bond in its terminating moiety.

FIG. 5 shows exemplary reactions of a cyclisation process of preparing a multiple ring compound using an isoprenoid compound that includes a keto group in its terminating moiety.

FIG. 6 shows exemplary reactions of a cyclisation process of preparing a multiple ring compound using an isoprenoid compound that includes a C≡C triple bond in its terminating moiety.

FIG. 7 shows exemplary reactions of a cyclisation process of (E)-9-(3-bromophenyl)-2,6-dimethyl-2,6-nonadienyl]-1-oxy-(tert.-butyl)diphenyl-silane (41) and (E)-9-phenyl-2,6-dimethyl-2,6-nonadienyl]-1-oxy-(tert.-butyl)dimethyl-silane (43).

FIG. 26A shows the asymmetric induction depicted in FIG. 25A for isoprenoid compound (5). The same dominance of chiral centers in the acetal initiator in terms of stereochemistry was observed. FIG. 26B shows a representation structure of compound (78b) as obtained by X-ray crystallography.

FIG. 27 depicts the chiral HPLC profile of compound (73) as obtained using the method of the invention (FIG. 27B) in comparison to racemic compound (73) (FIG. 27A, ratio: 50:50) as a reference.

FIG. 28 depicts the chiral HPLC profile of compound (76) as obtained using the method of the invention (FIG. 28B) in comparison to racemic compound (76) (FIG. 28A, ratio: 50:50) as a reference.

DETAILED DESCRIPTION OF THE INVENTION

Figures 2A, 2B:
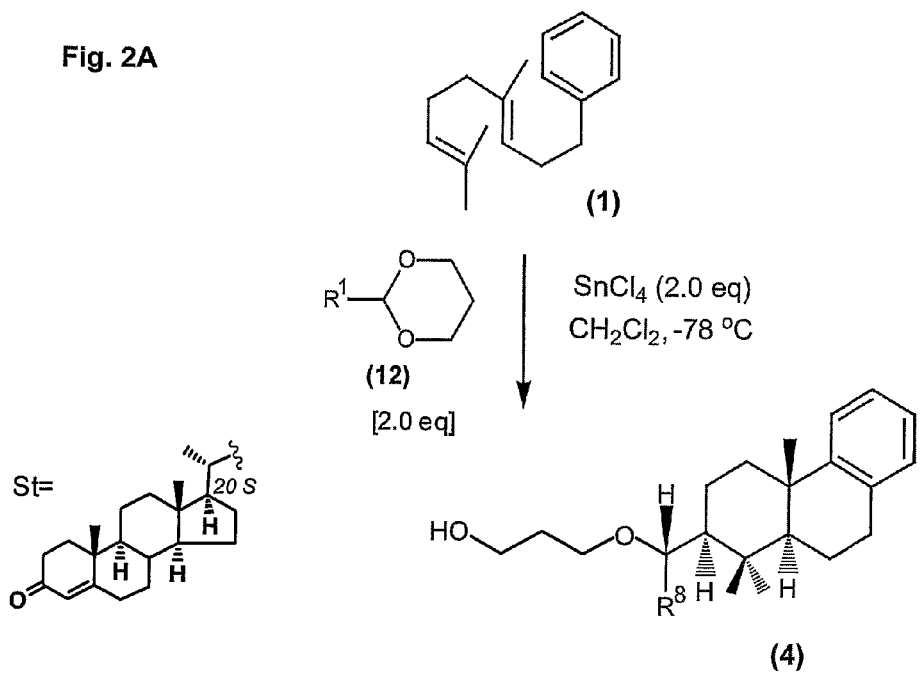
FIG. 2A shows a further exemplary scheme of a cyclisation process of preparing a multiple ring compound.
FIG. 2B shows a table summarising the obtained yields using various moieties $R^1$ of the acetal initiator (12).

The present invention relates to a cyclisation process of forming a multiple ring compound by reaction of a isoprenoid compound. The obtainable product may for instance have a bicyclic, a tricyclic, a tetracyclic, or a pentacyclic ring system. The resulting compound may, for example, be a cyclic terpenoid compound with more than two annulated rings. The invention is based on the surprising finding that an intramolecular cyclisation reaction of an isoprenoid compound can be initiated by means of an intermolecular reaction with an acetal-initiator. Accordingly the cyclisation process according to the present invention includes reacting an isoprenoid compound with an acetal initiator under conditions sufficient to form the multiple ring compound.

The term "isoprenoid" is derived from the name of the unsaturated branched hydrocarbon isoprene 2-methyl-1,3-butadiene. An isoprenoid compound includes so called 'isoprene units' derived from isoprene:

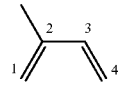

The integers indicate the numbering of the carbon atoms of isoprene. The same numbering will in the following also be used to address carbon atoms of an isoprene unit of an isoprenoid compound used in the method of the present invention, where required. The term "isoprenoid compound" as used herein refers to any compound that includes at least one isoprene unit, or at least two isoprene units. Within the isoprenoid compound at least one isoprene unit (as depicted above)—if present, typically at least two isoprene units—are acyclic moieties. Such an acyclic isoprene unit typically includes one double bond as follows:

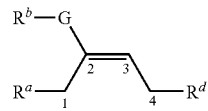

with G being C, Si, O, N, P, S, Se, or a halogen atom. $R^a$, $R^b$ and $R^d$ are independently selected from the group consisting of H, aliphatic, cycloaliphatic, aromatic, arylaliphatic, and arylcycloaliphatic groups (e.g. hydrocarbyl groups). A respective aliphatic, cycloaliphatic, aromatic, arylaliphatic or arylcycloaliphatic group is typically of a main chain length of 1 to about 10, to about 15 or to about 20 carbon atoms. Each of $R^a$ to $R^d$ may for example include 0 to about 3 heteroatoms (i.e. atoms that differ from carbon) selected from the group N, O, S, Se and Si. Isoprenoid compounds with such acyclic moieties are particularly suitable for the method of the present invention.

In this regard the term "isoprenoid unit" as used herein also includes moieties in which the methylene group that is bond to carbon atom No. 2 of isoprene (see above), is replaced by another atom such as Si, O, N, S, Se, a halogen atom or P, or in which the respective side chain of isoprene includes a heteroatom. This fact is indicated by the moiety G in above representation of an isoprenoid unit. In embodiments where moiety G is a methylene group (i.e. unsubstituted carbon, —CH$_2$—), an isoprenoid unit may be depicted as:

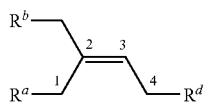

with $R^a$, $R^b$ and $R^d$ as defined above. As also explained below, the term "isoprenoid unit" refers to any configuration and/or conformation of bonds or centers of the respective unit, alone or when viewed within the entire isoprenoid compound used in the method of the invention.

Where a plurality of isoprene units is present within a respective isoprenoid compound, they may be directly connected to each other or separated by further moieties. In typical embodiments of the method of the invention, the isoprene units of the isoprenoid compound are directly connected to each other. As a few illustrative examples, an isoprenoid compound may include a structure as represented by one of the four following general formulas (VIa), (VIb), (VIc) and (VId):

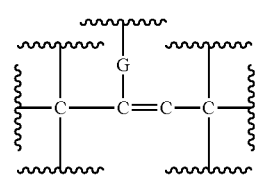
(VIa)

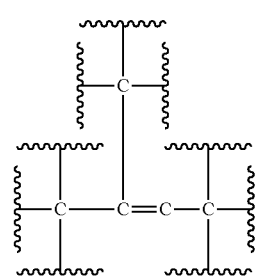
(VIb)

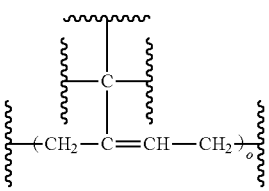
(VIc)

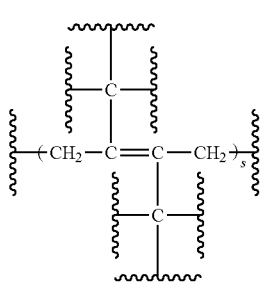
(VId)

wherein o and s in formulas (VIc) and (VId), respectively, are an integer from 1 to about 6, such as for example 2, 3, 4 or 5.

G in formula (VIa) may be, as indicated above, C, Si, O, N, P, S, Se, or a halogen atom. Where applicable, the respective double bond of an isoprenoid compound may be of the E-(trans-) or the Z-(cis-) configuration. The isoprenoid compound may carry various substituents. As an illustrative example, an isoprenoid compound of two isoprenoid units may include a structure as represented by the following general formulas (VIe) and (VIf):

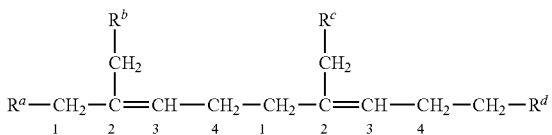
(VIe)

in which the numberings of the carbon atoms of each isoprenoid unit (cf. above) are indicated in italic letters below the respective carbon atoms of the isoprenoid compound, and:

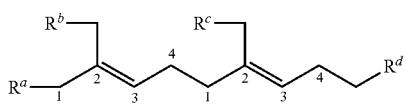
(VIf)

wherein $R^a$ to $R^d$ in formulas (VIe) and (VIf) may be H, an aliphatic, cycloaliphatic, aromatic, arylaliphatic, or arylcycloaliphatic group (e.g. a hydrocarbyl group) or a functional group. Each of $R^a$ to $R^d$ may for example include 0 to about 3 heteroatoms (i.e. atoms that differ from carbon) selected from the group N, O, S, Se and Si. A respective functional group may be a halogen, hydroxyl-, thiol-, seleno-, carboxyl-, amino-, imino-, amido-, imido-, azido-, diazo-, cyano-, isocyano-, nitro-, nitroso-, sulfo-, sulfido-, sulfonyl-, or silyl- group. If any one or more of $R^a$ to $R^d$ are an aliphatic, cycloaliphatic, aromatic, arylaliphatic, or arylcycloaliphatic moiety, it/they may also include other polar, non-polar, saturated or unsaturated groups, including for example an epoxy group or 0 to about 3 heteroatoms selected from the group N, O, S, Se and Si.

In some embodiments the isoprenoid compound may be of the general formula (VIg):

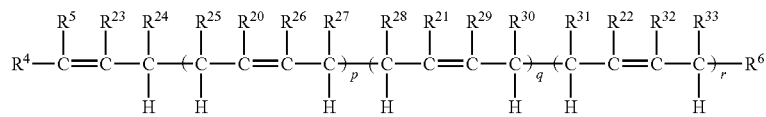

$R^4$ and $R^5$ are an independently selected aliphatic, cycloaliphatic, aromatic, arylaliphatic, or arylcycloaliphatic moiety (see also below). $R^{20}$ to $R^{33}$ are an independently selected aliphatic, cycloaliphatic, aromatic, arylaliphatic, or arylcycloaliphatic moiety, halogen, a hydroxyl-group, a thiol-group, a seleno-group, a carboxyl-group, an amino-group, an imino-group, an amido-group, an imido-group, an azido-group, a diazo-group, a cyano-group, an isocyano-group, a nitro-group, a nitroso-group, a sulfo-group group, a sulfido-group, a sulfonyl-group or a silyl-group. A respective aliphatic, cycloaliphatic, aromatic, arylaliphatic or arylcycloaliphatic group is typically of a main chain length of 1 to about 10, to about 15 or to about 20 carbon atoms. Each of $R^4$, $R^5$ and $R^{20}$ to $R^{33}$ may for example include 0 to about 3, such as one or two, heteroatoms selected from the group N, O, S, Se and Si. P, q and r are an independently selected integer between 0 and about 4. $R^6$ is a terminating moiety, which may be H, an aliphatic, cycloaliphatic, aromatic, arylaliphatic, or arylcycloaliphatic moiety (e.g. a hydrocarbyl group), typically with a main chain of a length of 1 to about 10, to about 15 or to about 20 carbon atoms, or a functional group (see also below).

In some embodiments the isoprenoid compound may be of the general formula (VI):

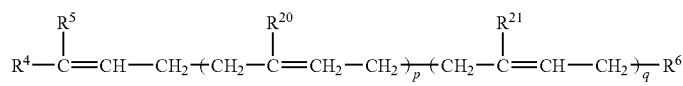

As defined above, $R^{20}$ and $R^{21}$ are an independently selected aliphatic, cycloaliphatic, aromatic, arylaliphatic, or arylcycloaliphatic moiety, halogen, a hydroxyl-group, a thiol-group, a seleno-group, a dithiane group, a carbonyl-group, a carboxyl-group, an amino-group, an imino-group, an amido-group, an imido-group, an azido-group, a diazo-group, a cyano-group, a thiocyano-group, an isocyano-group, a nitro-group, a nitroso-group, a sulfo-group group, a sulfido-group, a sulfonyl-group, a silyl- or a siloxy-group. $R^4$ and $R^5$ are an independently selected aliphatic, cycloaliphatic, aromatic, arylaliphatic, or arylcycloaliphatic moiety (see also below). A respective aliphatic, cycloaliphatic, aromatic, arylaliphatic or arylcycloaliphatic group (of $R^4$, $R^5$, $R^{20}$ and $R^{21}$) is typically of a main chain length of 1 to about 10, to about 15 or to about 20 carbon atoms. Each of $R^4$, $R^5$, $R^{20}$ and $R^{21}$ may for example include 0 to about 3 heteroatoms selected from the group N, O, S, Se and Si. P and q are an independently selected integer between 0 and about 4. $R^6$ is a terminating moiety (see below for examples).

In some embodiments the isoprenoid compound may be of the general formula (VII):

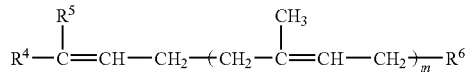

wherein m is an integer between 1 and about 5, such as for example 2, 3 or 4. $R^4$ and $R^5$ are independently selected aliphatic, cycloaliphatic, aromatic, arylaliphatic, or arylcycloaliphatic moieties (e.g. a hydrocarbyl group), typically with a main chain of a length of 1 to about 20 carbon atoms. $R^4$ and $R^5$ may also include other polar, non-polar, saturated or unsaturated groups. $R^4$ and $R^5$ may for example include 0 to about 3 heteroatoms (i.e. atoms that differ from carbon) selected from the group N, O, S, Se and Si. $R^6$ is a terminating moiety, which may be H, an aliphatic, cycloaliphatic, aromatic, arylaliphatic, or arylcycloaliphatic moiety (e.g. a hydrocarbyl group), typically with a main chain of a length of 1 to about 10, to about 15 or to about 20 carbon atoms, or a functional group. A respective functional group may be a halogen, hydroxyl-, thiol-, dithiane-, seleno-, carboxyl-, amino-, imino-, amido-, imido-, carbonyl-, carboxyl-, azido-, diazo-, cyano-, isocyano-, thiocyano-, nitro-, nitroso-, sulfo-, sulfido-, a sulfonyl- (e.g. a trifluoromethyl sulfonyl-p-toluenesulfonyl, bromobenzene-sulfonyl, nitrobenzenesulfonyl-, or a methane-sulfonyl), a silyl-, silano- or siloxy-group. If $R^6$ is an aliphatic, cycloaliphatic, aromatic, arylaliphatic, or arylcycloaliphatic moiety, it may also include other polar, non-polar, saturated or unsaturated groups, including for example an epoxy group or 0 to about 3 heteroatoms selected from the group N, O, S, Se and Si. As defined above, m is an integer between 1 and about 5, such as for example 2.

A respective isoprenoid compound may for example be of the general formula (VIIa):

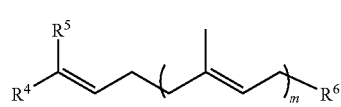

wherein $R^4$ to $R^6$ are defined as above, e.g. for formulas (VIe) and (VII).

The term "aliphatic" means, unless otherwise stated, a straight or branched hydrocarbon chain, which may be saturated or mono- or poly-unsaturated and include heteroatoms (see below). An unsaturated aliphatic group contains one or more double and/or triple bonds (alkenyl or alkinyl moieties). The branches of the hydrocarbon chain may include linear chains as well as non-aromatic cyclic elements. The hydrocarbon chain, which may, unless otherwise stated, be of any length, and contain any number of branches. Typically, the hydrocarbon (main) chain includes 1 to 5, to 10, to 15 or to 20 carbon atoms. Examples of alkenyl radicals are straight-chain or branched hydrocarbon radicals which contain one or more double bonds. Alkenyl radicals normally contain about two to about twenty carbon atoms and one or more, for instance two, double bonds, such as about two to about ten carbon atoms, and one double bond. Alkynyl radicals normally contain about two to about twenty carbon atoms and one or more, for example two, triple bonds, such as two to ten carbon atoms, and one triple bond. Examples of alkynyl radicals are straight-chain or branched hydrocarbon radicals which contain one or more triple bonds. Examples of alkyl groups are methyl, ethyl, propyl, butyl, pentyl, hexyl, heptyl, octyl, nonyl, decyl, the n isomers of these radicals, isopropyl, isobutyl, isopentyl, sec-butyl, tert-butyl, neopentyl, 3,3-dimethylbutyl. Both the main chain as well as the branches may furthermore contain heteroatoms as for instance N, O, S, Se or Si or carbon atoms may be replaced by these heteroatoms.

The term "alicyclic" means, unless otherwise stated, a non-aromatic cyclic moiety (e.g. hydrocarbon moiety), which may be saturated or mono- or poly-unsaturated. The cyclic hydrocarbon moiety may also include fused cyclic ring systems such as decalin and may also be substituted with non-aromatic cyclic as well as chain elements. The main chain of the cyclic hydrocarbon moiety may, unless otherwise stated, be of any length and contain any number of non-aromatic cyclic and chain elements. Typically, the hydrocarbon (main) chain includes 3, 4, 5, 6, 7 or 8 main chain atoms in one cycle. Examples of such moieties include, but are not limited to, cyclopentyl, cyclohexyl, cycloheptyl, or cyclooctyl. Both the cyclic hydrocarbon moiety and, if present, any cyclic and chain substituents may furthermore contain heteroatoms, as for instance N, O, S, Se or Si, or a carbon atom may be replaced by these heteroatoms. The term "alicyclic" also includes cycloalkenyl moieties that are unsaturated cyclic hydrocarbons, which generally contain about three to about eight ring carbon atoms, for example five or six ring carbon atoms. Cycloalkenyl radicals typically have a double bond in the respective ring system. Cycloalkenyl radicals may in turn be substituted.

The term "aromatic" means, unless otherwise stated, a planar cyclic hydrocarbon moiety of conjugated double bonds, which may be a single ring or include multiple fused or covalently linked rings, for example, 2, 3 or 4 fused rings. The term aromatic also includes alkylaryl. Typically, the hydrocarbon (main) chain includes 5, 6, 7 or 8 main chain atoms in one cycle. Examples of such moieties include, but are not limited to, cyclopentadienyl, phenyl, napthalenyl-, [10]annulenyl-(1,3,5,7,9-cyclodecapentaenyl-), [12]annulenyl-, [8]annulenyl-, phenalene (perinaphthene), 1,9-dihydropyrene, chrysene (1,2-benzophenanthrene). An example of an alkylaryl moiety is benzyl. The main chain of the cyclic hydrocarbon moiety may, unless otherwise stated, be of any length and contain any number of heteroatoms, as for instance N, O and S. Examples of such heteroaromatic moeities (which are known to the person skilled in the art) include, but are not limited to, furanyl-, thiophenyl-, naphtyl-, naphthofuranyl-, anthrathiophenyl-, pyridinyl-, pyrrolyl-, quinolinyl, naphthoquinolinyl-, quinoxalinyl-, indolyl-, benzindolyl-, imidazolyl-, oxazolyl-, oxoninyl-, oxepinyl-, benzoxepinyl-, azepinyl-, thiepinyl-, selenepinyl-, thioninyl-, azecinyl-(azacyclodecapentaenyl-), diazecinyl-, azacyclododeca-1,3,5,7,9,11-hexaene-5,9-diyl-, azozinyl-, diazocinyl-, benzazocinyl-, azecinyl-, azaundecinyl-, thia[11]annulenyl-, oxacyclotrideca-2,4,6,8,10,12-hexaenyl- or triazaanthracenyl-moieties.

By the term "arylaliphatic" is meant a hydrocarbon moiety, in which one or more aromatic moieties are substituted with one or more aliphatic groups. Thus the term "arylaliphatic" also includes hydrocarbon moieties, in which two or more aryl groups are connected via one or more aliphatic chain or chains of any length, for instance a methylene group. Typically, the hydrocarbon (main) chain includes 5, 6, 7 or 8 main chain atoms in each ring of the aromatic moiety. Examples of arylaliphatic moieties include, but are not limited to, 1-ethylnaphthalene, 1,1'-methylenebis-benzene, 9-isopropylanthracene, 1,2,3-trimethyl-benzene, 4-phenyl-2-buten-1-ol, 7-chloro-3-(1-methylethyl)-quinoline, 3-heptyl-furan, 6-[2-(2,5-diethylphenyl)ethyl]-4-ethyl-quinazoline or, 7,8-dibutyl-5,6-diethyl-iso-quinoline.

Each of the terms "aliphatic", "alicyclic", "aromatic" and "arylaliphatic" as used herein is meant to include both substituted and unsubstituted forms of the respective moiety. Substituents my be any functional group, as for example, but not limited to, amino, amido, azido, carbonyl, carboxyl, cyano, isocyano, dithiane, halogen, hydroxyl, nitro, organometal, organoboron, seleno, silyl, silano, sulfonyl, thio, thiocyano, trifluoromethyl sulfonyl, p-toluenesulfonyl, bromobenzenesulfonyl, nitrobenzenesulfonyl, and methanesulfonyl.

With regard to the configuration of the double bonds included in the isoprenoid compound, these may exist in Z- and/or E-configurations. In the method of the present invention the isoprenoid compound may include either of these configurations. Regardless of the configuration of double bonds included in the isoprenoid compound, carrying out the process according to the present invention results in a cyclisation and formation of a multiple ring compound. As an illustrative example, where in formula (VIIa) m=2, the following compounds are equally well suited for the purposes of the present invention:

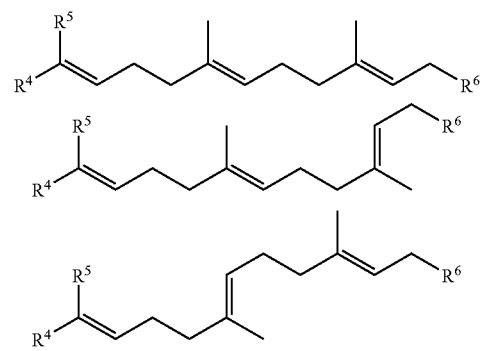

As already indicated above, the term "isoprenoid compound" as used herein, thus refers to all respective isomers of for instance general formulas (VIa) to (VIe) or general formula (VII).

As a further illustrative example, in some embodiments the isoprenoid compound is of the general formula (VIII):

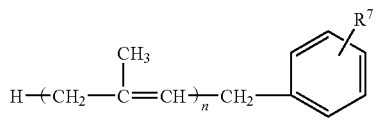

such as for example of general formula (VIIIa):

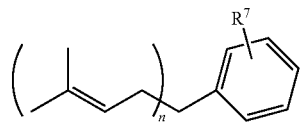

wherein n is an integer between 1 and 3. $R^7$ may be selected from the group consisting of H, aliphatic, cycloaliphatic, aromatic, arylaliphatic, and arylcycloaliphatic groups (e.g. hydrocarbyl groups). $R^7$ is typically of a main chain length of 1 to about 10, about 15 or about 20 carbon atoms, and may include 0 to about 3 heteroatoms selected from the group N, O, S, Se and Si. $R^7$ may also include other polar, non-polar, saturated or unsaturated groups. As an example, where n=1, the isoprenoid compound is an aromatic 4-methyl-3-pentenyl-compound, such as 2-methyl-5-phenyl-2-pentene (Chemical Abstracts No. 33501-90-5), 1-methyl-4-(4-methyl-3-pentenyl)-benzene (Chemical Abstracts No. 51082-27-0), 2-(4-methyl-3-pentenyl)-phenol (CAS-No. 143700-87-2) or p-(4-methyl-3-pentenyl)-anisole (CAS-No. 4586-91-8). As a further example, where n=2, the isoprenoid compound is an aromatic [(3E)-4,8-dimethyl-3,7-nonadienyl]-compound, such as trans-2,6-dimethyl-9-phenyl-2,6-nonadiene (CAS-No. 22555-66-4), 1-[(3E)-4,8-dimethyl-3,7-nonadienyl]-4-methyl-benzene (CAS-No. 405506-88-9), 1-[(3E)-4,8-dimethyl-3,7-nonadienyl]-3-methoxy-benzene (Chemical Abstracts No. 38011-81-3), 1-[(3E)-4,8-dimethyl-3,7-nonadienyl]-4-(1-methylethyl)-benzene (CAS-No 405506-89-0), 1-[(3E)-4,8-dimethyl-3,7-nonadienyl]-3-methyl-benzene (CAS-No 57293-25-1), 2-[(3E)-4,8-dimethyl-3,7-nonadienyl]-5,6-dimethoxy-3-methyl-1,4-benzenediol (CAS-No 216225-99-9), (E)-4-(4,8-dimethyl-3,7-nonadienyl)-1-methoxy-2-methyl-benzene (CAS-No 79243-47-3), (E)-4-(4,8-dimethyl-3,7-nonadienyl)-benzoic acid ethyl ester (CAS-No 50793-34-5), (E)-4-(4,8-dimethyl-3,7-nonadienyl)-1,2-dimethoxy-benzene (CAS-No 106625-40-5), 4-[(3E)-4,8-dimethyl-3,7-nonadienyl]-phenol (CAS-No 331233-75-1), (E)-4-(4,8-dimethyl-3,7-nonadienyl)-benzonitrile (CAS-No 58928-98-61), 4-(4,8-dimethyl-3,7-nonadienyl)-N,N-dimethyl-benzenamine (CAS-No 58928-94-2) or 1-[(3E)-4,8-dimethyl-3,7-nonadien-1-yl]-2-[2-[(2-nitrophenyl)seleno]-ethyl]-benzene (CAS-No 915315-78-5). In embodiments where n=3, the isoprenoid compound is an aromatic (4,8,12-trimethyl-3,7,11-tridecatrienyl)-compound, such as [(3E,7E)-4,8,12-trimethyl-3,7,11-tridecatrienyl]-benzene (CAS-No 405506-90-3), 1-methyl-4-[(3E,7E)-4,8,12-trimethyl-3,7,11-tridecatrienyl]-benzene (CAS-No 405506-91-4), 1,2,3,4-tetramethoxy-5-methyl-6-[(3E,7E)-4,8,12-trimethyl-3,7,11-tridecatrienyl]-benzene (CAS-No 697286-42-3), or 1-methyl-3-[(3E,7E)-4,8,12-trimethyl-3,7,11-tridecatrienyl]-benzene (CAS-No 331233-82-0). $R^3$ may also form an alicyclic or aromatic bridge, such as for example in 1-[(2E)-3,7-dimethyl-2,6-octadienyl]-naphthalene (CAS-No 372510-66-2).

The isoprenoid compound may be synthesized according to any method known in the art. As an illustrative example, a palladium catalysed coupling reaction, for example of an allylhalide and a benzylic Grignard reagent may be employed (see e.g. Rosales, V., et al., *J. Org. Chem.* (2002) 67, 1167-1170). The isoprenoid compound may also be obtained from a synthesis involving the use of a microorganism, including a recombinant microorganism, for example yeast or *E. coli* expressing enzymes of an isoprenoid biosynthesis pathway (see e.g. Chang, M. C. Y., & Keasling, J. D, *Nature Chemical Biology* (2006) 2, 12, 674-681).

A cyclisation reaction according to the present invention may be performed in the presence of a catalyst. In some embodiments the cyclisation reaction is catalysed by an acid. A respective acid may be both a Brønstedt acid or a Lewis acid. Examples of a suitable Brønstedt acid include, but are not limited to, triflic acid, $CF_3SO_3H$, fluorosulfonic acid, $FSO_3H$, methanesulfonic acid, $MeSO_3H$, trichloromethanesulfonic acid, $CCl_3SO_3H$, hydrobromic acid, HBr, hydrochloric acid, HCl, trifluoroacetic acid, $CF_3CO_2H$, and bis-(trifluoromethanesulfonyl)imide, $((CF_3SO_2)_2NH)$.

A Brønstedt acid is a compound that is capable of acting as a proton donor. A Lewis acid is a compound with a vacant orbital, which can thus accept a pair of electrons and form a coordinate covalent bond. In certain embodiments the Lewis acid is an inorganic Lewis acid. A suitable Lewis acid may for example be derived from an element of Group IIIA of the Periodic Table of Elements, titanium, tin, antimony, tantalum, rhenium, iron or zinc. Examples of an inorganic Lewis acid include, but are not limited to, $AgBF_4$, $AlI_3$, $AlF_3$, $AlCl_3$, $AlBr_3$, $Al_2O_3$, $AsCl_3$, $AsI_3$, $AsF_3$, $AsBr_3$, $BF_3$, $BCl_3$, $BBr_3$, $BI_3$, $CaO$, $CoBr_2$, $CoCl_2$, $CoF_2$, $CoI_2$, $Co(NO_3)_2$, $CuCl_2$, $CuF_2$, $CuI_2$, $Cu(NO_3)_2$, $GaF_3$, $GaCl_3$, $GaBr_3$, $GaI_3$, $InF_3$, $InCl_3$, $InBr_3$, $FeCl_3$, $FeBr_3$, $FeI_3$, $FeF_3$, $FeCl_2$, $FeBr_2$, $FeI_2$, $FeF_2$, $LiClO_4$, $NiCl_2$, $MgCl_2$, $MgI_2$, $MgF_2$, $MgBr_2$, $NbCl_5$, $NiBr_2$, $NiCl_2$, $NiF_2$, $NiI_2$, $Ni(NO_3)_2$, $PCl_3$, $ReO_2F_3$, $SbCl_3$, $SbF_5$, $SbI_3$, $SbBr_3$, $SbCl_5$, $SbI_5$, $SbBr_5$, $SnCl_2$, $SnI_2$, $SnF_2$, $SnBr_2$, $SnBr_4$, $SnCl_4$, $SnI_4$, $SnF_4$, $SnBr_4$, $TiF_4$, $TiCl_4$, $TiBr_4$, $TiCl_2$, $TiCl_3$, $TiCl_4$, $TiF_3$, $TiI_4$, $ZnCl_2$, $ZnCl_2$, $ZnI_2$, $ZnF_2$, and $ZnBr_2$. As a few further examples of a suitable Lewis acid may serve $BF_3BCl_3$—$SMe_2$, $BI_3$—$SMe_2$, $BF_3$—$SMe_2$, $BBr_3$—$SMe_2$, $BF_3$—$OEt_2$, $Et_2AlCl$, $EtAlCl_2$, $MgCl_2OEt_2$, $MgI_2$—$OEt_2$, $MgF_2$—$OEt_2$, $MgBr_2$—$OEt_2$, $Et_2AlCl$, $EtAlCl_2$, $Zn(OAc)_2$, $B(C_6F_5)_3$, $Ti(O$—$Pr_i)_4$, or $Zn(OAc)_2$, $(CH_3CO_2)_2Co$, $AgOTf$, $Al(OTf)_3$, $Ce(OTf)_4$, $Cu(OTf)_2$, $Eu(OTf)_3$, $Dy(OTf)_3$, $In(OTf)_3$, $Ho(OTf)_3$, $Er(OTf)_3$, $Lu(OTf)_3$, $Yb(OTf)_3$, $Nd(OTf)_3$, $Gd(OTf)_3$, $Lu(OTf)_3$, $La(OTf)_3$, $Pr(OTf)_3$, $Tm(OTf)_3$, $Sc(OTf)_3$, $Sn(OTf)_2$, $Sn(OTf)_4$, $Sm(OTf)_3$, $Ti(OTf)_4$, $Y(OTf)_3$ and $Zn(OTf)_2$ or cobalt (II) triflate, cobalt (II) tosylate, $(CH_3CO_2)_2Cu$, copper (II) triflate, copper (II) tosylate, $(CH_3CO_2)_2Ni$, nickel (II) triflate, and nickel (II) tosylate. A respective Lewis acid may be used alone or in the form of a complex thereof, such as a complex with a phenol (including an alkoxy phenol), a carbonic acid such as acetic acid, an ether or an ester. For instance, when a solid cyclising agent, such as aluminium chloride, is to be used, it may be desirable to convert the cyclising agent into an aluminium chloride-ether complex soluble in a common solvent when or before contacting the same with an isoprenoid compound. As a further example, it may be desired to use a gaseous Lewis acid, such as boron trifluoride, in the form of a complex compound with e.g. an ether. If desired, for example in order to achieve or improve stereoselectivity (see also below in this regard), a respective Lewis acid may be provided in the form of a complex with a chiral compound, in which for example atoms complexing the Lewis acid are part of a chiral center.

Typically the isoprenoid compound is contacted with the acetal initiator and the catalyst. Contacting of the respective compounds may be carried out simultaneously or stepwise. As an illustrative example, the isoprenoid compound may be provided first and thereafter contacted with the acetal initiator and the catalyst, for instance by first adding the acetal and thereafter the catalyst, or vice versa.

A cyclisation process according to an embodiment of the present invention, in which an isoprenoid compound of the general formula (VId) (see above) is reacted, results in the formation of a multiple ring compound. The multiple ring compound is at least a bicyclic ring system, of which one ring generally is a 2,2-dimethylcyclohexane ring. In embodiments where the isoprenoid compound is of general formula (VII) (see above), the cyclisation process of the present invention can accordingly be depicted by the following general scheme (I):

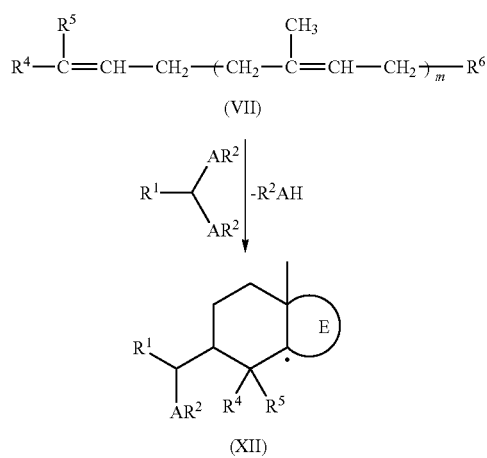

wherein in general formula XII E is an aliphatic, cycloaliphatic or arylaliphatic bridge containing about 3 to about 8 carbon atoms (for example, 5 or 6 carbon atoms), completing a non-aromatic ring that may include 0 up to about 2 heteroatoms. As further explained below, above, A is selected from O, S and Se. $R^1$ and $R^2$ are independently selected from the group consisting of aliphatic, cycloaliphatic, aromatic, arylaliphatic, and arylcycloaliphatic groups (e.g. hydrocarbyl groups) that include 0 to about 3 heteroatoms selected from the group N, O, S, Se and Si. $R^1$ and $R^2$ may for example be or include linear or branched alkyl chains of for example about 1 to about 10 main chain carbon atoms (see above for examples). $R^1$ and $R^2$ may also include other polar, non-polar, saturated or unsaturated groups. Typically $R^1$ and $R^2$ have a main chain of a length of 1 to about 5, to about 10, to about 15 or to about 20 carbon atoms. In typical examples of this embodiment the reaction product includes a decalin ring system, in particular a 2-substituted trimethyl-1,1,4a-decahydronaphthalene compound, such as a 2-substituted 1,1,4a,8a-tetramethyl-tetradecahydrophenanthrene compound (including a Podocarpane derivative), a 2-substituted 1,1,4a-trimethyl-1,2,3,4,4a,9,10,10a-octahydrophenanthrene compound, or a 7-substituted 6,6,9a-trimethyl-dodecahydro-1H-benzindene compound.

As a further illustration, where the isoprenoid compound is of the general formula (VIg) (see above), the process of the present invention can be depicted by the following general scheme (II):

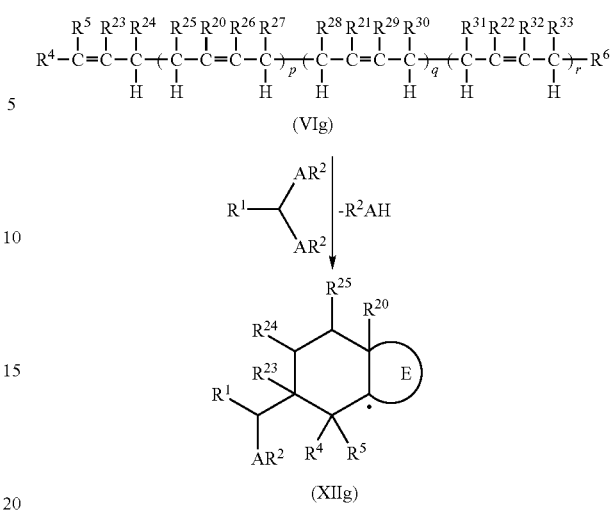

wherein, as above in general formula XII, E in general formula XIIg is an aliphatic, cycloaliphatic or arylaliphatic bridge containing about 3 to about 8 carbon atoms (for example, 5 or 6 carbon atoms), completing a non-aromatic ring that may include 0 up to about 2 heteroatoms. A, $R^1$, $R^2$, $R^4$, $R^5$, $R^{20}$ and $R^{23}$-$R^{25}$ and in formula VIg $R^6$, $R^{21}$, $R^{22}$ and $R^{26}$-$R^{33}$, as well as p-r, are as defined above.

The terminating moiety $R^6$ can virtually be any moiety that does not interfere with the cyclisation reaction, meaning its purpose is to simply provide the needed fourth valency to the terminal carbon atom of the respective isoprenoid unit. The terminating moiety $R^6$ can thus either be a single atom such as a hydrogen atom or alternatively it can be a functional group or moiety. In case $R^6$ in formula (VI) is hydrogen, and p and q are both 1, then the isoprene compound used in the cyclisation reaction could, for example, be 2,6,10-trimethyl-2,6,10-dodecatriene (CAS-No. 7681-88-1), including for instance (E,E)-2,6,10-trimethyl-2,6,10-dodecatriene (CAS-No. 3899-18-1) or (Z,Z)-2,6,10-trimethyl-2,6,10-dodecatriene (CAS-No. 63223-71-2).

Figure 10:
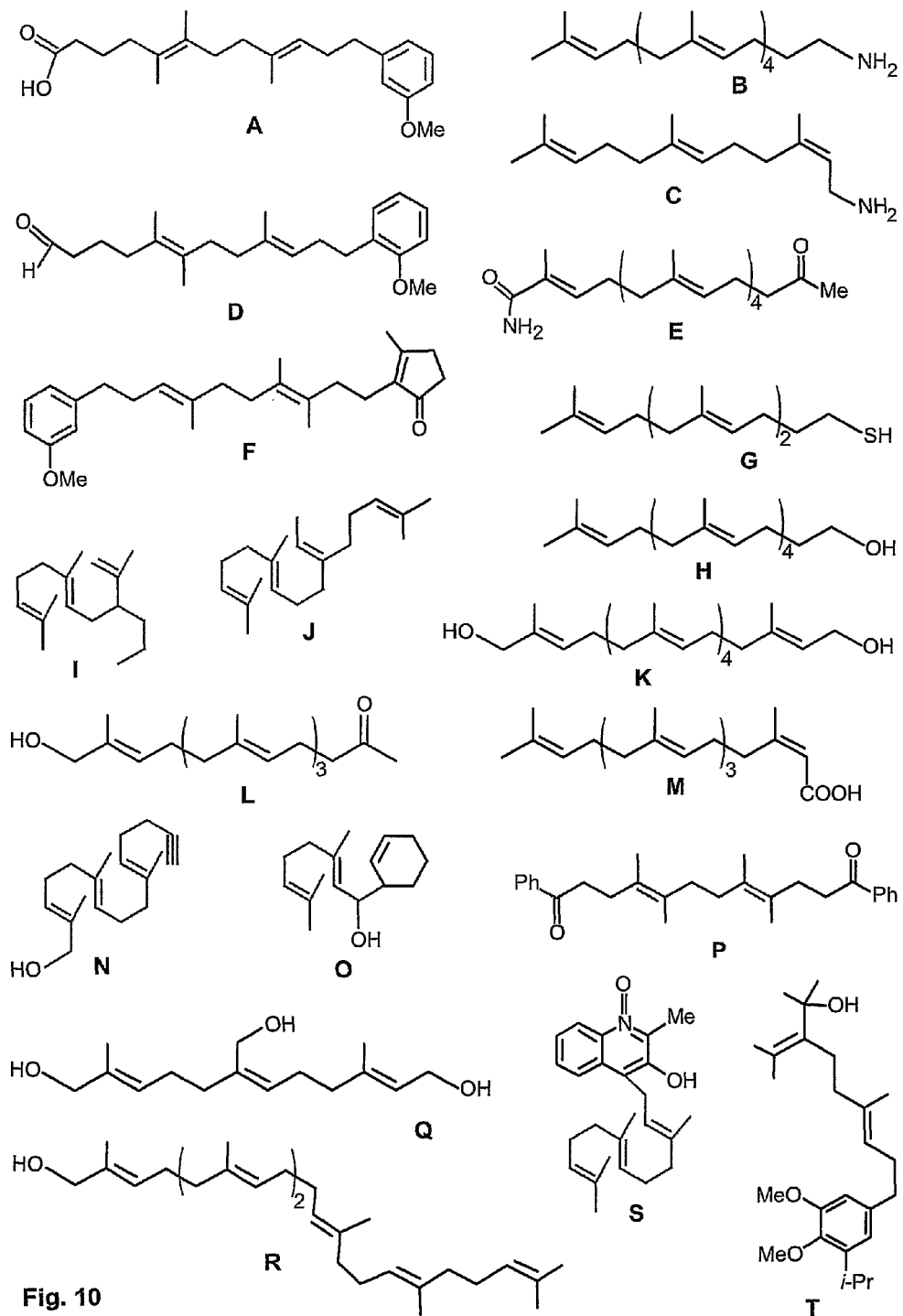
FIG. 10 depicts illustrative examples of isoprenoid compounds that may be used in the process of the present invention.

The terminating moiety $R^6$ may not be structurally included into a ring of the multiple ring compound during the cyclisation process. In such embodiments, moiety $R^6$ may still be present in unaltered form in the multiple ring compound formed during the process of the invention (i.e., the product). FIG. 4 depicts an illustrative example of such an embodiment, in which p and q in formula (IV) are both 1, $R^4$, $R^5$, $R^{20}$, and $R^{21}$ are all methyl and $R^6$ is OAc (acetoxy). FIG. 10 shows further examples of terminating moieties that can be expected to remain unchanged during a cyclisation process of the invention. Two respective examples are (Z,Z)-farnesylamine (compound C, each p and q in formula (VI) are 1), in which the terminating moiety is an amino-group, and (all-E)-2,6,10,14,18,22-hexamethyl-2,6,10,14,18,22-tetracosahexaene-1,24-diol (compound K, in which the sum of p and q in formula (VI) is 5, e.g. p=2 and q=3), in which the terminating moiety is a hydroxy-group.

$R^6$ may alternatively also take part in the cyclisation reaction. Generally, terminating moiety $R^6$, or the moiety into which $R^6$ has transformed, may then be present in a cyclic part of the multiple ring compound as illustrated in FIG. 7 (in which $R^6$ is 3-bromophenylmethyl- and benzyl-, respectively, p in formula (VI) is 1 and q is 0), where the phenyl group forms part of the ring system of the multicyclic product. Another example, where at least a part of the terminating group is part of the ring system of the multicyclic product is shown in FIG. 6. In compound (38) each p and q in formula (VI) are 1, and the ethylene group of the terminating moiety (CH₂C≡CH) is incorporated into the five membered ring. In this case, the triple bond of the terminating alkyne moiety is concurrently converted into a double bond. FIG. 3 depicts yet two further examples of a terminating moiety that is in part incorporated into the multiple ring compound during the cyclisation process. In these embodiments the terminating moiety is 3-hydroxy-3-methyl-1-buten-4-yl- and 2-hydroxypropyl-, respectively (first two vs. third reaction depicted), of which an ethyloxy-part becomes a part of the ring system of the multiple ring compound. In the respective compound (13) the value of p in formula (VI) is 1 and the value of q is 0. Another example of a terminating moiety, a part of which is incorporated into the multiple ring compound, is 2-oxopropyl-, as shown in FIG. 5. An oxoethyl-part of this moiety is incorporated into the ring system of the cyclisation product in form of an oxyethylenyl-part. In the respective compound (23) both p and 1 in formula (VI) are 1, while in compound (26) p in formula (VI) is 1 and q is 0. Other examples can be found in FIG. 10. The benzyl part of $R^6$ (including the phenyl ring thereof) in form of methoxyphenyl-methyl-moieties, as in (E,E)-12-(3-methoxyphenyl)-5,6,9-trimethyl-5,9-dodecadienoic acid (compound G in FIG. 10, in which each p and q in formula (VI) is 1) or (E,E)-2-(3-methoxyphenyl)-5,6,9-trimethyl-5,9-dodecadienal (compound D, not falling under formula (VI)), can for instance be expected to be included into the ring system of the multiple ring compound. In (E,E)-4,5,8,9-tetramethyl-1,12-diphenyl-4,8-dodecadiene-1,12-dione (compound P, not falling under formula (VI)) $R^6$ is 1-oxo-1-phenyl-ethane-2-yl, of which the oxoethyl-part can be expected to become incorporated into the multiple ring compound. The terminating moiety of (Z,E,E,E)-3,7,11,15,19-pentamethyl-2,6,10,14,18-eicosapentaenoic acid (compound M, in which p in formula (VI) is 1 and q is 0) is (Z)-3-methylcrotonoic acid-4-yl-, of which the propenyl-part in the main chain can be expected to become part of the multiple ring compound.

Examples depicted in FIG. 10 of compounds, in which the terminating moiety can be expected to be entirely incorporated into the multiple ring compound, are for instance (4E,8E,12E,16E)-5,9,13,17,21-pentamethyl-4,8,12,16,20-docosapentaen-1-amine (compound B with each p and q in formula (VI) being 2), in which $R^6$ is 2-aminoethyl-, (E,E)-5,9,13-trimethyl-4,8,12-tetradecatriene-1-thiol (compound G, in which each p and q in formula (VI) is 1), in which $R^6$ is 2-mercaptoethyl-, (4E,8E,12E,16E)-5,9,13,17,21-pentamethyl-4,8,12,16,20-docosapentaen-1-ol (compound H, where each p and q in formula (VI) are 2), in which $R^6$ is 2-hydroxyethyl-.

As can also be taken from the appended figures and the explanations below, in embodiments where $R^6$ is not incorporated into the ring structure of the multiple ring compound, this terminating moiety, or the moiety into which it has transformed, is generally bound to a ring of the multiple ring compound, or it is located in vicinity to such a ring. The presence or absence of a methylene-linkage in the terminating moiety $R^6$ of the isoprenoid compound, as for example illustrated by the moieties CH₂—$R^d$ in formulas (VIe) or VIf) above, generally determines the ring size of that ring within the multiple ring product, which carries the moiety $R^6$ or the moiety into which $R^6$ has transformed. In embodiments where the terminating moiety $R^6$ of the isoprenoid compound provides a respective methylene-linkage to an isoprenoid unit of the isoprenoid compound, the cyclisation process typically yields a multiple ring compound, in which said ring (bound or in proximity to moiety $R^6$ or the moeity into which $R^6$ has transformed) is a six-membered ring. In embodiments where no such methylene-linkage is present in the isoprenoid compound a different ring size such as for instance a five-membered ring will typically be obtained. It is however noted in this regard that in some embodiments moiety $R^6$ is included into a ring of the multiple ring compound formed during the process of the invention (see also below).

Cyclisation reactions of isoprenoid compounds occur in various biosynthesis routes, such as the biosynthesis of cholesterol. Similar cyclisation reactions have been used in the laboratory. Both the biosynthesis and conventional acid catalysed cyclisation reactions are thought to occur as a transantiparallel addition at the double bonds of the isoprenoid compound, for example according to the following scheme (III):

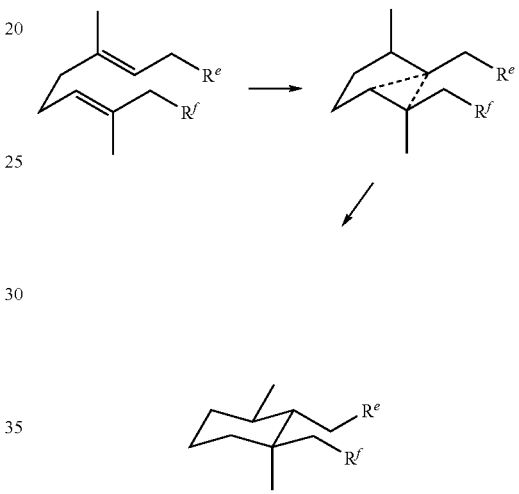

with $R^e$ and $R^f$ being any independently selected group such as H or aliphatic, cycloaliphatic, aromatic, arylaliphatic, and arylcycloaliphatic groups (e.g. hydrocarbyl groups).

While the reaction in biosynthesis is thought to follow a concerted mechanism, experimental data show that the in-vitro performed cyclisation reactions follow a stepwise mechanism via cationic intermediates, in which the respective cationic centre is planar. Accordingly, compounds with both E- and Z-configuration can equally be employed in vitro. Since the method of the present invention includes a respective cyclisation reaction, it can be understood that reactants with any configuration at the double bond of the isoprene unit may be employed. It is however noted that, while the respective reacting molecule includes a planar reaction centre, the entire molecule need nevertheless not necessarily be achiral. The configuration of the double bonds in the reactant may therefore determine the enantiomer produced. Those skilled in the art will in this regard appreciate that the acetal initiator used in the method of the present invention may also determine the enantiomer produced in the cyclisation reaction (see below and e.g. FIG. 16 or 23A).

If a catalyst such as an acid is used, the cyclisation process according to the present invention accordingly includes contacting the isoprenoid compound with a respective catalyst. As already indicated above, the cyclisation process furthermore includes contacting the isoprenoid compound with an initiator. The initiator may for example be of the general formula (II):

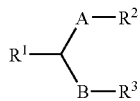

wherein A and B are independently selected heteroatoms selected from O, S and Se. The initiator may accordingly be an oxygen acetal, a thioacetal, or a selenoacetal. $R^1$, $R^2$ and $R^3$ are independently selected from the group consisting of aliphatic, cycloaliphatic, aromatic, arylaliphatic, and arylcycloaliphatic groups (e.g. hydrocarbyl groups). Any of $R^1$-$R^3$ may also include other polar, non-polar, saturated or unsaturated groups, as well as 0 to about 3 heteroatoms selected from the group N, O, S, Se and Si. Typically $R^1$-$R^3$ have a main chain of a length of 1 to about 10, about 15 or about 20 carbon atoms. Each $R^1$, $R^2$ and/or $R^3$ may for example be or include linear or branched alkyl chains of for example about 1 to about 10 main chain carbon atoms. Any acetal compound, i.e. a reaction product of an alcohol and an aldehyde, may for example be used in the present invention.

As two illustrative examples, a respective acetal compound may be of the general formulas:

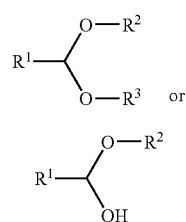

Examples of moieties that may define $R^2$ and $R^3$ include, but are not limited to, methyl-, ethyl-, n-propyl-, 1-methylethyl-, n-butyl-, 1-methylpropyl-, 2-methylpropyl-, 1,1-dimethylethyl-, n-pentyl-, 1-methylbutyl-, 2-methylbutyl-, 1,1-dimethylpropyl, 2,2-dimethylpropyl-, 1,2-dimethylpropyl, 3-methylbutyl-, 1-ethylpropyl-, 2,2-dimethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl and n-octyl. In some embodiments $R^2$ and $R^3$ are identical. In such embodiments a respective acetal compound may for instance be of the general formulas

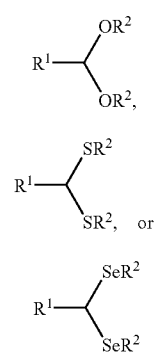

wherein $R^1$ and $R^2$ are independently selected from the group consisting of aliphatic, cycloaliphatic, aromatic, arylaliphatic, and arylcycloaliphatic groups (e.g. hydrocarbyl groups) that include 0 to about 3 heteroatoms selected from the group N, O, S, Se and Si. As noted above, $R^2$ may for example be or include linear or branched alkyl chains of for example about 1 to about 10 main chain carbon atoms (see above for examples). $R^1$ and $R^2$ may also include other polar, non-polar, saturated or unsaturated groups. Typically $R^1$ and $R^2$ have a main chain of a length of 1 to about, to about 10, to about 15 or to 20 carbon atoms. Examples of an acetal of formula (III) include, but are not limited to, dimethyl benzoyl acetal (CAS-No. 66822-20-6), 1,1-diethoxy-butane (CAS-No. 3658-95-5), 1,1'-[propylidene-bis(oxymethylene)]bis-benzene (CAS-No. 23556-91-4), [bis(2-methylpropoxy)methyl]-benzene (CAS-No. 87343-69-9), 9-(diethoxymethyl)-phenanthrene (CAS-No. 94650-46-1), 1-(dimethoxymethyl)-2,4,5-trimethyl-benzene (CAS-No. 65915-93-7), or p-anisaldehyde di-tert-butyl acetal (CAS-No. 32314-58-2). Examples of a thioacetal of formula (IV) include, but are not limited to, 1,1-bis(ethylthio)-butane (CAS-No. 3393-16-6), 1,1-bis(ethylthio)-propane (CAS-No. 7282-08-8), butyraldehyde di-tert-butyl mercaptal (CAS-No. 32931-12-7), benzaldehyde diethyl mercaptal (CAS-No. 7334-52-3) and [2,2-bis(methylthio)ethyl]-benzene (CAS-No. 15362-00-2). Examples of a selenoacetal of formula (IV) include, but are not limited to, 1-[bis(methylseleno)methyl]-4-methyl-benzene (CAS-No. 131141-36-1), [1,1-bis(methylseleno)pentyl]-benzene (CAS-No. 147677-96-1), 1,1-bis(ethylseleno)-heptane (CAS-No. 103971-75-1), 1-phenyl-1,1-bis(methylseleno)ethane (CAS-No. 94417-53-5), 1,1'-[(phenylmethylene)bis(selenomethylene)]bis-benzene (CAS-No. 144403-85-0), and 1,1-bis[(1-methylethyl)seleno]-heptane (CAS-No. 103971-80-8). In some embodiments the moieties $R^2$ form a bridge, so as to form a cyclic structure as represented by the following general formula (I):

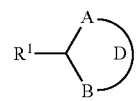

in which again $R^1$ is selected from the group consisting of aliphatic, cycloaliphatic, aromatic, arylaliphatic, and arylcycloaliphatic groups (e.g. hydrocarbyl groups), that includes 0 to about 3 heteroatoms selected from the group N, O, S, Se and Si (see above). A and B are independently selected heteroatoms selected from O, S and Se. D is an aliphatic, cycloaliphatic or arylaliphatic bridge containing 1 to about 12 carbon atoms, such as 1 to about 10, 1 to about 8 or 1 to about 6 carbon atoms, completing a non-aromatic ring that includes 0 to about 2 heteroatoms.

Three illustrative examples of a structure with a respective bridge are a 1,3-dioxolane structure, a 1,3-dioxane structure and a 1,3-dioxepane structure. Examples of a respective acetal of formula (I) include, but are not limited to, 2-(1-methylethyl)-1,3-dioxolane (CAS-No. 822-83-3), 2-phenyl-1,3-dioxolane (CAS-No. 936-51-6), 2-cyclohexyl-1,3-dioxolane (CAS-No. 4362-48-5), 2-(3-methyl-2-butenyl)-2-phenyl-1,3-dioxolane (CAS-No. 69803-72-1), 2-phenyl-1,3-dioxane (CAS-No. 772-01-0), 2-(2-methylpropyl)-1,3-dioxane (CAS-No. 66909-14-6), 2-heptyl-1,3-dioxane (CAS-No. 5702-44-3), 2-pentyl-1,3-dioxepane (CAS-No. 132088-01-8), 4-(1,3-dioxepan-2-yl)-2-methyl-quinoline (CAS-No. 96517-50-9) and 2-phenyl-1,3-dioxepane (CAS-No. 2749-68-0). Examples of a respective thioacetal of formula (I) include, but are not limited to, 2-(phenylmethyl)-1,3-dithiane (CAS-No. 31593-52-9), 2-phenyl-1,3-dithiolane (CAS-No. 5616-55-7), 2-(1-methylethyl)-1,3-dithiolane (CAS-No. 26733-24-4), 2-(1-naphthalenylmethyl)-1,3-dithiolane (CAS-No. 623582-18-3), 2-(2-ethoxyethyl)-1,3-dithiane (CAS-No. 915695-50-0), 5-(1,3-dithian-2-yl)-3,4-dihydro-2H-pyrrole (CAS-No. 127811-85-2), (1,1-dimethylethyl)[5-(1,3-dithian-2-yl)-2-methoxyphenoxy]dimethyl-silane (CAS-No. 877438-48-7), (1,1-dimethylethyl)[3-(1,3-dithian-2-yl)phenoxy]dimethyl-silane (CAS-No. 877438-46-5), 2-phenyl-1,3-dithiepane (CAS-No. 117203-56-2), 3-cyclohexyl-1,5-dihydro-2,4-benzodithiepin (CAS-No. 152656-59-2) and 2-propyl-1,3-dithiepane (CAS-No. 885669-09-0). Examples of a respective selenooacetal of formula (III) include, but are not limited to, 2,2-diphenyl-1,3-diselenolane (CAS-No. 377780-32-0), 2-phenyl-1,3-diselenane (CAS-No. 184002-13-9), 2-methyl-1,3-diselenane (CAS-No. 121955-76-8), 8-(1,1-dimethylethyl)-1,4-diselenaspiro[4.5]decane (CAS-No. 153909-93-4) and 2-hexyl-1,3-diselenepane (CAS-No. 103971-78-4).

During the cyclisation process one of the ether-, thioether- or selenoether-bonds to the carbonylic carbon atom (carrying $R^1$) of the acetal is cleaved (see e.g. formulas (I) and (II) above, see also scheme (VI) below). In embodiments where the acetal is of formula (II), only the other ether-, thioether- or selenoether-bond becomes incorporated into the multiple ring compound. In embodiments where an initiator of general formula (II) is used, the initiator may include different heteroatoms at the respective positions, which are indicated by "A" and "B" (see above). As an illustrative example, A may be sulphur, while B may be selenium. In the course of the cyclisation process, either of these two heteroatoms may be included into the multiple ring compound. Accordingly, two different reaction products may occur in such embodiments. One possible reaction product includes the heteroatom labelled as "A" in general formula (II). Another possible reaction product includes the heteroatom labelled as "B" in general formula (II). As an illustrative example, a compound of general formula (VIII), such as a phenyl-substituted (including H) (3E)-4,8-dimethyl-1-phenyl-nona-3,7-diene (1) (see also e.g. FIG. 1) may be used as the isoprenoid compound. Using an acetal initiator of general formula (II) (see above), the two tricyclic compounds depicted in the following scheme (IV) may be obtained:

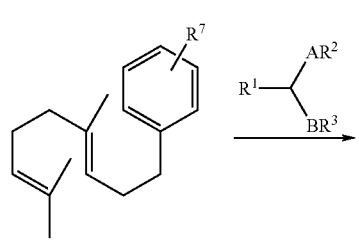

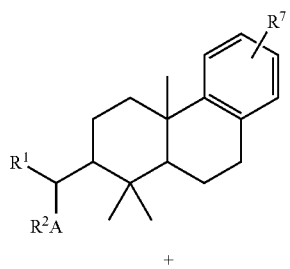

+

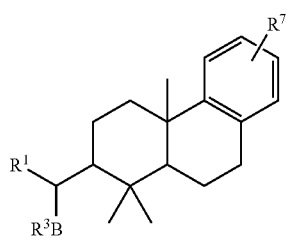

The person skilled in the art can however easily predict which product will be, or will mostly be formed, taking into consideration the properties of the respective leaving groups and heteroatoms included in the acetal initiator.

In embodiments where the heteroatoms of the acetal bonds are identical, such as in formulas (IIb), (III), (IV) or (V), only one addition intermediate can occur. Accordingly only one respective cyclisation product will be obtained. The same applies correspondingly in embodiments were a semiacetal is selected as the initiator. In such embodiments the cyclisation process can be depicted by the following scheme V (see also above):

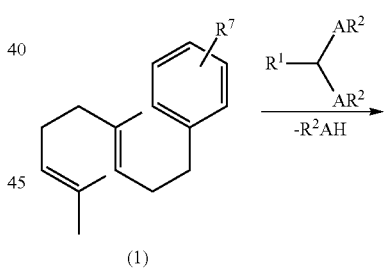

(1)

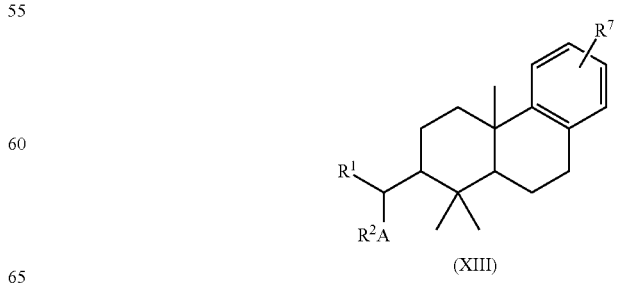

(XIII)

Without wishing being bound by theory it is believed that the initiator is assisted by the catalyst in adding to a double bond of the isoprenoid compound as illustrated in the following scheme (VI):

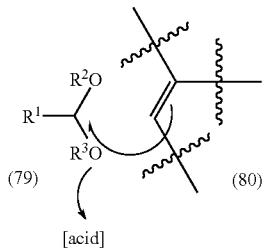

wherein (79) is an acetal as an exemplary initiator and (80) is a cut-out, i.e. an incomplete formula for illustration purposes, representing an isoprenoid unit of the isoprenoid compound. Overall the initiator electrophilically adds to a double bond of the isoprenoid compound. As a result a covalent bond between the isoprenoid compound and the initiator is formed. As noted above, the cyclisation reaction follows a stepwise mechanism via cationic intermediates. As a consequence thereof, the isoprene units of the isoprenoid compound may be of any configuration at its double bond(s). As a further consequence, steric and stereoselective conditions determine the structure of the multiple ring compound generated. If the isoprenoid compound includes three isoprenoid units according to general formulas (VI) or (VII) (i.e. m in formula (VII) is at least two) the cyclisation reaction in all cases, i.e. regardless of the configuration of the double bonds of the isoprenoid compound, results in the formation of a trans-decalin system (cf. scheme I to scheme III).

In typical embodiments the acetal initiator undergoes an electrophilic addition reaction with the terminal double bond of the isoprenoid compound as illustrated by the following scheme (VII):

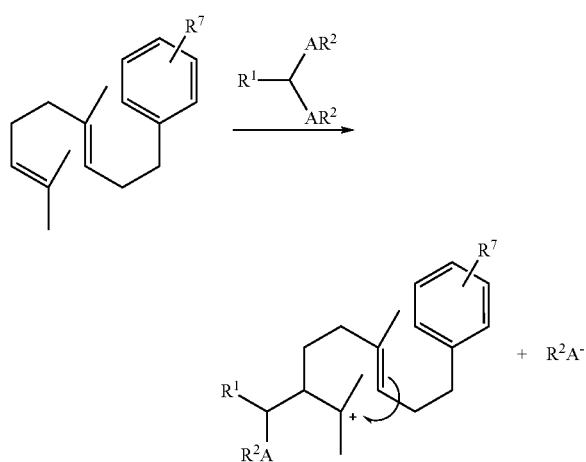

Again a covalent bond between the acetal initiator and the isoprenoid compound is formed. As can be inferred from the above equation, this addition reaction initiates the cyclisation reaction. The entire reaction can be schematically represented by scheme V above.

Figure 14:
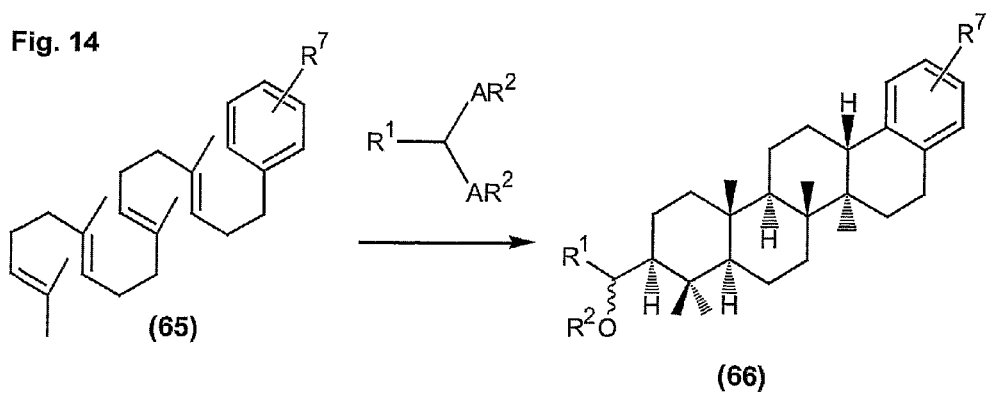
FIG. 14 depicts the reaction scheme of a further embodiment of the cyclisation process.

In embodiments where the isoprenoid compound used includes more than one isoprene unit—such as the embodiments depicted in schemes (IV) or (VII) or in FIG. 14—the cyclisation reaction typically includes at least two isoprene units, typically all isoprene units present in the respective compound. Depending on the conditions selected, however a byproduct of cyclisation of only one isoprene unit, or a lower number of isoprene units than present in the compound (and accordingly also in the isoprenoid compound), often occurs. The entire reaction of a respective embodiment can be schematically represented by the reaction scheme depicted in FIG. 1A.

The obtained reaction product is likewise a compound that includes isoprene units. In contrast to the isoprenoid compound that is the reactant, the reaction product includes a smaller number of acyclic isoprene units. In some embodiments the reaction product, which may be the main reaction product, includes solely cyclic isoprene units. The reaction product is herein referred to as a ring terpenoid compound, i.e. an at least partly cyclic compound, in particular a compound including polycyclic moieties, which is a terpene derivative. Terpenes, a large and varied class of hydrocarbons which are largely natural products, are build up of isoprenoid and/or isopentenoid units. Typically ring terpenoid compounds are built by fusion of isoprene units, such as at least one, typically two or more isoprene units. Where only one isoprene unit is included in a ring terpenoid compound, the compound is built by fusion with a further moiety that includes an unsaturated bond, typically a double bond. Such an unsaturated bond may still be present in the ring terpenoid compound. In a ring terpenoid compound the respective isoprenoid unit(s) is/are part of a five- or six-membered ring. In addition, a ring terpenoid compound may include one or more further isoprenoid units that are not integrated into a ring. Several such rings may be fused to a bi-, tri-, tetra- or pentacyclic ring system. Ring terpenoid compounds have structures that differ both in terms of functional groups and side chains as well as in their basic carbon skeletons. Terpenoid compounds obtainable by the cyclisation process of the present invention typically include a 1,1-dimethyl-cyclohexane moiety (see above). Ring terpenoid compounds are produced primarily by a wide variety of plants and are included in e.g. fruits and vegetables, and are main constituents of inter alia odorants, essential oils, balsams, traditional herbal remedies, oleoresins of plants, biogenic metabolites with antimacrofouling and antifungal properties, and provide various classes of compounds such as steroids or cannabinoids.

The term "derivative" as used herein thus refers to a compound which differs from another compound of similar structure by the replacement or substitution of one moiety by another. Respective moieties include, but are not limited to atoms, radicals or functional groups. For example, a hydrogen atom of a compound may be substituted by alkyl, carbonyl, acyl, hydroxyl, or amino functions to produce a derivative of that compound. Respective moieties include for instance also a protective group that may be removed under the selected reaction conditions.

As an illustrative example, where the isoprenoid compound is trans-2,6-dimethyl-9-phenyl-2,6-nonadiene (1), the reaction can be represented by the following scheme (VIII):

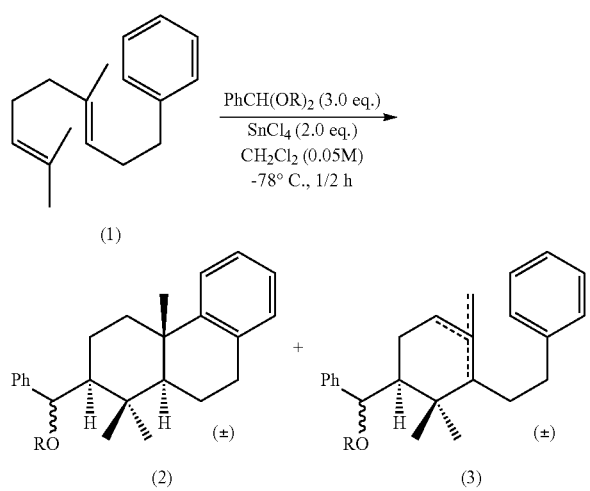

In such embodiments product (2) is obtained in high yields. It is noted in this regard that the reaction conditions, including the acid used (see below), have an effect on the yield of product (2) obtained. In the example depicted in scheme (VII) the use of tin(IV) chloride result in particularly high yields. FIG. 1B depicts examples of the yields obtained with various acetals under the indicated conditions. In all cases, the cyclised products are obtained in good to excellent yields. Small amounts of monocyclised products are obtained in some cases (FIG. 1B, entries 1 to 4). Increasing bulkiness of acetals does not affect the excellent reaction rates and yields of the intermolecular reactions (FIG. 1B, entry 4). Especially noteworthy, reactions using benzaldehyde cyclic acetals (FIG. 1B, entries 5 to 6) proceed smoothly to give the desired products in good to excellent yields without detection of the mono-cyclisation products. The skilled artisan will furthermore appreciate in this regard that the yields obtained using the cyclisation process of the invention are significantly higher than the yields of a conventional Lewis acid catalysed cyclisation reaction carried out in the absence of an initiator (see e.g. Rosales, V., et al., *J. Org. Chem.* (2002) 67, 1167-1170).

Contacting the isoprenoid compound with the catalyst and the initiator is carried out at a temperature selected appropriately according to the remaining reaction conditions and may be conveniently optimised in a laboratory. In some embodiments the respective working temperature is chosen at or below room temperature, which is generally about 25° C. to about 30° C. The temperature may for example be selected in the range between about −78° C. and about 25° C., such as in the range between about −78° C. and about 0° C. In typical embodiments the entire cyclisation reaction is performed at this temperature. Other techniques or reactions that precede or follow the above illustrated cyclisation reaction, may be carried out at any desired temperature, including the same temperature as selected for the cyclisation reaction.

Any suitable solvent may be used when contacting the isoprenoid compound with the catalyst and the initiator, whether nonpolar aprotic, nonpolar protic, dipolar protic or dipolar aprotic. The terms polar and non-polar are often used to classify liquids with reference to their properties in terms of solubility and miscibility with other liquids. Polar liquids typically contain molecules with an uneven distribution of electron density. The polarity of a molecule is reflected by its dielectric constant or its dipole moment. Polar molecules are typically further classified into protic and non-protic (or aprotic) molecules. A fluid, e.g. a liquid, that contains to a large extent polar protic molecules may therefore be termed a polar protic fluid. A liquid, e.g. a solvent, that contains to a large extent polar non-protic molecules may be termed a polar non-protic fluid. Protic molecules contain a hydrogen atom which may be an acidic hydrogen when the molecule is dissolved for instance in water or an alcohol. Aprotic molecules do not contain such hydrogen atoms.

Examples of non-polar solvents include, but are not limited to, hexane, heptane, cyclohexane, benzene, toluene, pyridine, dichloromethane, 1,2-dichloroethane, chloroform, carbon tetrachloride, carbon disulfide, tetrahydrofuran, dioxane, diethyl ether, diisopropylether, ethylene glycol monobutyl ether or tetrahydrofuran. Examples of dipolar aprotic liquids are methyl ethyl ketone, chloroform, tetrahydrofuran, ethylene glycol monobutyl ether, pyridine, methyl isobutyl ketone, acetone, cyclohexanone, ethyl acetate, isobutyl isobutyrate, ethylene glycol diacetate, dimethylformamide, acetonitrile, N,N-dimethyl acetamide, nitromethane, acetonitrile, N-methylpyrrolidone, methanol, ethanol, propanol, isopropanol, butanol, N,N-diisopropylethylamine, and dimethylsulfoxide. Examples of polar protic liquids are water, methanol, isopropanol, tert.-butyl alcohol, formic acid, hydrochloric acid, sulfuric acid, acetic acid, trifluoroacetic acid, dimethylarsinic acid [$(CH_3)_2AsO(OH)$], acetonitrile, phenol or chlorophenol.

Ionic liquids, which may also be used as solvents, typically have an organic cation and an anion that may be either organic or inorganic. The polarity of ionic liquids (cf. below for examples) is known to be largely determined by the associated anion. While e.g. halides, pseudohalides, $BF_4^-$, methyl sulphate, $NO_3^-$, or $ClO_4^-$ are polar liquids, hexafluoro-phosphates, $AsF_6^-$, bis(perfluoroalkyl)-imides, and $[C_4F_6SO_3]^-$ are non-polar liquids. Examples of a polar ionic liquid include, but are not limited to, 1-ethyl-3-methylimidazolium tetrafluoroborate, N-butyl-4-methylpyridinium tetrafluoroborate, 1,3-dialkylimidazolium-tetrafluoroborate, 1,3-dialkylimidazolium-hexafluoroborate, 1-ethyl-3-methylimidazolium bis(pentafluoroethyl)phosphinate, 1-butyl-3-methylimidazolium tetrakis(3,5-bis(trifluoromethylphenyl)borate, tetrabutyl-ammonium bis(trifluoromethyl)imide, ethyl-3-methylimidazolium trifluoromethanesulfonate, 1-butyl-3-methylimidazolium methylsulfate, 1-n-butyl-3-methylimidazolium ([bmim]) octylsulfate, and 1-n-butyl-3-methylimidazolium tetrafluoroborate. Examples of a nonpolar ionic liquid include, but are not limited to, 1-ethyl-3-methylimidazolium bis[(trifluoromethyl)sulfonyl]amide bis (triflyl)amide, 1-ethyl-3-methylimidazolium bis [(trifluoromethyl)sulfonyl]amide trifluoroacetate, 1-butyl-3-methylimidazolium hexafluorophosphate, 1-hexyl-3-methylimidazolium bis(trifluoromethylsulfonyl)imide, 1-butyl-3-methylimidazolium bis(trifluoromethylsulfonyl) imide, trihexyl(tetradecyl)phosphonium bis[oxalato(2-)]borate, 1-hexyl-3-methyl imidazolium tris(pentafluoroethyl)trifluorophosphate, 1-butyl-3-methyl-imidazolium hexafluorophosphate, tris-(pentafluoroethyl)trifluorophosphate, trihexyl(tetradecyl)phosphornium, N'''-ethyl-N,N,N', N'-tetramethylguanidinium, 1-butyl-1-methylpyrrolidinium tris(pentafluoroethyl)trifluorophosphate, 1-butyl-1-methylpyrrolidinium bis(trifluoromethylsulfonyl)imide, 1-butyl-3-methyl imidazolium hexafluorophosphate, 1-ethyl-3-methylimidazolium bis(trifluoromethylsulfonyl)imide and 1-n-butyl-3-methylimidazolium.

It should be understood that suitable solvents will allow for a cyclisation reaction to take place. Examples of nonpolar aprotic solvents include, but are not limited to, hexane, heptane, cyclohexane, benzene, toluene, pyridine, dichloromethane, 1,2-dichloroethane, chloroform, carbon tetrachloride, carbon disulfide, tetrahydrofuran, dioxane, diethyl ether, diisopropylether, ethylene glycol monobutyl ether or tetrahydrofuran. Examples of dipolar aprotic solvents are methyl ethyl ketone, methyl isobutyl ketone, acetone, cyclohexanone, ethyl acetate, isobutyl isobutyrate, ethylene glycol diacetate, dimethylformamide, acetonitrile, N,N-dimethyl acetamide, nitromethane, acetonitrile, N-methylpyrrolidone, and dimethylsulfoxide. Examples of polar protic solvents are methanol, ethanol, butyl alcohol, formic acid, dimethylarsinic acid [$(CH_3)_2AsO(OH)$], N,N-dimethylformamide, N,N-diisopropylethylamine, or chlorophenol. Examples of nonpolar protic solvents are acetic acid, text.-butyl alcohol, phenol, cyclohexanol, or aniline. In some embodiments a nonpolar solvent, in particular a nonpolar aprotic solvent, such as hexane, heptane, carbon disulfide, benzene, toluene, p-xylene, pyridine, aniline, dichloromethane, chloroform, carbon tetrachloride, tetrahydrofuran, methyl ethyl ketone, methyl isobutyl ketone, acetone, cyclohexanone, ethyl acetate, isobutyl isobutyrate, dioxane, diethyl ether, diisopropylether, ethylene glycol monobutyl ether, tetrahydrofuran is used.

Although the invention is neither limited to non-reactive nor to reactive solvents, for the selection of the solvent it may be taken into consideration that certain solvents may be able to undergo an electrophilic addition to the double bond of an isoprenoid compound. In some embodiments such side reactions may be undesired. While under low temperatures such side reaction generally occurs on a minor scale, if at all, in these cases, solvents may be selected that are not capable of forming an electrophil which may react in addition reactions to double bonds. Alternatively, in these cases it may be sufficient to choose solvents with electrophiles of a lower electrophilicity than the initiator selected for the cyclisation process.

In some embodiments the terminating moiety of the isoprenoid compound, indicated as $R^6$ in formulas (VIg), (VI) and (VII) (see above) may include or consist of an alkyl (e.g. hydrocarbyl) chain, functional group or other moiety (see above) that forms a respective substituent of the multiple ring compound after the cyclisation process. In some embodiments the terminating moiety may include or consist of a moiety that is included into the multiple ring compound during the cyclisation process. The respective moiety may thus become a part of the multiple ring compound after the cyclisation process. Examples include, but are not limited to, an aromatic group (see e.g. FIG. 1), a hydroxymethylene-group (see FIG. 3), an alkenyl group (see FIG. 4) and a carbonyl group (see FIG. 5). In other embodiments the terminating moiety may give rise to the formation of a five-membered ring structure in the multiple ring compound during the cyclisation process. Stereoselective and/or steric conditions may for example exclude the formation of a six-membered ring. An illustrative example of such a terminating moiety is an alkynyl group (FIG. 6)

An acetal that may be used in the present invention includes at least one chiral centre. This chiral centre includes the carbonyl carbon atom carrying to the heteroatoms selected from the group oxygen, selenium and sulfur. This carbon atom for instance corresponds to the carbon atom of the carbonyl group of an aldehyde from which the respective acetal was formed. This may be easily seen when depicting the respective hydrogen atom as in the following example:

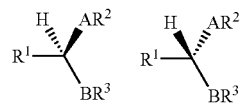

Moieties A, B, and $R^1$ to $R^3$ are as defined above.

In some embodiments the acetal initiator includes one or more further chiral centers. In such embodiments the cyclisation process of the invention may be an enantioselective cyclisation. Typically, the acetal initiator induces in such embodiments enantioselectivity.

Figures 15A, 15B:
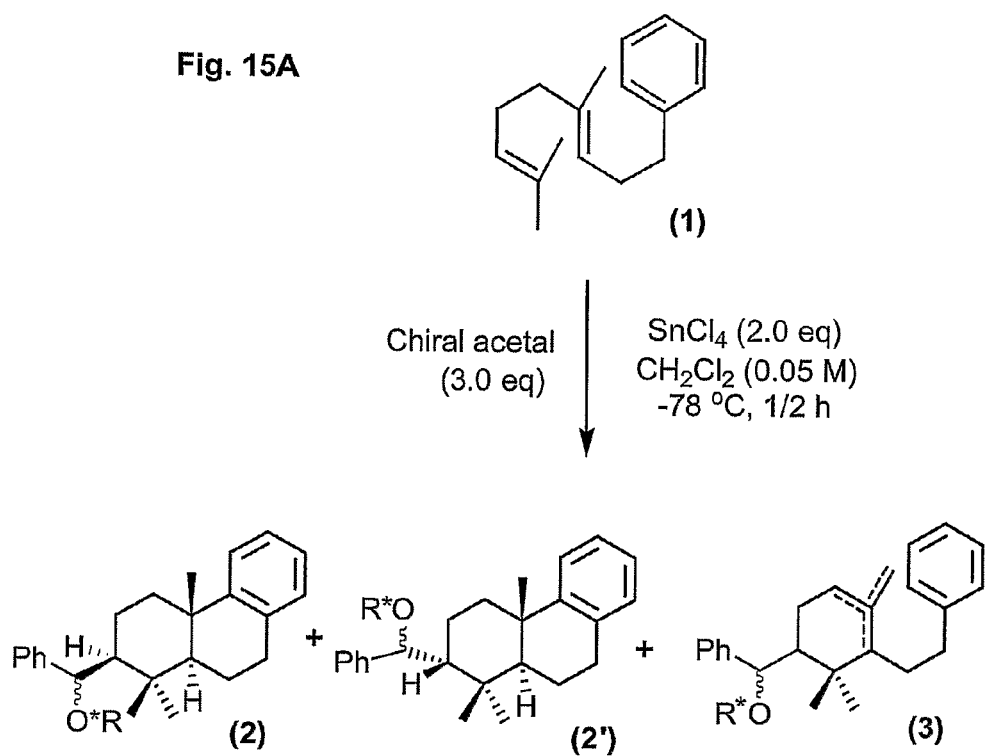
FIG. 15A shows an exemplary scheme of an embodiment of the cyclisation process of preparing a multiple ring compound using chiral acetal templates.
FIG. 15B shows a table summarising the obtained products using two illustrative acetals.

An illustrative example of a reaction initiated by a chiral acetal is provided by the scheme depicted in FIG. 15A.

As a further illustrative example, the initiator may be of the general formulas (IX) to (XI):

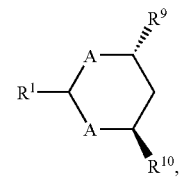

(IX)

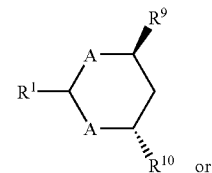

(X)

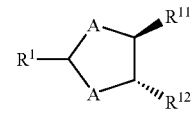

(XI)

In the following, compounds of the general formulas (IX) and (XI) are also addressed as compounds (7) and (8), respectively. $R^1$ is a moiety as defined above. $R^9$ and $R^{10}$ in formulas (IX) and (X) and $R^{11}$ and $R^{12}$ in formula (XI) may independently be selected from the group consisting of H, aliphatic, cycloaliphatic, aromatic, arylaliphatic, and arylcycloaliphatic groups (e.g. hydrocarbyl groups), including 0 to about 3 heteroatoms selected from the group including or consisting of N, O, S, Se and Si. $R^9$ to $R^{12}$ may also include other polar, non-polar, saturated or unsaturated groups. Typically $R^9$ to $R^{12}$ have a main chain of a length of 1 to about 20 carbon atoms. $R^9$ to $R^{12}$ may for example be or include linear or branched alkyl chains of for example about 1 to about 10 main chain carbon atoms. Examples include, but are not limited to, methyl-, ethyl-, n-propyl-, 1-methylethyl-, n-butyl-, 1-methylpropyl-, 2-methylpropyl-, 1,1-dimethylethyl-, n-pentyl-, 1-methylbutyl-, 2-methylbutyl-, 1,1-dimethylpropyl, 2,2-dimethylpropyl-, 1,2-dimethylpropyl, 3-methylbutyl-, 1-ethylpropyl-, 2,2-dimethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl and n-octyl. In some embodiments $R^5$ and $R^6$, and $R^8$ and $R^9$, respectively, are identical.

In this regard the present invention also provides a novel cyclic acetal. This acetal is of the general formula (XIV):

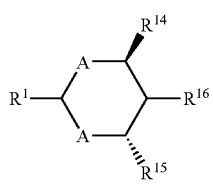

wherein $R^1$, $R^{14}$, $R^{15}$ and $R^{16}$ are independently selected from aliphatic, cycloaliphatic, aromatic, arylaliphatic, arylcycloaliphatic groups (e.g. hydrocarbyl groups), including 0 to about 3 heteroatoms selected from the group N, O, S, Se and Si. Any of $R^1$, $R^{14}$, $R^{15}$ and $R^{16}$ may for example be or include linear or branched alkyl chains of for example about 1 to about 10 main chain carbon atoms (see above for examples). $R^1$, $R^{14}$, $R^{15}$ and $R^{16}$ may also include other polar, non-polar, saturated or unsaturated groups. Typically $R^1$, $R^{14}$, $R^{15}$ and $R^{16}$ have a main chain of a length of 1 to about 20 carbon atoms. A is selected from O, S and Se. In some embodiments $R^1$ is phenyl. In some embodiments $R^{14}$ and $R^{15}$ are identical and may for example be methyl or ethyl. $R^{16}$ may in some embodiments be H or a $C_1$-$C_6$ alkyl chain, for example, methyl or ethyl, an aryl moiety such as phenyl or an arylalkyl moiety such as benzyl. An illustrative example of an acetal of formula (XIV) is (4S,6S)-4,6-dimethyl-2-phenyl-1,3-dioxane.

A cyclic acetal of the general formula (XIV) may be produced by reacting an aldehyde of the general formula $R^1CHO$ (see above for the definition of $R^1$) with the respective 1,3-difunctional compound of the general formula (XV)

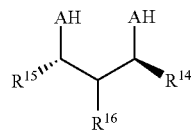

wherein $R^{14}$ and $R^{15}$ are independently selected from the group consisting of aliphatic, cycloaliphatic, aromatic, arylaliphatic, and arylcycloaliphatic groups (e.g. hydrocarbyl groups) that includes 0 to about 3 heteroatoms selected from the group consisting of N, O, S, Se and Si. $R^{16}$ is H or an aliphatic, cycloaliphatic, aromatic, arylaliphatic, or arylcycloaliphatic group (e.g. hydrocarbyl groups) that includes 0 to about 3 heteroatoms selected from N, O, S, Se and Si. A is selected from O, S and Se. As an illustrative example, the 1,3-difunctional compound may be (S,S)-2,4-pentanedithiol (Chemical Abstracts No. 84799-98-4).

As an illustrative example, a "1,3-diol" of the general formula (XVI) may be employed:

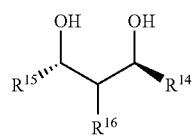

wherein $R^{14}$, $R^{15}$ and $R^{16}$ are as defined above.

Examples of a respective 1,3-diol of formula (XVI) include, but are not limited to, (S,S)-2,4-pentanediol (Chemical Abstracts No. 72345-23-4), (S,S)-2,4-hexanediol (CAS-No. 129025-60-1), (S,S)-3,5-heptanediol (CAS-No. 129212-21-1), (S,S)-3,5-octanediol (CAS-No. 129025-63-4), (S,S)-4,6-nonanediol (CAS-No. 36685-06-0), (1R,3S)-1-phenyl-1,3-butanediol (CAS-No. 90026-44-1), (R,R)-1,3-diphenyl-1,3-propanediol (CAS-No. 77291-92-0), (S,S)-1,5-diphenyl-2,4-pentanediol (CAS-No. 135943-83-8), (S,S)-3-methyl-2,4-pentanediol (CAS-No. 112420-26-5) and (R,R)-2-methyl-1,3-diphenyl-1,3-propanediol (CAS-No. 283169-78-8).

In some embodiments the AH-groups of the 1,3-difunctional compound of the general formula (XV) (e.g. the hydroxyl groups of the 1,3-diol of the general formula (XVI)) are shielded by a protective group. In the shielded form a respective compound is typically of general formula XVII:

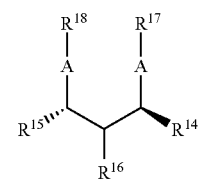

wherein $R^{14}$, $R^{15}$ and $R^{16}$ are as defined above. $R^{17}$ and $R^{18}$ are independently selected aliphatic, cycloaliphatic, aromatic, arylaliphatic, and arylcycloaliphatic groups (e.g. hydrocarbyl groups), including 0 to about 3 heteroatoms selected from the group including or consisting of N, O, S, Se and Si. Each of $R^{17}$ and $R^{18}$ may also be H. $R^{17}$ and $R^{18}$ may also include other polar, non-polar, saturated or unsaturated groups. Typically $R^{17}$ and $R^{18}$ have a main chain of a length of 1 to about 20 carbon atoms. $R^{17}$ and $R^{18}$ may for example be or include linear or branched alkyl chains of for example about 1 to about 10, or to about 15 main chain carbon atoms.

Examples of suitable protective groups include, but are not limited to, methylethyl-, n-propyl-, isopropyl-, acetyl-, tetrahydropyranyl-, methoxymethyl-, β-methoxyethoxy-methyl-, 1,1,1,3,3,3-hexafluoroisopropyl-, trimethylsilyl-, triethylsilyl-, tri-isopropyl-silyl-, di-isopropyl-methyl-silyl, tertiary-butyl-dimethyl-silyl-, tertiary-butyl-diphenyl-silyl-, (tris-(trimethylsilyl)silyl)-, trifluorosulfonyl-, toluenesulfonyl-, p-methoxybenzyl-, tertiary-butyl, methylsulfonyl, allylsulfonyl-, allyl-, allylsilyl-, pivaloyl-, methylthiomethyl-, 2-(dimethyl (2-naphthylmethyl)silyl)ethoxy carbanoyl-, to name a few. Three illustrative examples of a compound of formula XVII are (S,S)-2,2,4,6,8,8-hexamethyl-3,7-dioxa-2,8-disilanonane (compound 68, CAS-No. 107951-71-3), (S,S)-4-[[dimethyl(1,1,2-trimethylpropyl)silyl]oxy]-2-pentanol (CAS-No. 166412-17-5) and (αR,γS)-γ-[(dimethylphenylsilyl)oxy]-α-methyl-benzenepropanol (CAS-No 497069-35-9).

Figure 17:
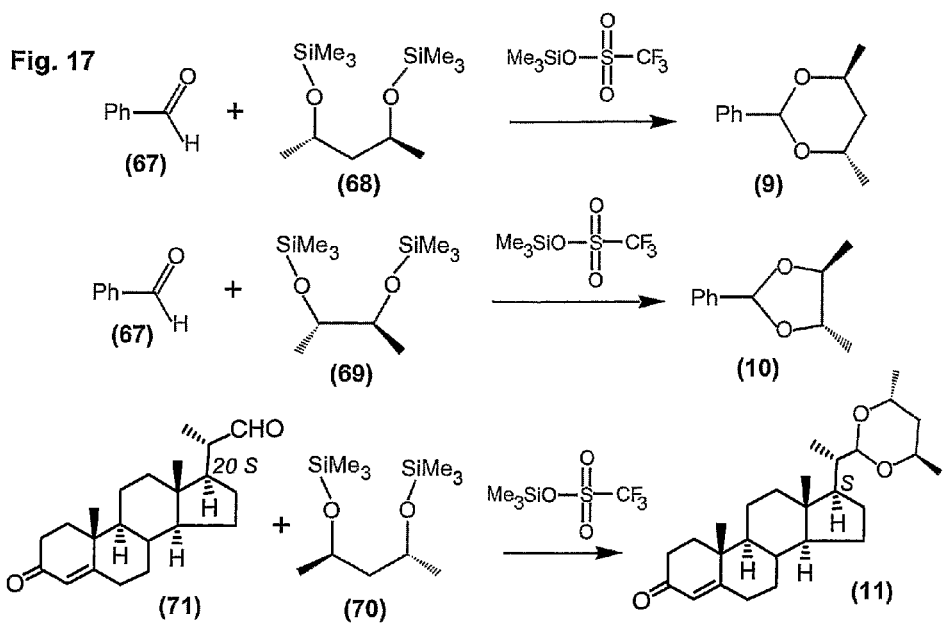
FIG. 17 depicts the synthesis of exemplary chiral acetal initiators.

A cyclic acetal of the general formula (XIV) may be produced starting from the respective diols as illustrated in FIG. 17. As described above, a respective acetal is useful in the cyclisation process of the present invention (see also below).

The stereochemistry of the reactants and reaction products may be analysed according to any method known in the art, such as for instance 2D-NMR based on homo- or heteronuclear J-coupling values (Riccio, R., et al., *Pure Appl. Chem.* (2003) 75, 2-3, 295-308), electron ionisation mass spectrometry, polarimetry, circular dichroism spectroscopy (e.g. using the split Cotton-effect based on the Davydov splitting, see e.g. Allemark, S. G., *Nat. Prod. Rep.* (2000) 17, 145-155), enantioselective chromatography, derivatisation in combination with standard analytical techniques such as NMR, including any suitable 2D-NMR technique, for example based on the nuclear Overhauser effect, as well as X-ray crystallography or solid state NMR (see e.g. Harper, J. K., et al., *J. Org. Chem.* (2003) 68, 4609-4614). Depending on the reaction conditions, in particular the initiator selected, moderate to good stereoselectivity can be achieved using the method of the present invention, while yields can be maintained high. It is noted in this regard that the yields and stereoselectivities disclosed herein as examples have been obtained under reaction conditions that have not been optimised.

Figure 16:
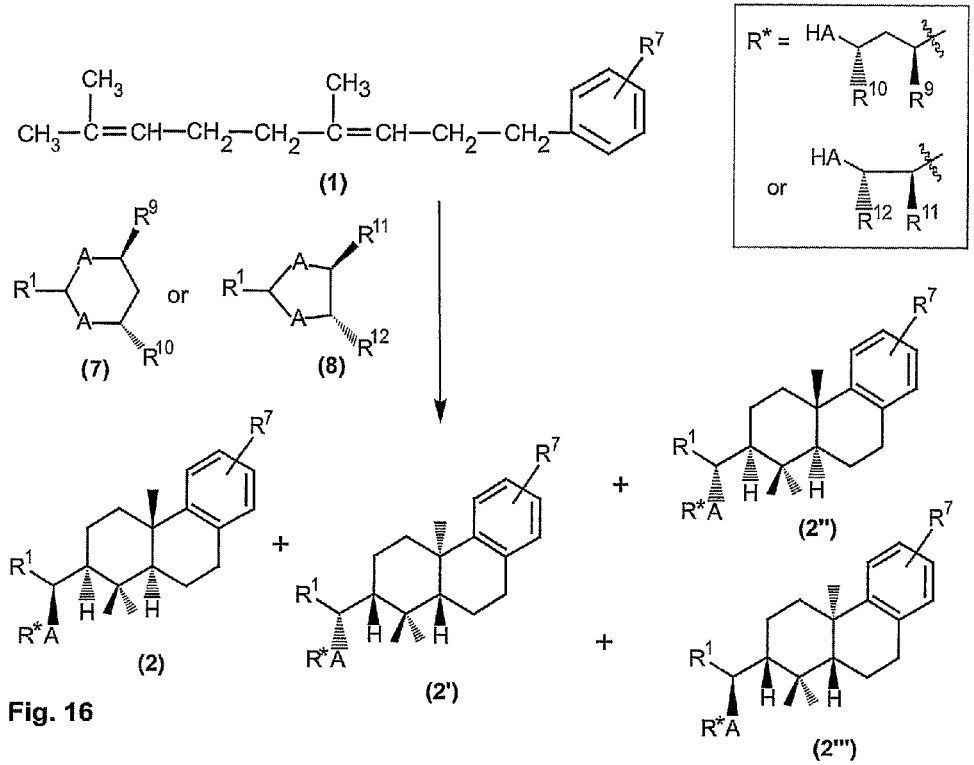
FIG. 16 depicts an exemplary scheme of a further embodiment of the cyclisation process of preparing a multiple ring compound using a cyclic chiral acetal initiator.

As an illustrative example, where the initiator is (4S,6S)-4,6-dimethyl-2-phenyl-1,3-dioxane or [4S-(2α,4α,5β)]-4,5-dimethyl-2-phenyl-1,3-dioxolane, the reaction can be represented by the scheme depicted in FIG. 16. In such embodiments the 1,2,3,4,4a,9,10,10a-octahydro-1,1-dimethyl-4-a-(methyl)-2-phenanthren-derivative (2) is obtained in high yields. As an example, if $R^5$, $R^6$, $R^8$ and $R^9$ are methyl and $R^1$ is phenyl, the reaction yields the products depicted in the scheme of FIG. 18A.

Figure 21:
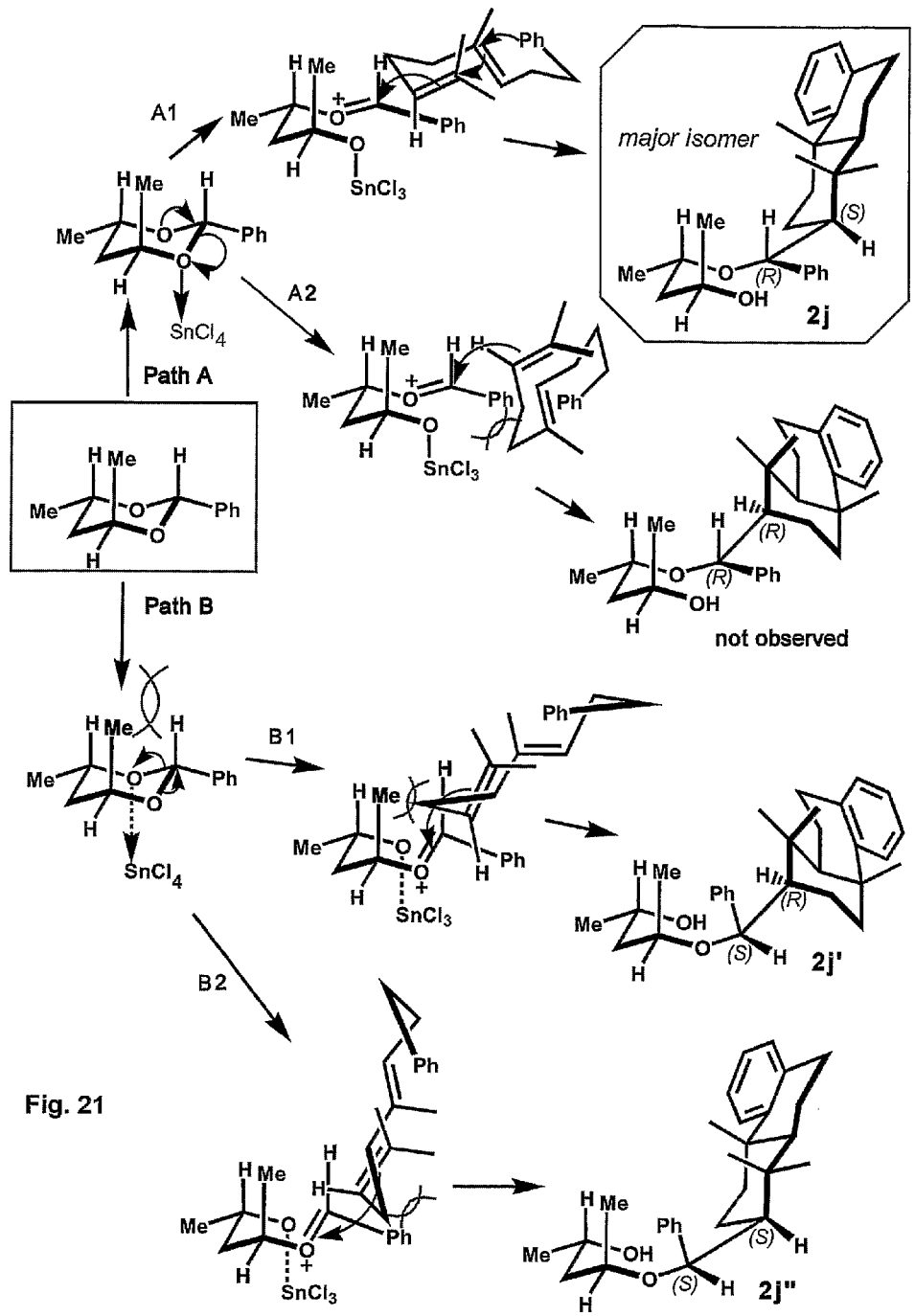
FIG. 21 depicts a scheme indicating the reaction paths matching the observed stereochemical product yields. The scheme is expected to be applicable to the reaction of cyclic acetals only (as depicted). Path A1 leads to the main product (2j).

Without wishing to be bound by theory, it is assumed that at least for the use of a catalyst in form of a Lewis acid the stereochemical product yields (see the appending Figures for examples) observed when using the method of the present invention are based on the reaction paths set out in the scheme of FIG. 21.

The Lewis acid (in this example $SnCl_4$)-assisted acetal ring opening can proceed via path A or B. Ring opening through path A eliminates the pre-existing axial stereorepulsion in the cyclic acetal and hence is more favourable. The resulting oxonium ion is subsequently attacked on the less hindered $R^e$ face by the polyene via antiperiplanar, open chain transition states (path A1 and A2). The transition state leading from path A1 is presumed to be much less sterically demanding and lower in energy compared to that from path A2, thereby affording the major isomer (2j) as determined by X-ray analysis. Cyclisations proceeding through equally unfavourable paths B1 and B2 provided minor isomers (2j') and (2j") respectively.

As noted above, in some embodiments the acetal initiator induces enantioselectivity in the intramolecular cyclisation reaction of the cyclisation process of the present invention. Asymmetric induction is in particular observed in embodiments where the acetal initiator includes more than one chiral centre. As an illustrative example, as already explained above, a cyclisation reaction of a reactant such as compound (1) (see e.g. FIG. 1A) always results in the formation of a trans-decalin system. In some embodiments where the acetal initiator is a cyclic acetal, for example an acetal initiator as depicted in FIG. 16 or FIG. 18 or formulas (IX), (X) or (XI) above, the configuration of the acetal ring may determine the enantiomer produced in the cyclisation reaction. It may for example affect the enantiomer produced, whether the ring carbon atom of acetal (7) carrying moiety $R^9$ (see e.g. FIG. 16) is part of a chiral centre with (R) or with (S)-configuration.

In some embodiments, where the acetal initiator is a cyclic acetal, the stereochemistry of the acetal ring may determine the enantiomer produced in the cyclisation reaction. In some embodiments, including embodiments where the acetal initiator is a cyclic acetal, the stereochemistry of a moiety covalently bound to the carbonyl carbon of the acetal may determine the enantiomer produced in the cyclisation reaction. As an illustrative example, in embodiments where the acetal initiator is of formulas (IX), (X) or (XI) (see above), $R^1$ of the acetal initiator may induce enantioselectivity of the cyclisation reaction. In some embodiments only $R^1$ of the acetal initiator induces the respective enantioselectivity. As an illustrative example, the acetal initiator may be a 3-oxo-9β-pregn-4-ene-20α-carboxaldehyde acetal, i.e. $R^1$ of the acetal initiator=

Figure 25A:
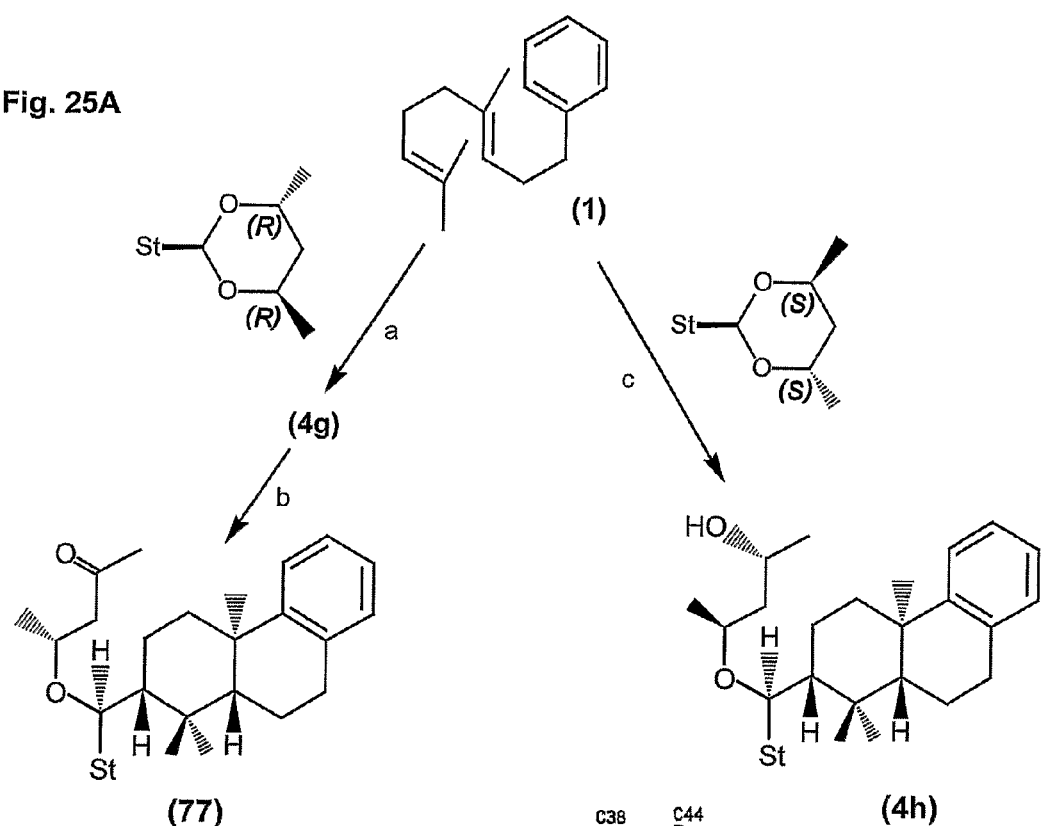
FIG. 25A depicts the asymmetric induction in a cyclisation process using isoprenoid compound (1). The chirality of steroid aldehyde and not the acetal ring determined the cyclisation stereochemistry.

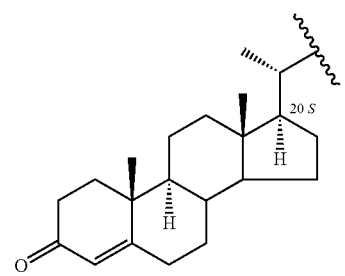

as depicted in FIG. 25A. As can be taken from the examples depicted in FIG. 25A and FIG. 26A, only the stereochemistry of this moiety ($R^1$) determined the enantioselectivity of the cyclisation reaction, while the stereochemistry of two other chiral centres of the acetal ring did not show an effect on the enantiomer of the cyclisation product produced. Acetal rings with inverse chirality in this regard yielded the same cyclisation product. As can be taken from FIG. 25A and FIG. 26A, the stereochemistry at position 4a and 10a of a respective tetra-decahydro-/octahydro-phenanthren ring system remains unaffected by the stereochemistry of the chiral centres of the acetal ring. In this regard also the stereochemistry of a moiety covalently bound to another carbon of the acetal ring of an acetal initiator may determine the enantiomer produced in the cyclisation reaction. Furthermore, in such embodiments $R^1$ of the acetal initiator may also induce enantioselectivity of the addition to the double bond of the isoprenoid unit, i.e. the formation of a covalent bond between the acetal initiator and the isoprenoid unit (cf. also FIG. 25A).

As can be inferred from the above, the initiator undergoes an addition reaction with the isoprenoid compound in the process of the present invention. Although any molar ratio of isoprenoid compound and initiator may be used in the method of the invention, it may be desired in some embodiments to use it in equimolar amounts to the isoprenoid compound or higher, in particular if it is desired to obtain a uniform product composition as illustrated above. The initiator may for example be used in the same molar amount, twice the molar amount or three times the molar amount of the isoprenoid compound. It is however also possible to use the isoprenoid compound in a molar excess relative to the initiator (the acetal). This can, for example, be considered if the acetal is available only in small amounts or at a high price and should thus react almost quantatively. Accordingly, in some embodiments the molar ratio of isoprenoid compound to acetal is in the range from about 1:10 to about 10:1, such as for example in the range from about 1:3 to about 3:1. The catalyst, e.g. an acid (see above) may be used in any desired molar amount (in relation to the isoprenoid compound), as long as the cyclisation reaction of the invention is not prevented. In some embodiments of the invention only catalytic amounts of the Lewis acid are added. In other embodiments equimolar amounts to the isoprenoid compound or higher are used, such as the same molar amount, twice the molar amount or three times the molar amount of the isoprenoid compound.

Figure 22:
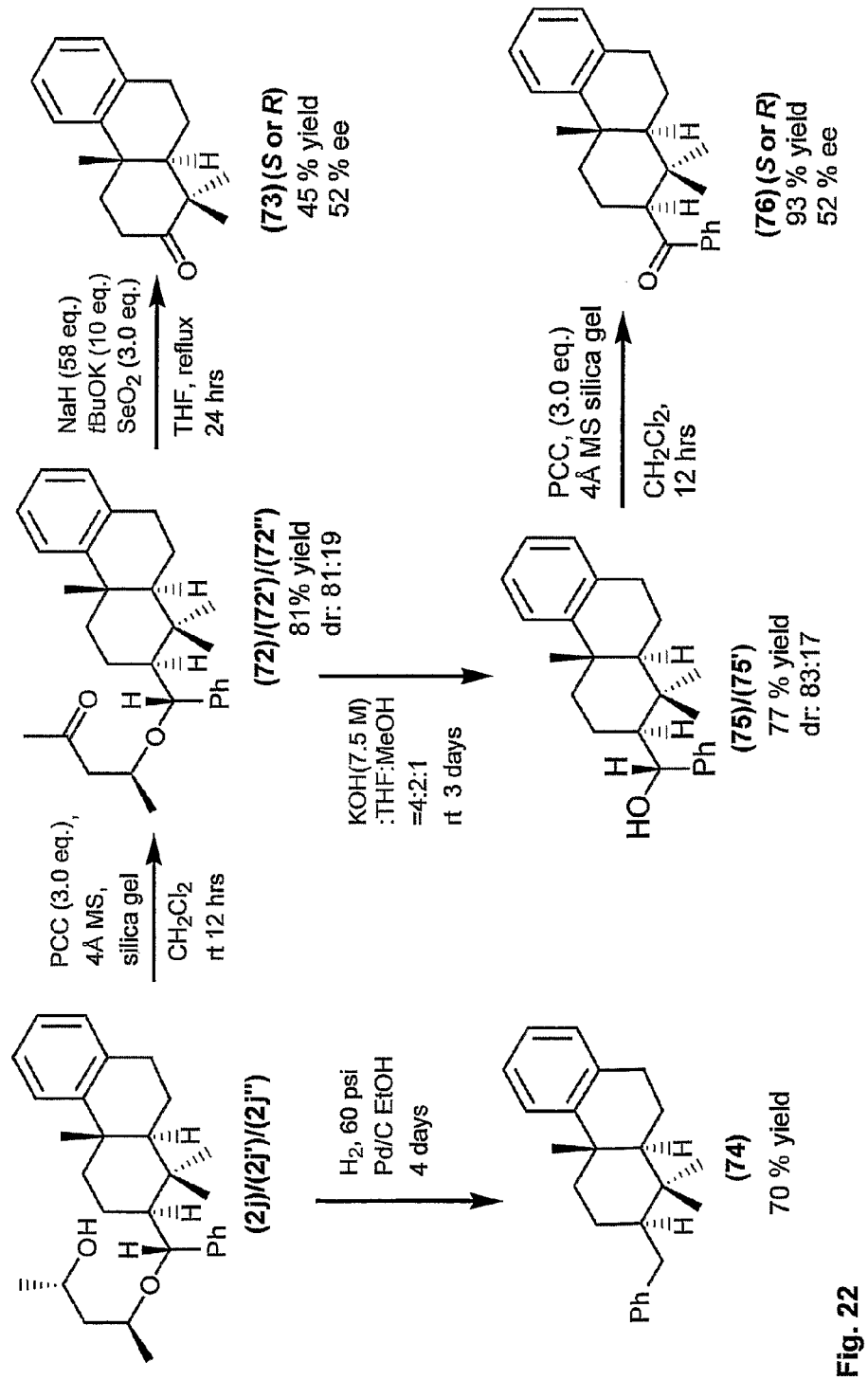
FIG. 22 shows the further functionalisation of compound (2j) (see FIG. 18B).

The process of the invention may include or be followed by various modification reactions. Examples include the partial or complete reduction of unsaturated bonds, a dihydroxylation of unsaturated carbon-carbon bonds, a monohalogenation of unsaturated carbon-carbon bonds, an oxidation of unsaturated carbon-carbon bonds to ketones by organic hydro peroxides in the presence of water and a metal catalyst, an epoxidation of unsaturated carbon-carbon bonds, a hydrosilylation of unsaturated carbon-carbon bonds, as well as reactions of functional groups in the obtained terpenoid compound. As a further illustrative example, a hydroxy group may be oxidised to a keto group or respectively to an aldehyde using chromic acid or pyridinium chlorochromate (PCC). Acetal-initiated cyclisation products are very versatile and can easily be converted into various optically-active tricyclic terpene compounds. As an illustrative example, the steroid (73), (4a-trans)-3,4,4a,9,10,10a-hexahydro-1,1-dimethyl-4-a-(methyl-d3)-2(1H)-phenanthrenone, as depicted in FIG. 22, which has been widely used in the synthesis of steroid derivatives, can conveniently be obtained using a process according to the present invention (see FIG. 22). Further examples illustrating the manifold synthetic avenues opened by the cyclisation process of the present invention can be taken from the appended figures (e.g. FIG. 8 or FIG. 9).

The listing or discussion of a previously published document in this specification should not necessarily be taken as an acknowledgment that the document is part of the state of the art or is common general knowledge. All documents listed are hereby incorporated herein by reference in their entirety.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the appending claims. In addition, where features or aspects of the invention are described in terms of Markush groups, those skilled in the art will recognise that the invention is also thereby described in terms of any individual member or subgroup of members of the Markush group.

The invention will be further illustrated with reference to the following non limiting examples.

Exemplary Embodiments of the Invention

Exemplary embodiments of processes according to the invention as well as reactants and further processes that may be used are shown in the appending Figures.

FIG. 1A shows an exemplary scheme of an embodiment of the cyclisation process of preparing a multiple ring compound. The cyclisation process of this example includes contacting 0.1 mmol (3E)-4,8-dimethyl-1-phenyl-nona-3,7-diene (1) (at a concentration of 0.05 M) in dichloromethane (2 mL) with an acetal initiator (0.3 mmol) in the presence of 0.2 mmol (added at 1.0 M in dichloromethane) of the Lewis acid catalyst Tin(IV) chloride. SnCl$_4$ was added to the reaction mixture at −78° C. after compound (1) and acetal were mixed in dichloromethane at room temperature. The intramolecular cyclisation reaction was allowed to proceed for 30 min. While in theory the cyclisation reaction may terminate after the formation of one ring (compound [3]), in practice compound (2) was formed in high yield. FIG. 1B shows a table summarising the obtained products using various acetals. The cyclisation of compound (1) in the presence of benzaldehyde dimethyl acetal for instance resulted in the formation of the 1,2,3,4,4a,9,10,10a-octahydro-1,1-dimethyl-4-a-(methyl)-2-phenanthren-derivative (2a) in a yield of 87% (see entry 1). [a)] Isomers diastereomeric at the benzylic CH were obtained for (2) in ratios from 80:20 to 100:0. [c)] Combined yield. [d)] Determined by $^1$H NMR.

FIG. 2A shows an exemplary scheme of a cyclisation process of preparing a multiple ring compound. The cyclisation process of this example includes contacting 0.1 mmol (3E)-4,8-dimethyl-1-phenyl-nona-3,7-diene (1) with acetal initiator (12) (0.2 mmol) and the lewis acid catalyst SnCl$_4$ (0.2 mmol, 1.0 M in CH$_2$Cl$_2$) in dichloromethane (2 mL) at −78° C. SnCl$_4$ was added to the reaction mixture at −78° C. after (1) and acetal were mixed in dichloromethane at room temperature. Reactions were allowed to proceed for 30 min, unless stated otherwise. FIG. 2B shows a table summarising the obtained yields using various moieties R$^1$ of the acetal initiator (12). Para bromo benzaldehyde acetal provided the same selectivity as benzaldehyde acetal and even better yield (see entries 2 and 1, products (4b) and (4a)). Screening of different acetals showed that both aromatic and aliphatic acetals were equally suitable as initiators (entries 3, 4 and 5). Asymmetric cyclisation using of a chiral (steroidal, "St", representing a 20-methyl-pregn-4-en-3-one-moiety) oxygen acetal as the initiator (entry 6) showed good selectivity (87:11:2) for the three observed isomers with an overall yield of 80%. An extended reaction time proved advantageous for the reaction using this initiator, and an exposure time of 24 hrs was selected for the cyclisation depicted in entry 6.

FIG. 3 shows exemplary reactions of a cyclisation process of preparing a multiple ring compound using an isoprenoid compound that includes an OH-group in its terminating moiety. Methods used included contacting 0.1 mmol isoprenoid compound (trans-Nerolidol (13), Chemical Abstracts-No 40716-66-3, and Geranylacetol (16), Chemical Abstracts-No 7733-91-7) with the respective acetal initiator (0.2 mmol) and the lewis acid catalyst SnCl$_4$ (0.2 mmol, 1.0 M in CH$_2$Cl$_2$) in dichloromethane (2 mL) at −78° C. SnCl$_4$ was added to the reaction mixture at −78° C. after the isoprenoid compound and the acetal initiator were mixed in dichloromethane at room temperature. For the asymmetric induction of the acetal initiator (45,65)-4,6-dimethyl-2-phenyl-1,3-dioxane see also FIG. 18. The present examples illustrate that the presence of a hydroxy group (with free valence electrons at the oxygen atom) at a suitable position may lead to the inclusion of the respective oxygen atom into a six-membered ring in form of an ether-bond. It is noted that using one enantiomer of the isoprenoid compound, such as (S)-(+)-trans-Nerolidol, results in the formation of one product enantiomer at the allylic alcohol chiral center (see e.g. the right hand side of the structure of compounds (14) and (15)). If mixture of isomers is used, the multiple ring compound is a mixture of both isomers.

FIG. 4 shows exemplary reactions of a cyclisation process of preparing a multiple ring compound using an isoprenoid compound that includes a C=C double bond in its terminating moiety. Cyclisation reactions using (E,E)-3,7,11-trimethyl-2,6,10-dodecatrien-1-ol propanoate (18) (Chemical Abstracts-No 104857-55-8) were performed as for FIG. 3.

FIG. 5 shows exemplary reactions of a cyclisation process of preparing a multiple ring compound using an isoprenoid compound that includes a keto group in its terminating moiety. Cyclisation reactions using trans-farnesylacetone (23) (Chemical Abstracts-No 1117-52-8) and trans-Geranylacetone (26) (Chemical Abstracts-No 3796-70-1) were performed as for FIG. 3. For the asymmetric induction of the acetal initiator (4S,6S)-4,6-dimethyl-2-phenyl-1,3-dioxane see also FIG. 18.

FIG. 6 shows exemplary reactions of a cyclisation process of preparing a multiple ring compound using an isoprenoid compound that includes a C≡C triple bond in its terminating moiety. Cyclisation reactions using (E)-6,10-dimethyl-5,9-undecadien-1-yne (29) (Chemical Abstracts-No 22850-55-1), (E)-7,1'-dimethyl-6,10-dodecadien-2-yne (32) (see below for its preparation), (E)-(6,10-dimethyl-5,9-undecadien-1-ynyl)trimethyl-silane (35) (Chemical Abstracts-No 72039-

82-8) and (E,E)-6,10,14-trimethyl-5,9,13-pentadecatrien-1-yne (38) (Chemical Abstracts-No 140677-79-8) were performed as for FIG. 3.

FIG. 7 shows exemplary reactions of a cyclisation process using a derivative of (3E)-4,8-dimethyl-1-phenyl-nona-3,7-diene (1), bearing a protected hydroxy group at position 1 (i.e. $R^4$ in general formula (IV)=$CH_2OH$). Cyclisation reactions using (E)-9-(3-bromophenyl)-2,6-dimethyl-2,6-nonadienyl]-1-oxy-(tert.-butyl)diphenyl-silane (41) and (E)-9-phenyl-2,6-dimethyl-2,6-nonadienyl]-1-oxy-(tert.-butyl)dimethyl-silane (43) (see below for their preparation) were performed as for FIG. 3.

Figure 8:
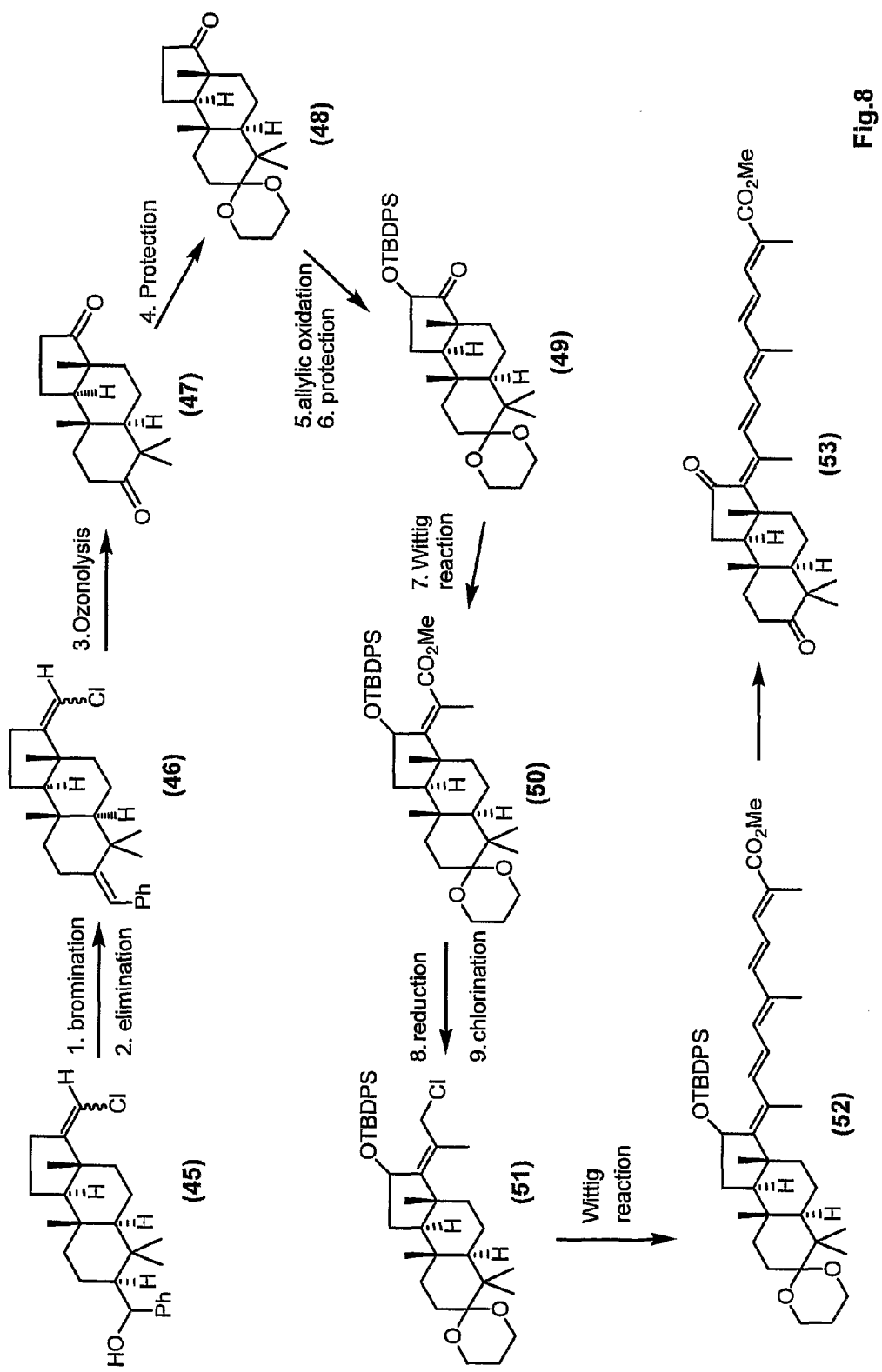
FIG. 8 depicts an exemplary synthesis scheme of Malabricane derivative (53), using a cyclisation process according to the present invention.

FIG. 8 depicts a contemplated synthesis scheme of Malabricane derivative (53) ((2E,4E,6E,8E,10Z)-10-[(3aR,5aR,9aR,9bR)-dodecahydro-3a,6,6,9a-tetramethyl-2,7-dioxo-3H-benz[e]inden-3-ylidene]-2,6-dimethyl-2,4,6,8-undecatetraenoic acid methyl ester), using a cyclisation process according to the present invention. Malabricane triterpenes, which posses antibacterial and anticancer properties and are thus valuable compounds, are inter alia found in the wood of the tree *Ailanthus malabrica*, the roots of the Mediterranean weed *Pyrethrum Santolinoides* and the sponge *Jaspis stellifera* of the Great Barrier Reef and reefs at Fiji (for the isolation of respective Malabricane derivatives see e.g. Sontag, W, et. al., *Eur. J. Org. Chem.* (1999) 1, 255-260; Jakupovic, J., et al., *Phytochemistry* (1987) 26, 5, 1536-1538; Ziegler, H. L., et. al., *J. Nat. Prod.* (2002) 65, 1764-1768; Ravi, B. N., et al., *J. Org. Chem.* (1981) 46, 1998-2001). The (7-dodecahydro-3a,6,6,9a-tetramethyl-3-chloromethylidenbenzindenyl)-α-benzyl alcohol isomer (45) was obtained from compound (39) or (40), depicted in FIG. 6. The reaction scheme used corresponded to the synthetic route 1-2j-72-75 depicted in FIG. 22.

Figure 9:
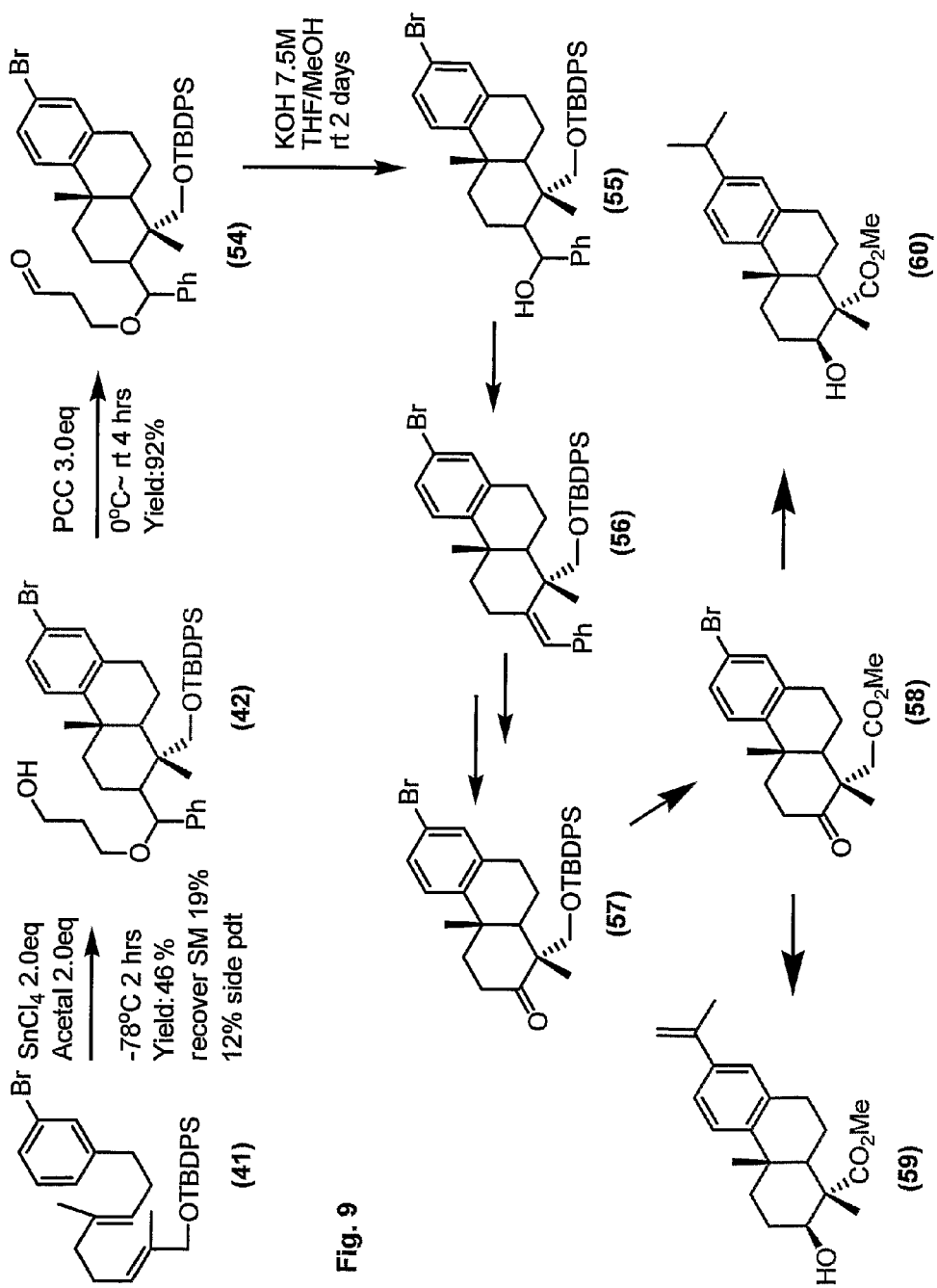
FIG. 9 depicts an exemplary synthesis scheme of the dehydroabietic acid derivatives (59) and (60), using a cyclisation process according to the present invention.

FIG. 9 depicts an exemplary synthesis scheme of the dehydroabietic acid derivatives (59) (3β-ol-8,11,13(14),15-abietatetraen 18-oic acid methyl ester, Chemical Abstracts-No 77091-13-5) and (60) (3β-ol-8,11,13(14)-abietatetraen 18-oic acid methyl ester, Chemical Abstracts-No 17751-30-3), using a cyclisation process according to the present invention (for the isolation of compound (60) and derivatives see e.g. Ulubelen, A. & Miski, M., *J. Nat. Prod.* (1981) 44, 119-124; Burnell, R. H. et al *J. Nat. Prod.* (1993) 56, 4, 461-472). Compounds (59) and (60) are key precursors for preparation of ring C aromatic steroids (including gestagens such as progesterone analogues, androgens, glucoorticoid and mineralcorticoid hormone analogues), which have been proved showing interesting pharmacological properties (see, for example, Abad, A., et al., *J. Org. Chem.* (1988) 53, 3761-3765). These two compounds could so far only be synthesised by means of the fungus *Corticium sakii* (Brannon, D. R., et al., *J. Org. Chem.* (1968) 33, 12, 4462-4466). The synthesis scheme based on the method of the present invention starts with the cyclisation of (E)-9-(3-bromophenyl)-2,6-dimethyl-2,6-nonadienyl]-1-oxy-(tert.-butyl)diphenyl-silane (41) using $SnCl_4$ at −78° C. as indicated for FIG. 3. Oxidation of the obtained (2R,4R)-4-((R)-((1R,2S,4aS,10aR)-7-bromo-1,4-a-dimethyl-1-(tert.-butyl)diphenyl-siloxymethyl-1,2,3,4,4a,9,10,10a-octahydro-phenanthren-2-yl)(phenyl)methoxy)propan-3-ol (42) with pyridinium chlorochromate (PCC) yielded 3-(((1S,2S,4aS,10aR)-7-bromo-1-((tert-butyldiphenylsilyloxy)methyl)-1,4-a-dimethyl-1,2,3,4,4a,9,10,10a-octahydrophenanthren-2-yl)(phenyl)methoxy)propanal (54). Hydrolysis using potassium hydroxide then yielded ((1S,2S,4aS,10aR)-7-bromo-1-((tert-butyldiphenylsilyloxy)methyl)-1,4-a-dimethyl-1,2,3,4,4a,9,10,10a-octahydrophenanthren-2-yl)(phenyl)methanol (55). Subsequent elimination, oxidative cleavage and reduction of the obtained product will result in the formation of compounds 59 and 60. The reaction scheme that may be employed for this synthesis corresponds to the synthetic route 1-2j-72-75 depicted in FIG. 22.

FIG. 10 depicts examples of isoprenoid compounds that may be used in the method of the present invention. A: (E,E)-12-(3-methoxyphenyl)-5,6,9-trimethyl-5,9-dodecadienoic acid (Chemical Abstracts-No. 54062-75-8); B: (4E,8E,12E,16E)-5,9,13,17,21-pentamethyl-4,8,12,16,20-docosapentaen-1-amine (CAS-No. 883561-20-4); C: (2Z)-farnesylamine (CAS-No. 515846-16-9); D: (E,E)-2-(3-methoxyphenyl)-5,6,9-trimethyl-5,9-dodecadienal (CAS-No. 53311-19-6); E: 2,6,10,14,18-pentamethyl-22-oxo-2,6,10,14,18-tricosapentaenamide (CAS-No 105097-28-7, the respective N,N'-dimethylamide has CAS-No. 105097-22-1); F: (E,E)-2-[10-(3-methoxyphenyl)-3,4,7-trimethyl-3,7-decadienyl]-3-methyl-2-cyclopenten-1-one (CAS-No. 54182-09-1); G: (E,E)-5,9,13-trimethyl-4,8,12-tetradecatriene-1-thiol (CAS-No. 162132-08-3); H: (4E,8E,12E,16E)-5,9,13,17,21-pentamethyl-4,8,12,16,20-docosapentaen-1-ol (Chemical Abstracts-No 883561-16-8); I: (E)-9-ethenyl-2,6-dimethyl-2,6-dodecadiene (CAS-No. 162897-12-3); J: 10-ethylidene-2,6,14-trimethyl-2,6,13-pentadecatriene (CAS-No. 18495-19-7); K: (all-E)-2,6,10,14,18,22-hexamethyl-2,6,10,14,18,22-tetracosahexaene-1,24-diol (CAS-No. 70854-61-4); L: (all-E)-19-hydroxy-6,10,14,18-tetramethyl-5,9,13,17-nonadecatetraen-2-one (CAS-No. 109862-65-9); M: (Z,E,E,E)-3,7,11,15,19-pentamethyl-2,6,10,14,18-eicosapentaenoic acid (CAS-No. 142695-71-4); N: (E,E,E)-2,6,10-trimethyl-2,6,10-pentadecatrien-14-yn-1-ol (CAS-No. 104465-89-6); O: (all-E)-2,6,10,15,19,23-hexamethyl-2,6,10,14,18,22-tetracosahexaen-1-ol (CAS-No. 79370-71-1); P: (E,E)-4,5,8,9-tetramethyl-1,12-diphenyl-4,8-dodecadiene-1,12-dione (CAS-No. 54960-87-1); Q: (E,Z,E)-6-(hydroxymethyl)-2,10-dimethyl-2,6,10-dodecatriene-1,12-diol (CAS-No. 126621-32-7); R: α-(2,6-dimethyl-1,5-heptadienyl)-2-cyclohexene-1-methanol (CAS-No. 159214-82-1); S: Aurachin B [2-methyl-4-(3,7,1-trimethyl-2,6,10-dodecatrienyl)-3-quinolinol1-oxide] (Chemical Abstracts-No 108354-12-7); T: (E)-9-[3,4-dimethoxy-5-(1-methylethyl)phenyl]-2,6-dimethyl-3-(1-methylethylidene)-6-nonen-2-ol (CAS-No. 83569-80-6). It may be advantageous in some cases to use protective moieties to shield functional groups of reactants, using standard methods well known in the art.

Figure 11:
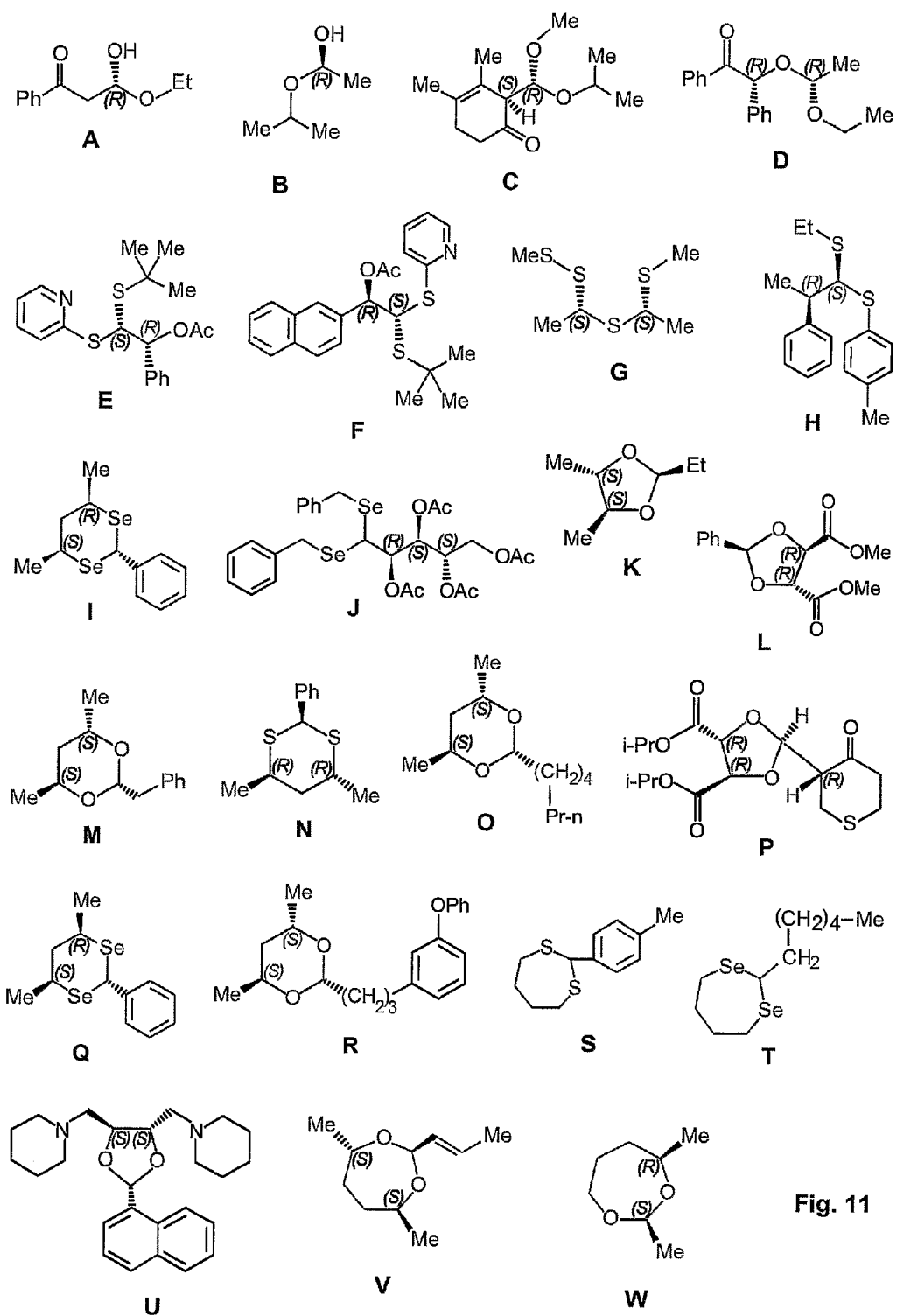
FIG. 11 depicts illustrative examples of acetal initiators that may be used in the process of the present invention.

FIG. 11 depicts examples of acetal initiators that may be used in the method of the present invention. A: (3R)-3-ethoxy-3-hydroxy-1-phenyl-1-propanone (Chemical Abstracts-No. 916462-71-0); B: (1R)-1-(1-methylethoxy)-ethanol (CAS-No. 500198-18-5); C: (R*,S*)-2-[methoxy(1-methylethoxy)methyl]-3,4-dimethyl-3-cyclohexen-1-one (CAS-No. 58431-44-0); D: [R—(R*,R*)]-2-(1-ethoxyethoxy)-1,2-diphenyl-ethanone (CAS-No. 133187-15-2); E: (αR)-α-[(S)-[(1,1-dimethylethyl)thio](2-pyridinylthio)methyl]-benzene-methanol acetate (CAS-No. 676328-67-9); F: (αR)-α-[(S)-[(1,1-dimethylethyl)thio](2-pyridinylthio)methyl]-2-naphthalenemethanol acetate (CAS-No. 676328-69-1); G: (R*,R*)-methyl 1-[[1-(methylthio)ethyl]thio]ethyl disulfide (CAS-No. 69318-93-0); H: ([S—(R*,S*)]-1-[[1-(ethylthio)-2-phenylpropyl]thio]-4-methyl-benzene, (CAS-No. 161265-13-0); I: (2α,4β,6β)-4,6-dimethyl-2-phenyl-1,3-diselenane (CAS-No. 177186-89-9); J: bis(phenylmethyl) diselenoacetal L-arabinose tetraacetate (CAS-No. 65784-59-0); K: [4S-(2α,4α,5β)]-2-ethyl-4,5-dimethyl-1,3-dioxolane (CAS-No. 122045-49-2); L: [4R-(2α,4α,5β)]-2-phenyl-1,3-dioxolane-4,5-dicarboxylic acid dimethyl ester (CAS-No. 38270-72-3); M: [4S-(2α,4α,6β)]-4,6-dimethyl-2-(phenylmethyl)-1,3-dioxane (CAS-No. 141271-06-9); N: (2α,4α,6β)-4,6-dimethyl-2-phenyl-1,3-dithiane (CAS-No. 60325-

70-4); O: [4S-(2α,4α,6β)]-2-heptyl-4,6-dimethyl-1,3-dioxane (CAS-No. 138842-38-3); P: (4R,5R)-2-[(3R)-tetrahydro-4-oxo-2H-thiopyran-3-yl]-1,3-dioxolane-4,5-dicarboxylic acid bis(1-methylethyl)ester (CAS-No. 649721-38-0); Q: (2α,4β,6β)-4,6-dimethyl-2-phenyl-1,3-diselenane (CAS-No. 177186-89-9); R: (2α,4α,6β)-4,6-dimethyl-2-[3-(3-phenoxyphenyl)propyl]-1,3-dioxane (CAS-No. 177186-89-9); S: 2-(4-methylphenyl)-1,3-dithiepane (CAS-No. 162246-35-7); T: 2-hexyl-1,3-diselenepane (CAS-No. 103971-78-4); U: [4S-(2α,4α,5β)]-1,1'-[[2-(1-naphthalenyl)-1,3-dioxolane-4,5-diyl]bis(methylene)]bis-piperidine (CAS-No. 104869-81-0); V: [2α(E),4α,6β]-4,7-dimethyl-2-(1-propenyl)-1,3-dioxepane (CAS-No. 186254-68-2); and W: cis-2,4-dimethyl-1,3-dioxepane (CAS-No. 54417-72-0).

Figures 12A, 12B:
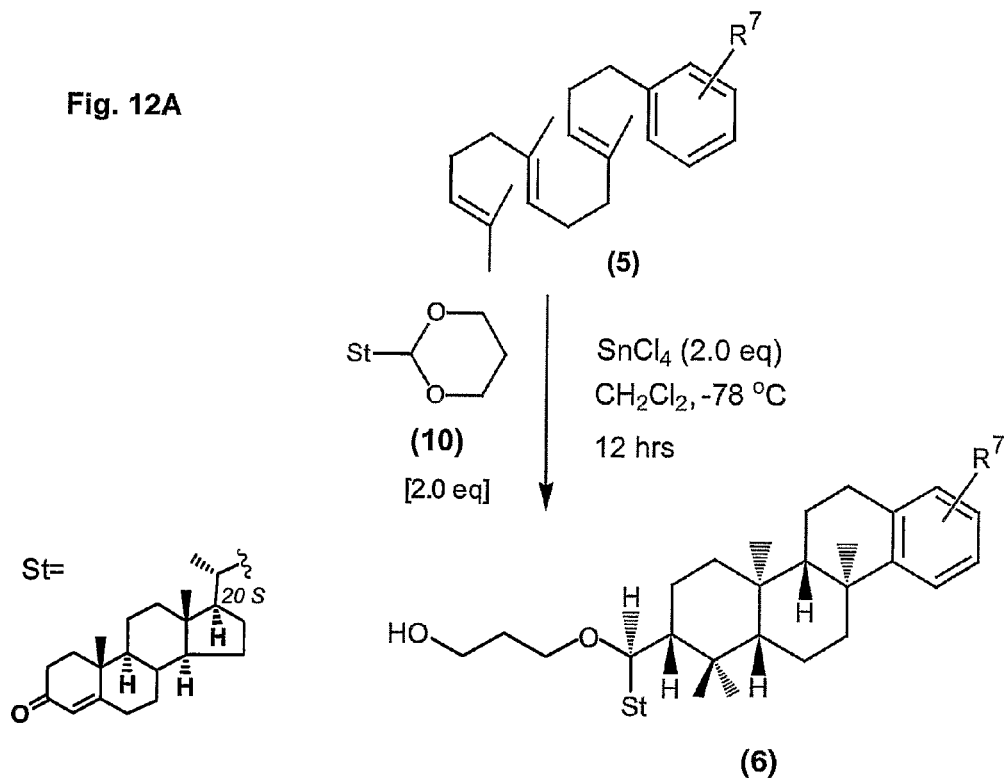
FIG. 12A depicts a scheme of a cyclisation process of preparing a multiple ring compound using a 3-oxo-9β-pregn-4-ene-20α-carboxaldehyde acetal as the initiator.
FIG. 12B shows a table summarising the obtained products using various isoprenoid compounds.

FIG. 12A depicts a further exemplary scheme of a cyclisation process of preparing a multiple ring compound. The abbreviation "St" (steroidal) represents a 20-methyl-pregn-4-en-3-one-moiety. All reactions were performed with the respective [(3E,7E)-4,8,12-trimethyl-3,7,11-tridecatrienyl]-benzene derivative (compound 5) (0.1 mmol), the 3-oxo-9β-pregn-4-ene-20α-carboxaldehyde acetal (0.2 mmol) and SnCl$_4$ (0.2 mmol, 1.0 M in CH$_2$Cl$_2$) in dichloromethane (2 mL) at −78° C. unless otherwise stated. SnCl$_4$ was added to the reaction mixture at −78° C. after the [(3E,7E)-4,8,12-trimethyl-3,7,11-tridecatrienyl]-benzene derivative and the acetal initiator were mixed in dichloromethane at room temperature. The reaction was then stirred for 16 hrs at the same temperature before quenching with NaHCO$_3$ saturated solution. FIG. 12B shows a table summarising the obtained products using various [(3E,7E)-4,8,12-trimethyl-3,7,11-tridecatrienyl]-benzene derivatives (compound 5). The abbreviation d.r. stands for "diastereoisomer ratio". For entry 1 and 2, d.r. was reported as benzylic isomers' ratio based on $^1$H NMR integration of benzylic CH; for entry 3-5, ratio was determined by $^{13}$C NMR; for all steroid acetal initiated cyclization, products were converted to aldehyde via PCC oxidation, d.r. was represented by ratio of CHO peak on $^1$H NMR spectrum. The term "diastereoisomers" here refers to isomers with different relative configuration between the chiral center(s) on benzylic carbon and the three new chiral centers formed in the bicyclic skeleton. The three new chiral centers formed are considered as a chiral group (of fixed relative configuration within the group) based on the Stork-Eschenmoser postulate.

Figure 13:
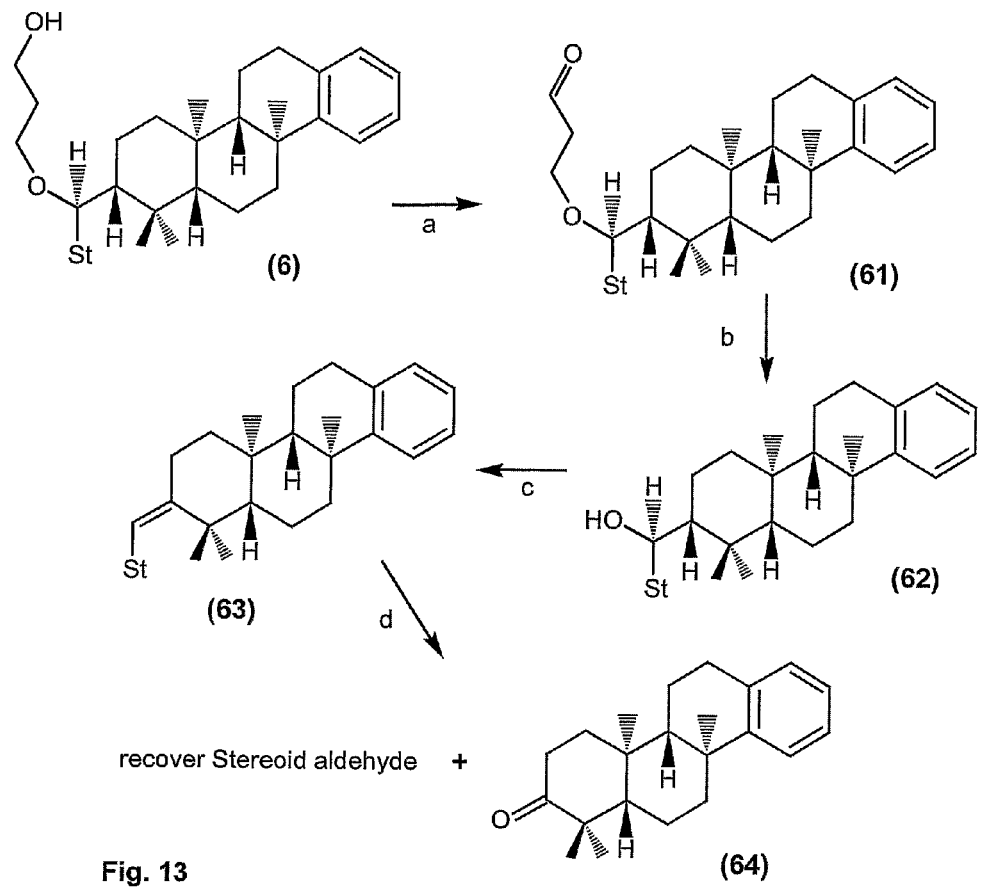
FIG. 13 illustrates the usability of an embodiment of the cyclisation process according to the present invention by means of an illustrative synthesis scheme.

FIG. 13 illustrates how products of an intermolecular acetal initiated cyclisation process according to the present invention can readily be modified to diverse cyclopolyprenoids and their analogues. step a=PCC 3.0 eq, 0° C. to room temperature, overnight, Yield: 78%, ratio: 66:18:10:6, step b=THF/MeOH/KOH (7.5 M)=4:2:1, 12 hrs, step c=1) MsCl, 2.0 eq, Et$_3$N 3.0 eq, 2) tBuOK 2.0 eq, THF, rt overnight, d=O$_3$, −78° C.

FIG. 14 depicts the reaction scheme of an exemplary cyclisation process that may be carried out using a [(3E,7E,11E)-4,8,12,16-tetramethyl-3,7,11,15-hepta-decatetraenyl]-benzene derivative (compound 65). The obtainable respective multiple ring compound (compound 65) has a pentacyclic ring system.

FIG. 15A shows an exemplary scheme of a cyclisation process of preparing a multiple ring compound using chiral acetal templates. All reactions were performed with (3E)-4,8-dimethyl-1-phenyl-nona-3,7-diene (1) (0.1 mmol), acetal initiator (0.3 mmol) and SnCl$_4$ (0.2 mmol, 1.0 M in CH$_2$Cl$_2$) in dichloromethane (2 mL) at −78° C. unless otherwise stated. SnCl$_4$ was added to the reaction mixture at −78° C. after (1) and acetal were mixed in dichloromethane at room temperature. The reaction was then stirred for 16 hrs at the same temperature before quenching with NaHCO$_3$ saturated solution. R* corresponds to the respective opened form of the former acetal. FIG. 15B depicts examples of the (combined) yields obtained with two exemplary acetals under the indicated conditions. $^a$ Isomers diastereomeric at the benzylic CH were obtained for both 2 and 2' in ratios from 80:20 to 100:0. $^b$ Combined yield. $^c$ Determined by $^1$H NMR. dr=diastereoisomer ratio reported as major benzylic isomer of (2):major benzylic isomer of (2').

FIG. 16 depicts an exemplary scheme of a cyclisation process of preparing a multiple ring compound using as chiral acetal initiators an in 1- and 3-position a heteroatom containing 4,6-dimethyl-cyclohexane derivative (compound 7) or an in 1- and 3-position a heteroatom containing 4,5-dimethyl-cyclopentane derivative (compound 8). Four possible product isomers (2 to 2''') can theoretically be expected.

FIG. 17 illustrates the preparation of exemplary chiral acetal initiators. Trimethylsilyl trifluoromethanesulfonate was added to a mixture of the aldehyde and the trimethylsilylethers of the respective diol at −78° C. Aldehydes used were benzaldehyde (compound 67) and 3-oxo-9β-pregn-4-ene-20α-carboxaldehyde (compound 71). Trimethylsilylethers used were 2,2,4,6,8,8-hexamethyl-3,7-dioxa-2,8-disilanonane (compound 68), 2,2,4,5,7,7-hexamethyl-3,6-dioxa-2,7-disilaoctane, (compound 69), and 2,2,4,6,8,8-hexamethyl-3,7-dioxa-2,8-disilanonane (compound 70).

Figures 18A, 18B:
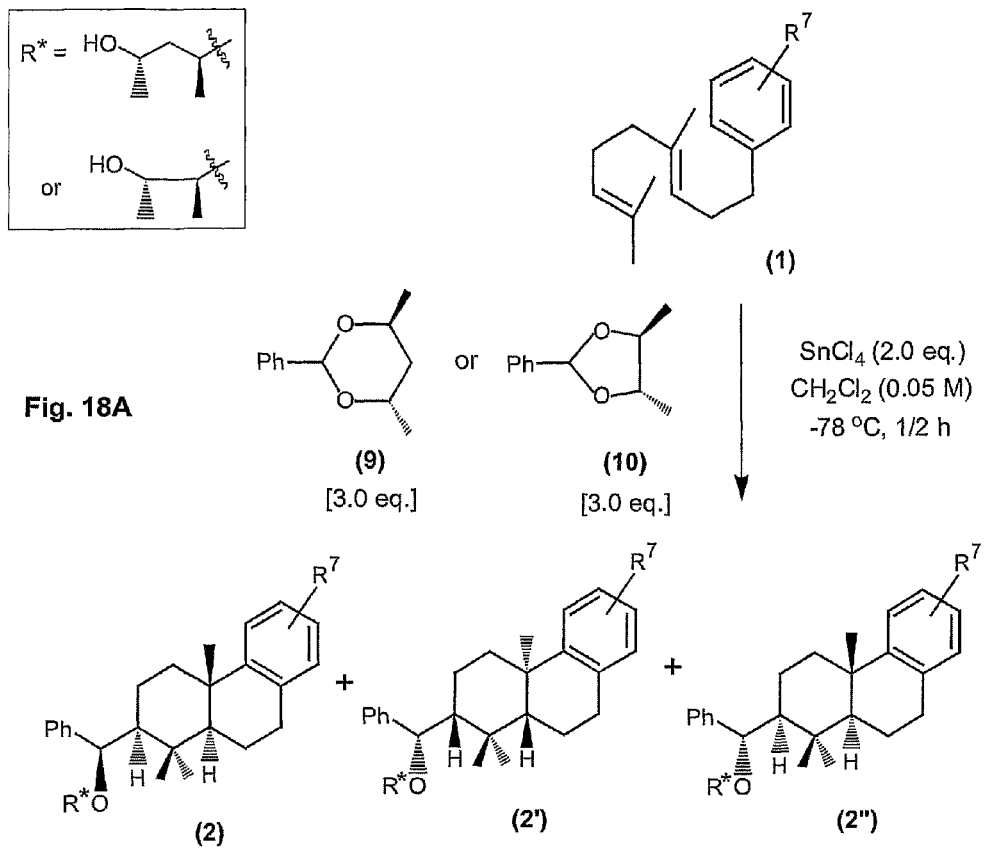
FIG. 18A shows an exemplary scheme of a cyclisation process of preparing a multiple ring compound using embodiments of the chiral acetal initiators of FIG. 16.
FIG. 18B shows a table summarising the obtained products using various isoprenoid compounds.

FIG. 18A shows an exemplary scheme of a cyclisation process of preparing a multiple ring compound using embodiments of the chiral acetal initiators of FIG. 16 (see also FIG. 17). Reactions were carried out as indicated for FIG. 15. R* corresponds to the respective opened form of the former acetal. The fourth isomer that can theoretically be expected (inverse stereochemistry at the benzylic carbon center in (2'), cf. FIG. 16) was only observed in one product mixture in trace amounts and is thus not shown. FIG. 18B depicts examples of the products and respective yields obtained with (4S,6S)-4,6-dimethyl-2-phenyl-1,3-dioxane (9) or [4S-(2α,4α,5β)]-4,5-dimethyl-2-phenyl-1,3-dioxolane (10) using various benzene-substituted isoprenoid compounds. Theoretically 4 isomers can be expected. The fourth isomer not depicted in FIG. 18A (cf. FIG. 16) was however only observed for the reaction corresponding to entry 1. For ease of view this isomer has therefore not been further considered and only added to entry 1 for sake of completeness. $^{a)}$ Combined yield. $^{b)}$ The fourth possible isomeric product was not detected by $^1$H NMR except entry 1. $^{c)}$ Determined by $^1$H NMR. $^{d)}$ d.r.=diastereoisomer ratio, reported as (2+2'':2'). Major isomer 2j is believed to have the same absolute ring stereo configuration compared to 2j''. $^{e)}$ Side products 75/75' (see FIG. 22) were obtained in 25% yield.$^{f)}$ Product with benzene ring cyclised at meta position to OMe was obtained in 15% yield as well.

Figure 19:
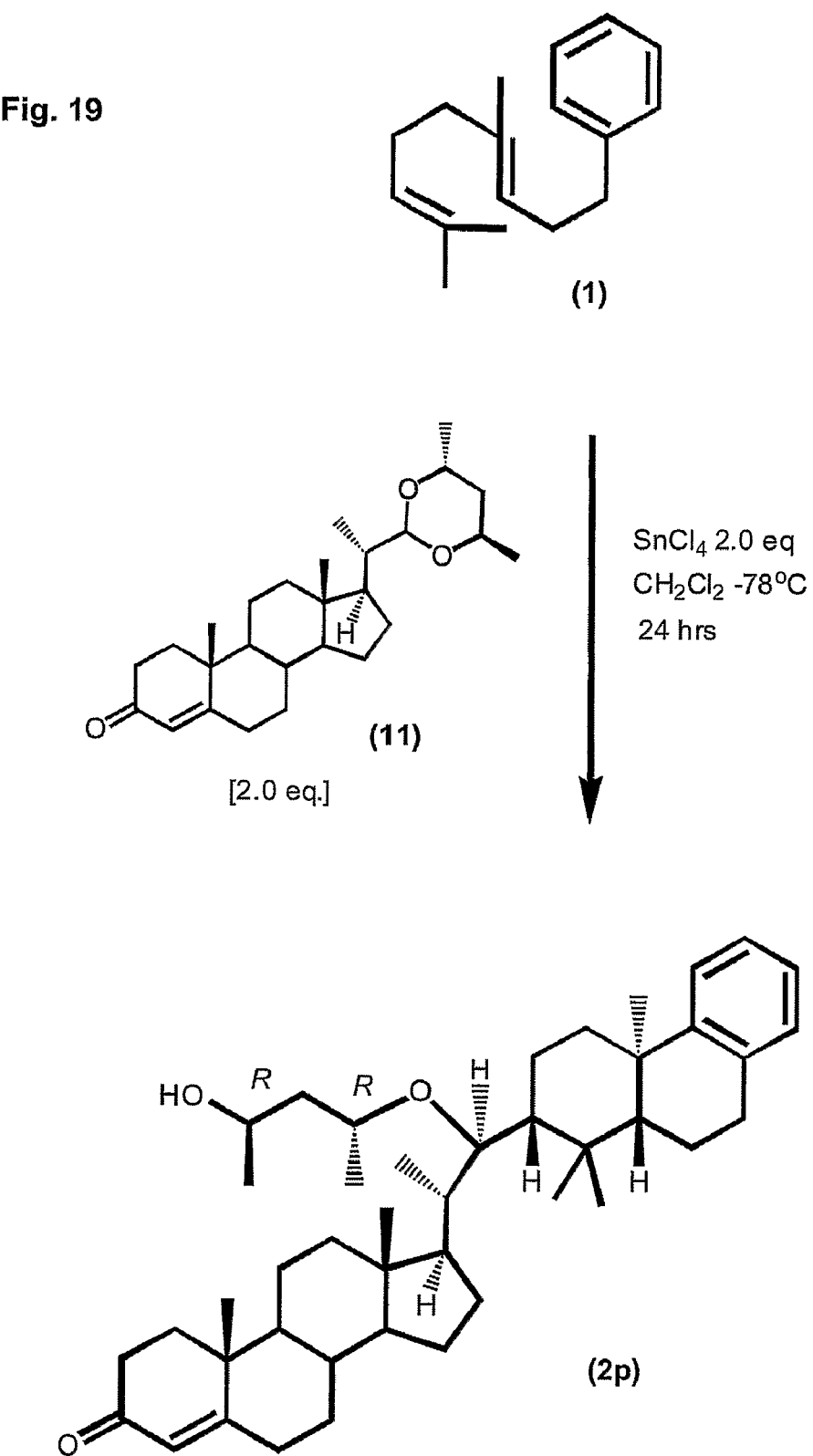
FIG. 19 depicts an example of the cyclisation process according to the present invention, for a major product of which the absolute stereochemistry has been determined via X-ray crystallography.

FIG. 19 depicts an example of a cyclisation process according to the present invention. The present inventors have determined the absolute stereochemistry of a major product of the reaction of trans-2,6-dimethyl-9-phenyl-2,6-nonadiene (1) using the initiator 3-oxo-pregn-4-ene-20-carboxaldehyde cyclic 20-(2,4-pentanediyl acetal), via X-ray crystallography with a crystal of the cyclisation product.

Figure 20A:
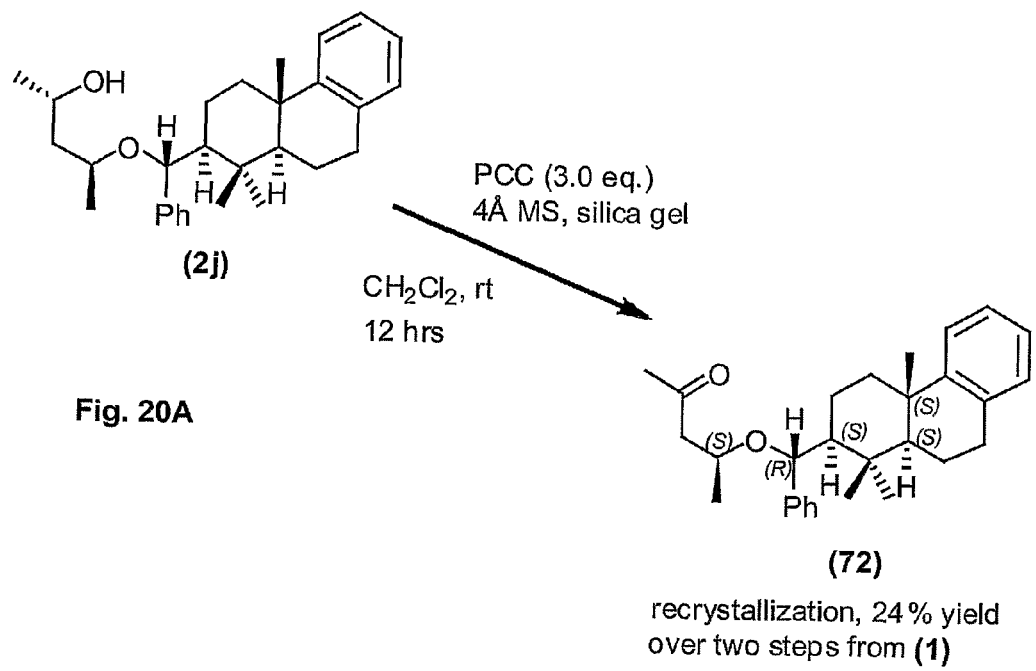
FIG. 20A depicts the oxidation of compound (2j) (see FIG. 18B) for the determination of its absolute stereochemistry by X-Ray crystallography analysis.
Figure 20B:
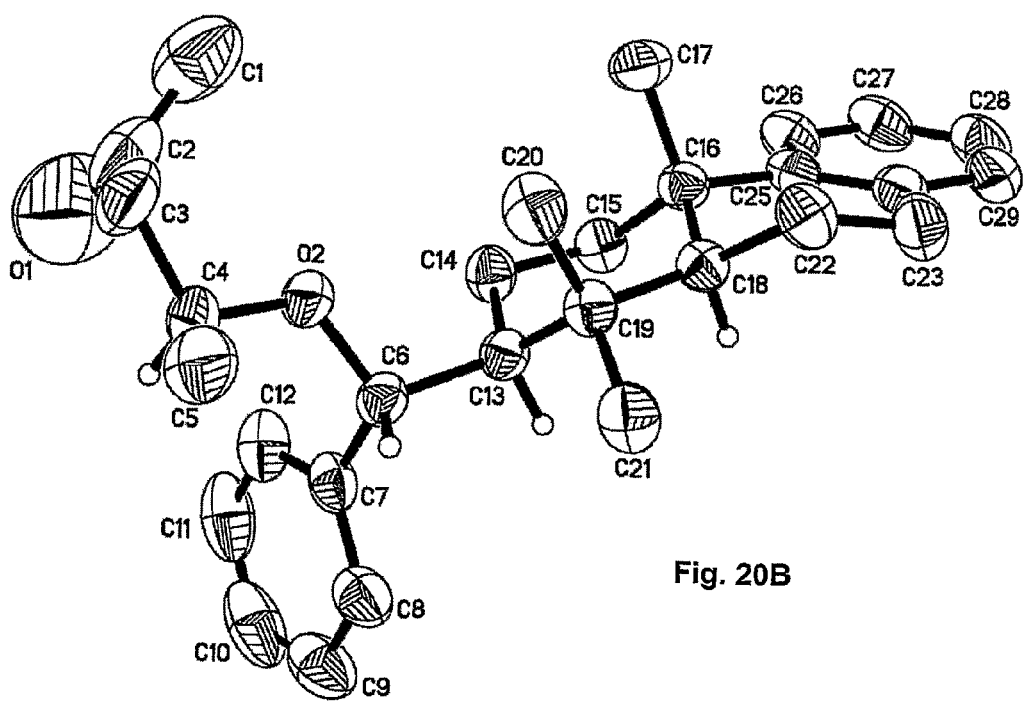
FIG. 20B shows the obtained representation structure of (72).

FIG. 20A depicts an oxidation of a multiple ring compound obtained by a cyclisation process (see FIG. 18B). The absolute stereochemistry of the major isomer (2j) (see FIG. 18B) was determined by X-Ray crystallography analysis of the corresponding ketone derivative (72). PCC oxidation of cyclisation product mixture (2j)/(2j')/(2j'') followed by recrystallisation of the corresponding ketone mixture gave the major isomer (72) in overall 24% yield. The X-ray crystal structure (the crystal size was 0.45×0.15×0.10 mm³) showed the depicted absolute stereochemistry of (72) (S (template), R (benzyl), S (ring). The representation structures of (72) and assignment of stereochemistry are depicted in FIG. 20B.

The stereochemistry of the other minor isomers was confirmed by chiral HPLC (see also FIG. 27 & FIG. 28), ¹H NMR and ¹³C NMR analyses after converting (2) to (73) (FIG. 22). The conversion of (2j)/(2j')/(2j") to (4a-trans)-3,4,4a,9,10,10a-hexahydro-1,1-dimethyl-4-a-(methyl-d3)-2(1H)-phenanthrenone (73) or compound (76) (see FIG. 22) gave a mixture of isomers in an enantiomeric ratio of 76 (S):24 (R), which is in agreement with our stereochemical observation. Therefore, the absolute configuration of (2j") must be S (template), S (benzyl), S (ring). The three new chiral centers formed are considered as a chiral group, of fixed relative configuration within the group, based on the Stork-Eschenmoser postulate.

FIG. 21 depicts a scheme indicating the reaction paths that would be in line with the observed stereochemical product yields at the reaction centre of the addition of the acetal. The scheme is expected to be applicable to the reaction of cyclic acetals only (as depicted). General path A is believed to be favourable due to the elimination of axial stereorepulsion in the cyclic acetal. Compound (2j) is the major isomer formed as the respective transition state is thought to be sterically favoured.

FIG. 22 depicts the functionalisation of cyclization products obtained using the method of the invention to various terpenes. Oxidation of (2R,4R)-4-((R)-phenyl((2S,4aS,10aS)-1,1,4a-trimethyl-1,2,3,4,4a,9,10,10a-octahydrophenanthren-2-yl)-methoxy)pentan-2-ol (compound 2j) with pyridinium chlorochromate (PCC) yielded (R)-4-((R)-phenyl((2S,4aS,10aS)-1,1,4a-trimethyl-1,2,3,4,4a,9,10,10a-octahydrophenanthren-2-yl)methoxy)pentan-2-one (compound 72). Subsequent resulted in the formation of (4aS,10aR)-1,1,4a-trimethyl-4,4a,10,10a-tetrahydrophenanthren-2(1H,3H,9H)-one (compound 73). Cleavage to (4aS,10aR)-1,1,4a-trimethyl-4,4a,10,10a-tetrahydrophenanthren-2(1H,3H,9H)-one (compound 73) was carried out using sodium hydride and selenium dioxide. (2R,4R)-4-((R)-phenyl((2S,4aS,10aS)-1,1,4a-trimethyl-1,2,3,4,4a,9,10,10a-octahydrophenanthren-2-yl)methoxy)pentan-2-ol (compound 2j) was converted to (2R,4aS,10aS)-2-benzyl-1,1,4a-trimethyl-1,2,3,4,4a,9,10,10a-octahydrophenanthrene (compound 74) by hydrogenation on a Pd/C catalyst. The stereochemistry of compound 74 was confirmed by X-ray analysis after crystallisation (see FIG. 23). (R)-4-((R)-phenyl((2S,4aS,10aS)-1,1,4a-trimethyl-1,2,3,4,4a,9,10,10a-octahydrophenanthren-2-yl)methoxy)pentan-2-one (compound 72) hydrolysed to (R)-phenyl((2S,4aS,10aS)-1,1,4a-trimethyl-1,2,3,4,4a,9,10,10a-octahydrophenanthren-2-yl)methanol (compound 75/75') using potassium hydroxide. Subsequent oxidation with pyridinium chlorochromate yielded phenyl((2S,4aS,10aS)-1,1,4a-trimethyl-1,2,3,4,4a,9,10,10a-octahydrophenanthren-2-yl)methanone (compound 76).

Figure 23:
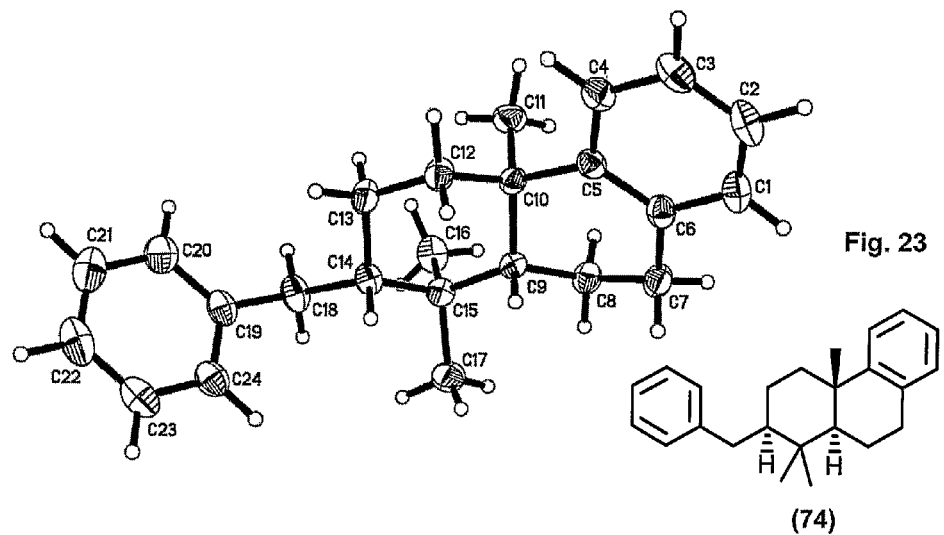
FIG. 23 shows the three-dimension structure of compound 74 as obtained by X-ray crystallography.

FIG. 23 depicts representation structure of X-Ray crystallography data of (2R,4aS,10aS)-2-benzyl-1,1,4a-trimethyl-1,2,3,4,4a,9,10,10a-octahydrophenanthrene (compound 74) obtained by further functionalisation of compound 2j, which was obtained using the method of the present invention (compare FIG. 22). The crystal size was 0.30×0.30×0.20 mm³.

Figure 24:
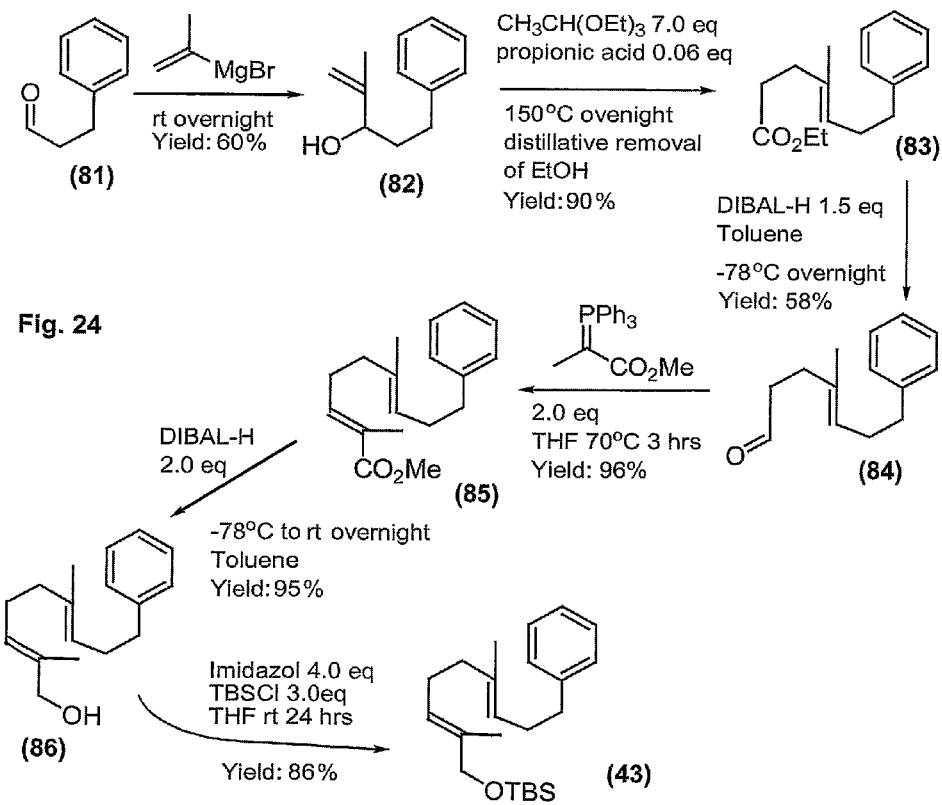
FIG. 24 depicts the preparation of compound (43) from hydrocinnamaldehyde (81).

FIG. 24 depicts the preparation of (E)-9-phenyl-2,6-dimethyl-2,6-nonadienyl]-1-oxy-(tert.-butyl)dimethyl-silane (compound 43). In a coupling reaction hydrocinnamaldehyde (81) was converted to 2-methyl-5-phenyl-1-penten-3-ol (compound 82, CAS-No. 1836-38-0), from which (E)-4-methyl-7-phenyl-4-heptenoic acid ethyl ester (compound 83, CAS-No. 76620-37-6) was obtained. Reduction yielded (4E)-4-methyl-7-phenyl-4-heptenal (compound 84, CAS-No. 238736-71-5), which was transformed to (E)-2,6-dimethyl-9-phenyl-2,6-nonadienoic acid methyl ester (compound 85) in a Wittig-reaction using [1-(methoxycarbonyl)ethylidene]triphenylphosphorane (CAS-No. 2605-68-7). Reduction of compound (85) yielded (2E,6E)-2,6-dimethyl-9-phenyl-2,6-nonadien-1-ol (compound 86, CAS-No. 238736-72-6). Reaction with (tert.-butyl)dimethyl-silylchloride resulted in the formation of compound (43).

Figure 25B:
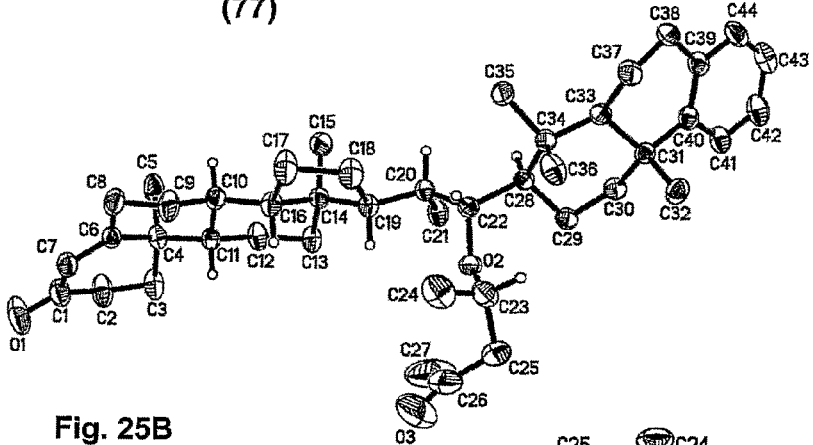
FIG. 25B and FIG. 25C show representation structures of the two products as obtained by X-ray crystallography.
Figure 25C:
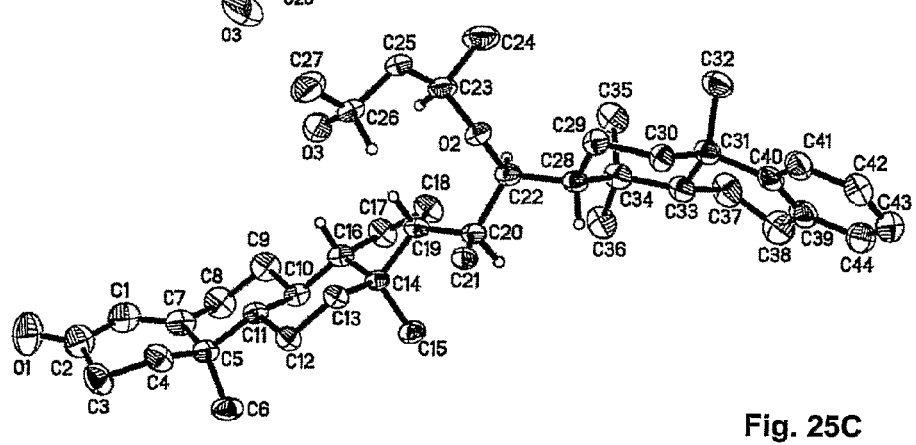

FIG. 25A depicts the importance of diol and aldehyde chirality in terms of asymmetric induction in a cyclisation process of the present invention. Two 3-oxo-pregn-4-ene-20-carboxaldehyde cyclic 20-2,4-pentanediyl acetals with reverse chirality of the alcohol in the acetal were used as initiators with the isoprenoid compound (3E)-4,8-dimethyl-1-phenyl-nona-3,7-diene (1). Cyclisation reaction (a) was carried out using SnCl₄ (2.0 eq), acetal (2.0 eq), −78° C. 16 hrs (yield: 85%). Oxidation reaction (b) was performed using PCC (3.0 eq), at 0° C. to room temperature, overnight (yield: 80%). Crystalisation was performed (yield: 48%), a representation structures is depicted in FIG. 25 B. Cyclisation reaction (c) was carried out using SnCl₄ (2.0 eq), acetal 2.0 eq, −78° C. 16 hrs (yield: 62%). Crystalisation was performed (yield: 50%), a representation structures is depicted in FIG. 25 C. Both acetal initiators yielded cyclisation products (4g) and (4h) with the same stereochemistry at the multiple ring compound. Thus it can be concluded that the chirality of steroid aldehyde dominated the cyclisation stereochemistry with ring fusion carbons bearing both R conformation.

FIG. 26A shows the scheme of a cyclisation process using the same acetals with reverse chirality as depicted in FIG. 25A with the longer chain polyene [(3E,7E)-4,8,12-trimethyl-3,7,11-tridecatrienyl]-benzene (compound 5). Cyclisation reaction (a) was carried out using SnCl₄ (2.0 eq), acetal (2.0 eq), −78° C. 16 hrs (yield: 45%). Oxidation reaction (b) was performed using PCC (3.0 eq), at 0° C. to rt, overnight. (yield: 56%); Crystallisation was performed (not shown). Cyclisation reaction (c) was carried out using SnCl₄ (2.0 eq), acetal (2.0 eq), −78° C. 16 hrs (yield: 50%) Oxidation reaction (d) was performed using PCC (3.0 eq), 0° C. to rt, overnight (yield: 55%, ratio). Crystallisation was performed (yield: 28%), a representation structures is depicted in FIG. 26B. The two obtained 2-substituted (4aS,4bR,10bR,12aS)-1,2,3,4,4a,4b,5,6,10b,11,12,12a-dodecahydro-1,1,4a,10b-tetramethylchrysene compounds (78a) and (78b) possessed the same stereochemistry at the multiple ring compound. Comparing X-Ray crystallography data of cyclization products' derivatives (78a) and (78b), newly constructed tetracyclic rings shared the same conformation for six chiral centres. This result is consistent with previous tricyclic systems and verified that the chiral environment of the steroid determined the chirality induction. Thus it is can be concluded that the stereochemistry of the cyclisation process of various compounds (5) as depicted e.g. in FIG. 12A is determined in the same way.

FIG. 27 shows two spectra obtained by chiral high pressure liquid chromatography analysis (chiral HPLC). FIG. 27A shows racemic (4aS,10aR)-1,1,4a-trimethyl-4,4a,10,10a-tetrahydrophenanthren-2(1H,3H,9H)-one (compound 73), which was used as a reference standard (ratio: 50:50). FIG. 27B shows the optical active compound 73 obtained using the method of the present invention. It can immediately be taken from the spectrum that the peak ratio of the optical compound is no longer 50:50.

FIG. 28 shows two spectra obtained by chiral high pressure liquid chromatography analysis (chiral HPLC). FIG. 28A shows racemic phenyl((2S,4aS,10aS)-1,1,4a-trimethyl-1,2, 3,4,4a,9,10,10a-octahydrophenanthren-2-yl)methanone (compound 76), which was used as a reference standard (ratio: 50:50). FIG. 27B shows the optical active compound 76 obtained using the method of the present invention. It can again immediately be spotted that the peak ratio of the optical compound is no longer 50:50.

EXAMPLES

The following examples illustrate the cyclisation process according to the present invention. In these examples, experiments involving moisture and/or air sensitive components were performed in oven-dried glassware. Commercial solvents and reagents were used without further purification with the following exceptions: THF was freshly distilled from sodium wire, $CH_2Cl_2$ was freshly distilled from $CaH_2$, and dried $Et_2O$ was taken from solvent purification system (PS-400-5, innovative technology Inc.). HPLC grade iso-propanol was used without further purification. Aldehydes were distilled before using.

Analytical thin layer chromatography (TLC) was performed using Merck 60 F254 precoated silica gel plate (0.2 mm thickness). Subsequent to elution, plates were visualized using UV radiation (254 nm) on Spectroline Model ENF-24061/F 254 nm. Further visualization was possible by staining with basic solution of potassium permanganate or acidic solution of ceric molybdate, followed by heating on a hot plate.

Flash chromatography was performed using Merck silica gel 60 with distilled solvents. Columns were typically packed as slurry and equilibrated with hexane prior to use.

Infrared spectra were recorded on a Shimadzu IR Prestige-21 FT-IR Spectrometer. Liquid samples were examined as film between NaCl or KBr salt plates.

Proton nuclear magnetic resonance ($^1$H NMR) and carbon nuclear magnetic resonance ($^{13}$C NMR) spectroscopy were performed on a Bruker Advance 300, 400 and 500 NMR spectrometers. Chemical shifts $^1$H NMR spectra are reported as in units of parts per million (ppm) downfield from $SiMe_4$ ($\delta$ 0.0) and relative to the signal of chloroform-d (J=7.264, singlet). Multiplicities were given as: s (singlet); d (doublet); t (triplet); q (quartet); dd (doublet of doublets); ddd (doublet of doublets of doublets); dddd (doublet of doublets of doublets of doublets); dt (doublet of triplets); m (multiplets) and etc. The number of protons (n) for a given resonance is indicated by nH. Coupling constants are reported as a J value in Hz. Carbon nuclear magnetic resonance spectra ($^{13}$C NMR) are reported as d in units of parts per million (ppm) downfield from $SiMe_4$ (d 0.0) and relative to the signal of chloroform-d (J=77.03, triplet). ee were determined by chiral HPLC analysis.

Low resolution mass spectrum analysis was performed on Finnigan polaris Q, GCMS XP mass spectrometer (Thermo Electron Corporation). High resolution mass spectral analysis (HRMS) was performed on Finnigan MAT 95 XP mass spectrometer (Thermo Electron Corporation).

X-Ray crystallography analysis was performed on Bruker X8 APEX X-Ray diffractometer.

Example 1

General Procedure for Preparation of Polyene 1a~1f

The procedure was following the method developed by Martin Demuth (Rosales, V., et al. *J. Org. Chem*. (2002), 67, 1167-1170). To an oven-dried 100 mL round-bottom flask with a magnetic stirring bar was added [(Ph3P)-4-Pd] (0.25 mmol, 5 mol %) and dry THF (20 mL). The solution was cooled to 0° C. prior to addition of allylic bromide (5.0 mmol, 1.0 eq.). The solution was stirred for 5 minutes and was treated with the Grignard reagent (7.5 mmol in 1.0M THF solution, 1.5 eq.). The reaction mixture was allowed to proceed at room temperature for another 24 hours before quenching with ice water 30 mL. The aqueous layer was extracted with diethyl ether (2×30 mL), and the combined organic extracts were washed with water (30 mL) and brine (30 mL) and dried over anhydrous sodium sulfate, filtered and concentrated in vacuo. The residual crude product was purified by column chromatography to afford the desired product.

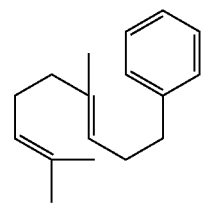

(E)-(4,8-Dimethylnona-3,7-dienyl)benzene (1): colourless oil, 86% yield.

$R_f$: 0.91 (Hexane:$Et_2O$=9:1)

$^1$H NMR (400 MHz, $CDCl_3$): 7.30-7.20 (m, 5H), 5.21 (tq, J=7.10, 1.15 Hz, 1H), 5.11 (tt J=6.77, 1.38 Hz, 1H), 2.66 (t, J=6.74 Hz, 2H), 2.34 (dt, J=7.74, 7.56 Hz, 2H), 2.08 (t, J=7.05, 6.55 Hz, 2H), 2.01 (t, J=7.05 Hz, 2H), 1.71 (s, 3H), 1.58 (s, 3H), 1.63 (s, 3H)

$^{13}$C NMR (100 MHz, $CDCl_3$): 142.45, 135.79, 131.36, 128.52, 128.24, 125.68. 124.39, 123.63, 39.76, 36.19, 30.00, 26.74, 25.74, 17.73, 15.99

HRMS (EI): m/z calculated for $C_{17}H_{24}$ [M]$^+$: 228.1878. Found: 228.1868.

FTIR (NaCl): ν 3085, 2923, 1653, 1604, 1496, 1453, 1376, 1108, 1030, 836, 746, 698 cm$^{-1}$

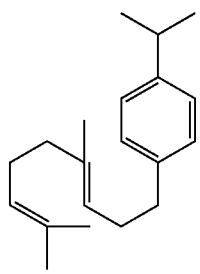

(E)-1-(4,8-Dimethylnona-3,7-dienyl)-4-isopropylbenzene (1k): colourless oil, 62% yield.

$R_f$: 0.91 (Hexane:$Et_2O$=9:1)

$^1$H NMR (400 MHz, $CDCl_3$): 7.16-7.12 (m, 4H), 5.20 (tq, J=6.93, 0.99 Hz, 1H), 5.10 (tt, J=6.93, 1.48 Hz, 1H), 2.89 (septet, J=6.93 Hz, 1H), 2.59 (t, J=7.60 Hz, 2H), 2.32-2.27 (m, 2H), 2.10-2.03 (m, 2H), 2.01-1.95 (m, 2H), 1.69 (s, 3H), 1.61 (s, 3H), 1.57 (s, 3H), 1.25 (d, J=6.94 Hz, 6H)

$^{13}$C NMR (100 MHz, $CDCl_3$): 146.17, 139.77, 135.62, 131.34, 128.36, 126.25, 124.39, 123.81, 39.73, 35.72, 33.71, 30.37, 26.73, 25.73, 24.10, 17.71, 15.99

HRMS (EI): m/z calculated for $C_{20}H_{30}$ [M]$^+$: 270.2348. Found: 270.2348.

FTIR (KBr): ν 3446, 2960, 2868, 1716, 1512, 1450, 1381, 1107, 1055, 1018, 821, 576 cm$^{-1}$

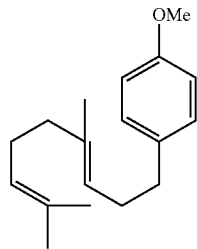
1l (E)-1-(4,8-Dimethylnona-3,7-dienyl)-4-methoxybenzene (1l): colourless oil, 65% yield.

$R_f$: 0.91 (Hexane:Et$_2$O=9:1)

$^1$H NMR (400 MHz, CDCl$_3$): 7.14-7.11 (m, 2H), 6.85-6.33 (m, 2H), 5.19 (tq, J=6.93, 0.83 Hz, 1H), 5.11 (tt, J=6.77, 1.34 Hz, 1H), 3.80 (s, 3H), 2.60 (t, J=7.27 Hz, 2H), 2.32-2.26 (m, 2H), 2.11-2.26 (m, 2H), 2.02-2.06 (m, 2H), 1.71 (s, 3H), 1.63 (s, 3H), 1.58 (s, 3H)

$^{13}$C NMR (100 MHz, CDCl$_3$): 157.69, 135.69, 134.57, 131.33, 129.36, 124.39, 123.70, 113.64, 55.25, 39.75, 35.24, 30.23, 26.74, 25.74, 17.73, 16.00

HRMS (EI): m/z calculated for C$_{18}$H$_{26}$O [M]$^+$: 258.1984. Found: 258.1975.

FTIR (KBr): ν 2962, 2833, 1612, 1512, 1454, 1440, 1300, 1246, 1176, 1039, 821, 734 cm$^{-1}$

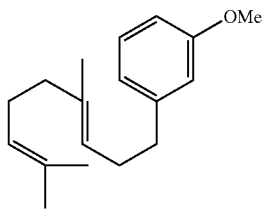
1m (E)-1-(4,8-Dimethylnona-3,7-dienyl)-3-methoxybenzene (1m): colourless oil, 65% yield.

$R_f$: 0.91 (Hexane:Et$_2$O=9:1)

$^1$H NMR (400 MHz, CDCl$_3$): 7.25-7.15 (m, 1H), 6.84-6.77 (m, 3H), 5.23 (tq, J=7.11, 1.16 Hz, 1H), 5.13 (tt, J=6.74, 1.15 Hz, 1H), 3.83 (s, 3H), 2.66 (t, J=7.43 Hz, 2H), 2.37-2.35 (m, 2H), 2.13-2.08 (m, 2H), 2.04-2.00 (m, 2H), 1.72 (s, 3H), 1.64 (s, 3H), 1.60 (s, 3H)

$^{13}$C NMR (100 MHz, CDCl$_3$): 159.60, 144.11, 135.80, 131.36, 129.19, 124.39, 123.62, 120.96, 114.27, 110.97, 55.12, 39.76, 36.22, 29.90, 26.77, 25.74, 17.73, 16.03

HRMS (EI): m/z calculated for C$_{18}$H$_{26}$O [M]$^+$: 258.1984. Found: 258.1976.

FTIR (KBr): ν 2920, 2833, 1600, 1578, 1489, 1454, 1436, 1261, 1151, 1045, 777, 694 cm$^{-1}$

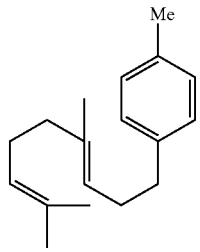
1n (E)-1-(4,8-Dimethylnona-3,7-dienyl)-4-methylbenzene (1n): colourless oil, 63% yield.

$R_f$: 0.91 (Hexane:Et$_2$O=9:1)

$^1$H NMR (400 MHz, CDCl$_3$): 7.13-7.11 (m, 4H), 5.24 (tq, J=6.13, 0.99 Hz, 1H), 5.16 (tt, J=6.27, 1.32 Hz, 1H), 2.65 (t, J=7.43 Hz, 2H), 2.37 (s, 3H), 2.34-2.31 (m, 2H), 2.14-2.07 (m, 2H), 2.05-2.02 (m, 2H), 1.66 (s, 3H), 1.64 (s, 3H), 1.52 (s, 3H)

$^{13}$C NMR (100 MHz, CDCl$_3$): 139.40, 135.66, 135.07, 131.34, 128.95, 128.39, 124.43, 123.80, 39.77, 35.77, 30.17, 26.77, 25.76, 21.06, 17.74, 16.03

HRMS (EI): m/z calculated for C$_{18}$H$_{26}$ [M]$^+$: 242.2035. Found: 242.2039.

FTIR (KBr): ν 2966, 2922, 2654, 1514, 1448, 1375, 806 cm$^{-1}$.

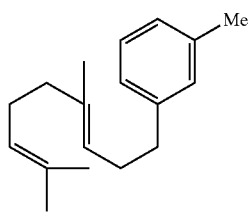
1o (E)-1-(4,8-Dimethylnona-3,7-dienyl)-3-methylbenzene (1o): colourless oil, 62% yield.

$R_f$: 0.91 (Hexane:Et$_2$O=9:1)

$^1$H NMR (400 MHz, CDCl$_3$): 7.23-7.19 (m, 1H), 7.05-7.03 (m, 3H), 5.24 (tq, J=6.77, 1.20 Hz, 1H), 5.14 (tt, J=7.93, 1.49 Hz, 1H), 2.64 (t, J=7.51 Hz, 2H), 2.37 (s, 3H), 2.37-2.31 (m, 2H), 2.14-2.09 (m, 2H), 2.05-2.01 (m, 2H), 1.74 (s, 3H), 1.65 (s, 3H), 1.62 (s, 3H)

$^{13}$C NMR (100 MHz, CDCl$_3$): 142.42, 137.74, 135.70, 131.36, 129.33, 128.16, 126.44, 125.50, 124.41, 123.76, 39.77, 36.14, 30.08, 26.80, 25.76, 21.46, 17.74, 16.02

HRMS (EI): m/z calculated for C$_{18}$H$_{26}$ [M]$^+$: 242.2035. Found: 242.2039.

FTIR (KBr): ν 2922, 1608, 1489, 448, 1375, 781, 698 cm$^{-1}$

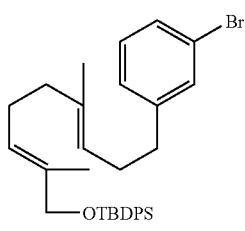
(41)

43

Preparation of polyene 41, (E)-9-(3-bromophenyl)-2,6-dimethyl-2,6-nonadienyl]-1-oxy-(tert.-butyl)diphenyl-silane

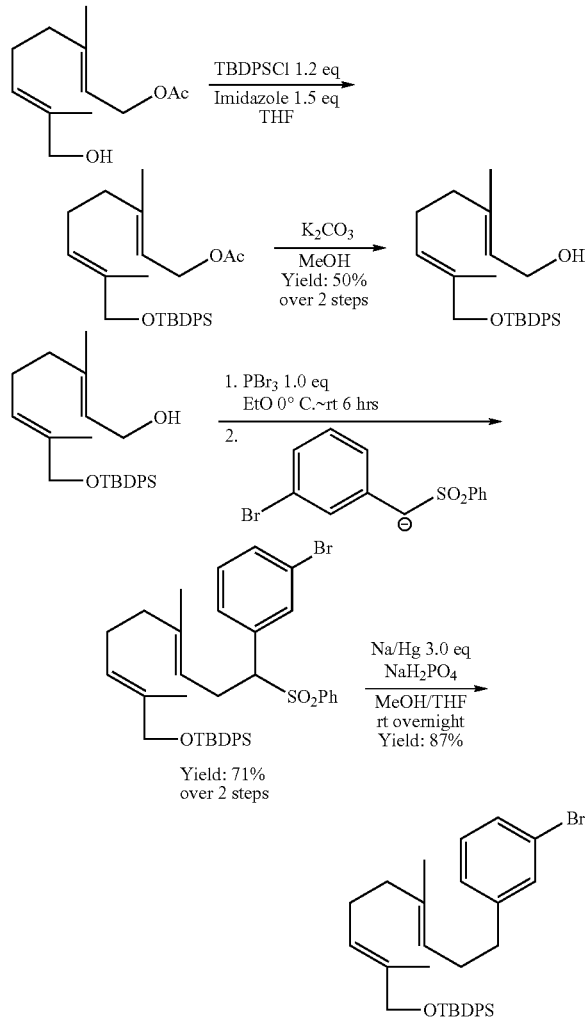

8-(E)-hydroxy geranyl acetate (1.0 mmol, 1.0 eq) was dissolved in THF together with imidazole (1.5 mmol, 1.5 eq) at room temperature. tert-butyl-diphenylsilylchloride, TBDPSCl (1.2 mmol, 1.2 eq) was added via a dry syringe. The reaction was allowed to proceed for 24 hours before quenching with water. The aqueous layer was extracted with dichloromethane (2×30 mL), and the combined organic extracts were washed with water (30 mL) and brine (30 mL) and dried over anhydrous sodium sulfate, filtered and concentrated in vacuo. The residual crude product was purified by column chromatography to afford the desired product.

The product was subject to MeOH and excess $K_2CO_3$. After 24 hours reaction at room temperature, it was quenched by adding water. The aqueous layer was extracted with dichloromethane (2×30 mL), and the combined organic extracts was washed with water (30 mL) and brine (30 mL) and dried over anhydrous sodium sulfate, filtered and concentrated in vacuo. The residual crude product was purified by column chromatography to afford the desired alcohol product 8-tert-butyl-diphenyl-silyloxy-3,7-dimethyl-2,6-octadien-1-ol.

44

The obtained alcohol (1.0 mmol, 1.0 eq) was dissolved in diethylether, $Et_2O$ and was cooled to 0° C., $PBr_3$ (1.0 mmol, 1.0 eq) was added via syringe. The reaction was quenched by pouring reaction mixture into $NaHCO_3$ saturated aqueous solution. The aqueous layer was extracted with $Et_2O$ (2×30 mL), and the combined organic extracts were washed with water (30 mL) and brine (30 mL) and dried over anhydrous sodium sulfate, filtered and concentrated in vacuo. The residual crude product was purified by column chromatography to afford the desired bromide product.

1-bromo-3-(phenylsulfonylmethyl)benzene (1.5 mmol, 1.5 eq) was dissolved in THF together with hexamethylphosphoramide (HMPA, 2.0 mmol, 2.0 eq) and the solution was cooled to −78° C., buthyllithium in Hexane (BuLi, 1.6 M in hexane, 2.0 mmol, 2.0 eq) was added via dry syringe. After 20 minutes, the (2E,6E)-8-(tert-butyldiphenylsilyloxy)geranyl bromide tetrahydrofuran (THF) solution was added via syringe at −78° C. The reaction was allowed to proceed 12 hours before quenching with $NH_4Cl$ saturated aqueous solution. The aqueous layer was extracted with dichloromethane (2×30 mL), and the combined organic extracts were washed with water (30 mL) and brine (30 mL) and dried over anhydrous sodium sulfate, filtered and concentrated in vacuo. The residual crude product was purified by column chromatography to afford the desired product (E)-9-(3-bromophenyl)-9-phenylsulphonyl-2,6-dimethyl-2,6-nonadienyl]-1-oxy-(tert.-butyl)diphenyl-silane.

The obtained sulfone (1.0 mmol, 1.0 eq) was dissolved in THF and MeOH solution. Na/Hg (20 mol %, 2.0 mmol, 2.0 eq) was added at 0° C. The reaction was allowed to proceed 12 hours before quenching with water. The aqueous layer was extracted with diethyl ether (2×30 mL), and the combined organic extracts were washed with water (30 mL) and brine (30 mL) and dried over anhydrous sodium sulfate, filtered and concentrated in vacuo. The residual crude product was purified by column chromatography to afford the desired product compound (41).

(43)

Preparation of polyene 43, (E)-9-phenyl-2,6-dimethyl-2,6-nonadienyl]-1-oxy-(tert-butyl)diphenyldimethyl-silane The synthesis route used in this example is shown schematically in FIG. 24 (see the appended figures). Hydrocinnamaldehyde (5.0 mmol, 1.0 eq, compound 81) in THF solution was subject to prop-1-en-2-ylmagnesium bromide (7.5 mmol, 1.5 eq) in THF solution at 0° C. The reaction was allowed to proceed 12 hours before quenching by pouring into water. The aqueous layer was extracted with dichloromethane (2×30 mL), and the combined organic extracts were washed with water (30 mL) and brine (30 mL), dried over anhydrous sodium sulfate, filtered and concentrated in vacuo. The residual crude product was purified by column chromatography to afford the desired allylic alcohol product 82.

The obtained 2-methyl-5-phenyl-1-penten-3-ol (5.0 mmol, 1.0 eq, compound 82) was subsequently mixed with triethyl orthoacetate (35.0 mmol, 7.0 eq) and catalytic amount of propionic acid (0.30 mmol, 0.06 eq) at room temperature. The mixture was refluxed at 150° C. for 12 hours, whereafter EtOH was distilled off from reaction mixture. The residual crude product was purified by column chromatography to afford the desired product ester 83.

(E)-4-methyl-7-phenyl-4-heptenoic acid ethyl ester (compound 83, 2.0 mmol, 1.0 eq.) was dissolved in toluene and cooled down to −78° C. Diisobutylaluminium hydride (DIBAL-H, 1.0 M in hexane, 3.0 mmol, 1.5 eq.) was added by means of a dry syringe. The reaction was allowed to proceed for 12 hours before quenching by adding MeOH at −78° C. A saturated aqueous solution of potassium sodium tartrate was added and warmed up to room temperature (rt). The aqueous layer was extracted with dichloromethane (2×30 mL), and the combined organic extracts were washed with water (30 mL) and brine (30 mL) and dried over anhydrous sodium sulfate, filtered and concentrated in vacuo. The residual crude product was purified by column chromatography to afford the desired product aldehyde 84.

The obtained (4E)-4-methyl-7-phenyl-4-heptenal (compound 84, 2.0 mmol, 1.0 eq) was mixed together with ylide (6.0 mmol, 3.0 eq) in THF. After refluxing for 4 hours, the solvent was removed in vacuo. The residual crude product was purified by column chromatography to afford (E)-2,6-dimethyl-9-phenyl-2,6-nonadienoic acid methyl ester (compound 85).

Ester 85 (2.0 mmol, 1.0 eq) was dissolved in toluene and cooled down to −78° C. Diisobutylaluminium hydride (DIBAL-H, 1.0 M in hexane, 4.0 mmol, 2.0 eq) was added by means of a dry syringe. The reaction was warmed up to room temperature and allowed to proceed for 12 hours before quenching by adding methanol at room temperature. Saturated potassium sodium tartrate aqueous solution was added and the mixture stirred for 1 hour. The aqueous layer was extracted with dichloromethane (2×30 mL), and the combined organic extracts were washed with water (30 mL) and brine (30 mL) and dried over anhydrous sodium sulfate, filtered and concentrated in vacuo. The residual crude product was purified by column chromatography to afford the desired product alcohol 86.

(2E,6E)-2,6-dimethyl-9-phenyl-2,6-nonadien-1-ol (compound 86, 1.0 mmol, 1.0 eq) was dissolved in THF together with imidazole (1.5 mmol, 1.5 eq) at room temperature. (tert.-butyl)dimethyl-silylchloride (TBSCl, 1.2 mmol, 1.2 eq) was added. The reaction was allowed to proceed for 24 hours before quenching with water. The aqueous layer was extracted with dichloromethane (2×30 mL), and the combined organic extracts were washed with water (30 mL) and brine (30 mL) and dried over anhydrous sodium sulfate, filtered and concentrated in vacuo. The residual crude product was purified by column chromatography to afford (E)-9-phenyl-2,6-dimethyl-2,6-nonadienyl]-1-oxy-(tert.-butyl)dimethyl-silane (compound 43).

Preparation of (E)-7,11-dimethyl-6,10-dodecadien-2-yne

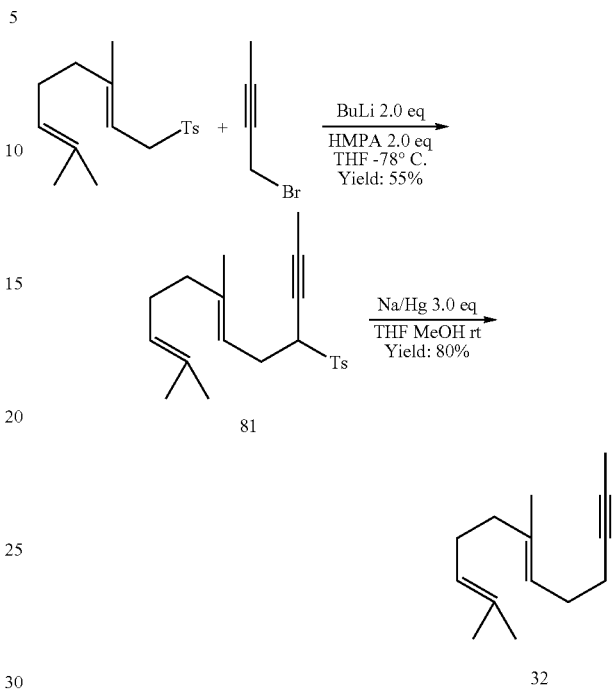

p-toluolsulfonyl-geraniol (0.1 mmol, 1.0 eq) and hexamethylphosphoramide (HMPA, 0.2 mmol, 2.0 eq) were dissolved in THF and cooled to −78° C. BuLi (0.2 mmol, 2.0 eq) was added. 2-Butynyl bromide (0.2 mmol, 2.0 eq) was then added by means of a dry syringe. The reaction was allowed to proceed 12 hours before quenching with NH₄Cl saturated aqueous solution. The aqueous layer was extracted with dichloromethane (2×30 mL), and the combined organic extracts were washed with water (30 mL) and brine (30 mL) and dried over anhydrous sodium sulfate, filtered and concentrated in vacuo. The residual crude product was purified by column chromatography to afford the desired product.

p-toluolsulfonyl-(E)-7,11-dimethyl-6,10-dodecadien-2-yn-4-ol (81) (0.1 mmol, 1.0 eq) was dissolved in THF and MeOH solution. Na/Hg (20 mol %, 0.3 mmol, 3.0 eq) was added. The reaction was allowed to proceed 12 hours before quenching with water. The aqueous layer was extracted with diethyl ether (2×30 mL), and the combined organic extracts were washed with water (30 mL) and brine (30 mL) and dried over anhydrous sodium sulfate, filtered and concentrated in vacuo. The residual crude product was purified by column chromatography to afford the desired product.

Example 2

Procedure for Preparation of Acetals

Acetals were synthesized according to the method developed by R. Noyori (Noyori, R., et al., *Tetrahedron Lett.* (1980) 21, 1357-1358) and modified method developed by Masaaki Kurihara (Kurihara, M., & Hakamata, W., *J. Org. Chem.* (2003) 68, 3413-3415). Chiral cyclic acetal was synthesis as following: To a solution of PhCHO (1.0 mmol 1.0 eq.) in CH$_2$Cl$_2$ (5 mL) was added (TMSO)$_2$R (1.0 mmol, 1.0 eq.). The reaction mixture was cooled to −78° C. prior to addition of TMSOTf (0.05 mmol, 0.05 eq.). The reaction was allowed to proceed at −78° C. for overnight before quenching with pyridine (2 mL). The mixture was diluted with CH$_2$Cl$_2$ (30 mL), washed with water (20 mL) and brine (20 mL), and dried over anhydrous Na$_2$SO$_4$, filtered and concentrated in vacuo. The residual crude product was purified by flash column chromatography to afford the desired acetals.

20-methyl-Pregn-4-en-3-one-acetals (e.g. entry 6 in FIG. 2B, compound (10) in FIG. 12A or FIG. 19) were prepared using the same method using 3-oxo-9β-pregn-4-ene-20α-carboxaldehyde (compound 71), also employing TMSOCH$_2$CH$_2$CH$_2$OTMS and TMSOTf as reagents.

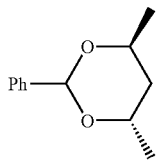

(4S,6S)-4,6-Dimethyl-2-phenyl-1,3-dioxane: colourless oil, 90% yield.

R$_f$: 0.64 (Hexane:Ethyl Acetate=4:1)

$^1$H NMR (400 MHz, CDCl$_3$): 7.51-7.49 (m, 2H), 7.38-7.29 (m, 3H), 5.83 (s, 1H), 4.48 (q, J=6.78 Hz, 1H), 4.20 (dqd, J=11.98, 6.00, 2.41 Hz, 1H), 1.99 (ddd, J=13.24, 11.85, 6.06 Hz, 1H), 1.49 (d, J=6.99 Hz, 3H), 1.48 (ddd, J=13.58, 2.44, 1.04 Hz, 1H), 1.27 (d, J=6.18 Hz, 3H)

$^{13}$C NMR (100 MHz, CDCl$_3$): 139.18, 128.65, 128.28, 126.24, 94.06, 68.67, 69.11, 36.77, 21.96, 17.24

HRMS (EI): m/z calculated for O$_{12}$H$_{16}$O$_2$ [M]$^+$: 192.1150. Found: 192.1137.

FTIR (KBr): ν 2976, 1071, 1456, 1377, 1132, 650 cm$^{-1}$

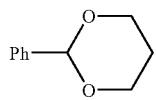

2-Phenyl-1,3-dioxane: white solid, 90% yield.

R$_f$: 0.64 (Hexane:Ethyl Acetate=4:1)

$^1$H NMR (400 MHz, CDCl$_3$): 7.64-7.41 (m, 5H), 5.55 (5, 1H), 4.27 (ddd, J=11.81, 5.02, 1.24 Hz, 2H), 3.99 (td, J=12.32, 2.24 Hz, 2H), 2.29-2.15 (m, 1H), 1.40-1.33 (m, 1H)

$^{13}$C NMR (100 MHz, CDCl$_3$): 138.52, 128.11, 127.58, 125.55, 100.90, 66.66, 25.20

HRMS (EI): m/z calculated for C$_{10}$H$_{12}$O$_2$ [M]$^+$: 164.0837. Found: 164.0825.

FTIR (NaCl): ν 3091, 3067, 3036, 2967, 2853, 1653, 1646, 1634, 1378, 1238, 1107, 1011, 749, 698 cm$^{-1}$

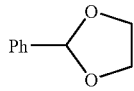

2-Phenyl-1,3-dioxolane: colourless oil, 95% yield.

R$_f$: 0.64 (Hexane:Ethyl Acetate=4:1)

$^1$H NMR (400 MHz, CDCl$_3$): 7.58-7.43 (m, 5H), 5.88 (s, 1H), 4.19-4.04 (m, 4H)

$^{13}$C NMR (100 MHz, CDCl$_3$): 137.86, 129.05, 128.23, 126.33, 103.63, 65.01

HRMS (EI): m/z calculated for C$_9$H$_{10}$O$_2$ [M]$^+$: 150.0681. Found: 150.0662.

FTIR (NaCl): ν 3089, 3066, 3035, 2963, 2926, 2887, 1648, 1637, 1457, 1243, 1094, 734 cm$^{-1}$

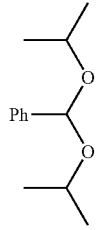

(Diisopropoxymethyl)benzene: colourless oil, 90% yield.

R$_f$: 0.64 (Hexane:Ethyl Acetate=4:1)

$^1$H NMR (400 MHz, CDCl$_3$): 7.53-7.31 (m, 5H), 5.59 (s, 1H), 3.94 (septet, J=6.27 Hz, 2H), 1.23 (d, J=6.27 Hz, 6H), 1.20 (d, J=6.27 Hz, 6H)

$^{13}$C NMR (100 MHz, CDCl$_3$): 140.34, 128.04, 127.95, 126.61, 99.14, 67.67, 22.96, 22.38

HRMS (EI): m/z calculated for C$_{13}$H$_{20}$O$_2$ [M]$^+$: 208.1463. Found: 191.0864.

FTIR (NaCl): ν 3089, 3066, 3035, 2963, 2926, 2887, 1648, 1637, 1457, 1243, 1094, 734 cm$^{-1}$

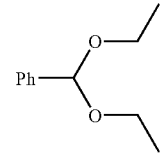

(Diethoxymethyl)benzene: colourless oil, 80% yield.

R$_f$: 0.64 (Hexane:Ethyl Acetate=4:1)

$^1$H NMR (400 MHz, CDCl$_3$): 7.50-7.48 (m, 2H), 7.39-7.30 (m, 3H), 5.55 (s, 1H), 3.66 (dq, J=9.64, 7.23 Hz, 2H), 3.56 (dq, J=9.64, 7.23 Hz, 2H), 1.25 (t, J=7.03 Hz, 6H)

$^{13}$C NMR (100 MHz, CDCl$_3$): 138.84, 127.97, 127.86, 126.37, 101.26, 60.65.14.90

HRMS (EI): m/z calculated for C$_{11}$H$_{16}$O$_2$ [M]$^+$: 180.1150. Found: 180.1858.

FTIR (NaCl): ν 3089, 3064, 3033, 2976, 2881, 1652, 1646, 1451, 1371, 1354, 1208, 1114, 1054, 749, 704 cm$^{-1}$

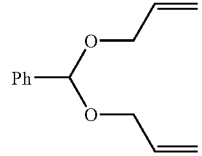

(Bis(allyloxy)methyl)benzene: colourless oil, 80% yield.

R$_f$: 0.64 (Hexane:Ethyl Acetate=4:1)

$^1$H NMR (400 MHz, CDCl$_3$): 7.55-7.33 (m, 5H), 5.97 (ddt, J=17.27, 10.44, 5.62 Hz, 2H), 5.67 (s, 1H), 5.34 (dq, J=17.27, 1.61 Hz, 2H), 5.20 (dq, J=10.04, 1.21 Hz, 2H), 4.09 (dt, J=5.62, 1.61 Hz, 4H)

$^{13}$C NMR (100 MHz, CDCl$_3$): 138.35, 134.44, 128.33, 128.10, 126.64, 116.59, 100.32, 66.01

HRMS (EI): m/z calculated for $C_{13}H_{16}O_2$ [M]$^+$: 204.1150. Found: 204.1092.

FTIR (NaCl): ν 3081, 3067, 3032, 2984, 2915, 2867, 1647, 1451, 1338, 1043, 922, 754, 709 cm$^{-1}$

Example 3

General Procedure for Cyclisation Reaction (2a~2f)

In all cases, only the data of major isomer 2 is reported. The ratio of isomers was determined by the integration of the respective signals in the $^1$H NMR spectra.

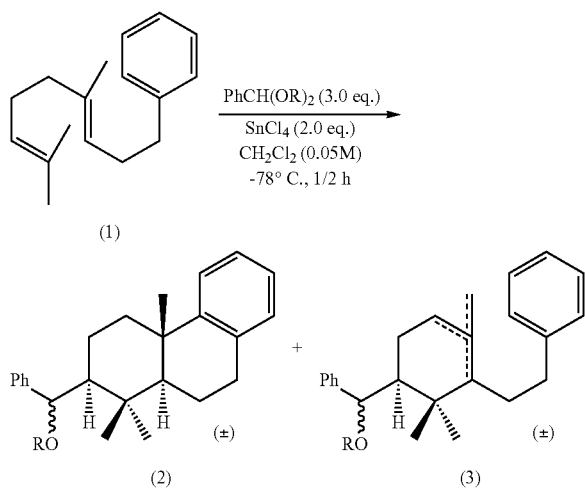

To a solution of alkene 1 (0.1 mmol, 1.0 eq.) in CH$_2$Cl$_2$ (2 mL) was added acetal (0.3 mmol, 2.0 eq.) at room temperature. The solution was cooled to −78° C. prior to addition of SnCl$_4$ (1.0 M in CH$_2$Cl$_2$, 0.2 mL, 2.0 eq.). The reaction was allowed to stir at −78° C. for 30 minutes before quenching with saturated NaHCO$_3$ aqueous solution (5 mL). The mixture was gradually warmed up to room temperature and was allowed to stirred for another 1 hour. The aqueous layer was extracted with CH$_2$Cl$_2$ (3×20 mL), and the combined organic layer was washed with water (20 mL), brine (20 mL) and dried over anhydrous Na$_2$SO$_4$, filtered and concentrated in vacuo. The residual crude product was purified by flash column chromatography.

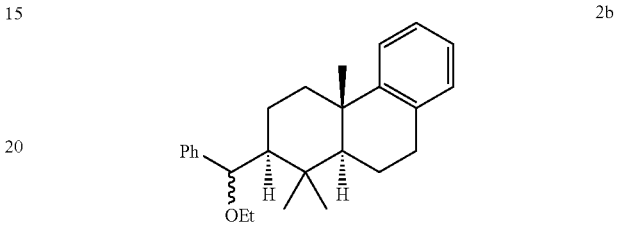

(2S,4aS,10aS)-2-(Ethoxy(phenyl)methyl)-1,1,4a-trimethyl-1,2,3,4,4a,9,10,10a-octahydrophenanthrene (2b): colourless oil, 90% yield. Diastereoisomer ratio 2b:2b'=88:12, isomer ratio[5] 2b:3b=86:14.

R$_f$: 0.73 (Hexane:Et$_2$O=9:1)

Major Isomer:

$^1$H NMR (400 MHz, CDCl$_3$): 7.30-6.92 (m, 9H), 4.52 (s, 1H), 3.35 (dq, J=8.94, 7.03 Hz, 1H), 3.21 (dq, J=8.88, 6.98 Hz, 1H), 2.87 (dd, J=16.85, 5.85 Hz, 1H), 2.76 (ddd, J=18.10, 11.34, 7.26 Hz, 1H), 2.18 (dt, J=12.60, 3.52 Hz, 1H), 1.88 (dd, J=13.98, 3.44 Hz, 1H), 1.83 (dd, J=13.86, 3.55 Hz, 1H,), 1.68 (qd, J=12.40, 6.41 Hz, 1H), 1.50-1.48 (m, 1H), 1.21 (dd, J=12.03, 1.72 Hz, 1H), 1.13-1.11 (m, 2H), 1.15 (s, 3H), 1.13 (s, 3H), 1.12 (s, 3H), 0.95 (s, 3H)

$^{13}$C NMR (100 MHz, CDCl$_3$): 149.89, 144.20, 135.06, 128.79, 128.00, 126.38, 126.19, 125.59, 125.08, 124.60, 80.22, 64.50, 55.98, 51.99, 38.75, 38.00, 37.36, 31.06, 30.41, 24.87, 19.55, 18.22, 16.76, 15.51

HRMS (EI): m/z calculated for $C_{26}H_{34}O$ [M]$^+$: 362.2610. Found: 362.2604.

FTIR (NaCl): ν 3100, 3084, 3061, 3024, 2968, 2928, 2874, 2840, 2782, 1602, 1490, 1450, 1377, 1260, 1117, 1088, 1073, 759, 739, 723, 702 cm$^{-1}$ (ddd, J=17.47, 11.24, 6.83 Hz, 1H), 2.27 (dt, J=12.85, 3.41 Hz, 1H), 1.99-1.94 (m, 1H), 1.90 (dd, J=12.85, 2.81 Hz, 1H), 1.85-1.72 (m, 1H), 1.62-1.60 (m, 1H), 1.33-1.31 (m, 1H), 1.29-1.25 (m, 2H), 1.23 (s, 3H), 1.22 (s, 3H), 1.03 (s, 3H)

$^{13}$C NMR (100 MHz, CDCl$_3$): 149.85, 143.44, 135.05, 128.12, 128.11, 126.52, 126.19, 125.60, 125.11, 124.57, 82.21, 56.85, 56.01, 51.90, 38.71, 37.99, 37.31, 31.03, 30.39, 24.80, 19.55, 18.19, 16.64

HRMS (EI): m/z calculated for $C_{25}H_{32}O$ [M]$^+$: 348.2453. Found: 348.2452.

FTIR (NaCl): ν 3061, 2928, 1602, 1489, 1451, 1377, 1110, 1084, 1072, 758, 702 cm$^{-1}$

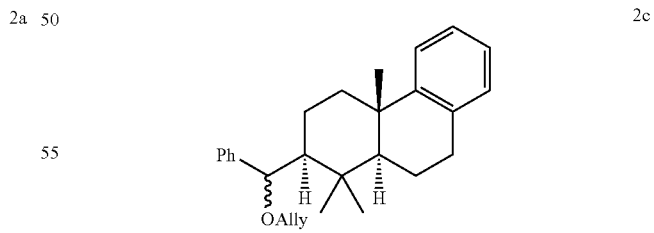

(2S,4aS,10aS)-2-(Methoxy(phenyl)methyl)-1,1,4a-trimethyl-1,2,3,4,4a,9,10,10a-octahydrophenanthrene (2a): colourless oil, 87% yield. Diastereoisomer ratio 2a:2a'=84:16, isomer ratio[5] 2a:3a=88:12.

R$_f$: 0.73 (Hexane:Et$_2$O=9:1)

Major Isomer:

$^1$H NMR (400 MHz, CDCl$_3$): 7.38-7.01 (m, 9H), 4.50 (s, 1H), 3.26 (s, 3H), 2.97 (ddd, J=17.07, 6.63, 1.81 Hz, 1H), 2.84

(2S,4aS,10aS)-2-(Allyloxy(phenyl)methyl)-1,1,4a-trimethyl-1,2,3,4,4a,9,10,10a-octahydrophenanthrene (2c): colourless oil, 84% yield. Diastereoisomer ratio 2c:2c'=83:17, isomer ratio[5] 2c:3c=97:3.

R$_f$: 0.73 (Hexane:Et$_2$O=9:1)

Major Isomer:

$^1$H NMR (400 MHz, CDCl$_3$): 7.29-6.91 (m, 9H), 5.86 (tdd, J=17.18, 10.54, 5.27 Hz, 1H), 5.21 (dq, J=17.19, 1.72 Hz, 1H), 5.06 (dq, J=10.43, 1.53 Hz, 1H), 4.58 (s, 1H), 3.85 (ddt, J=12.83, 5.04, 1.49 Hz, 1H), 3.68 (ddt, J=12.72, 5.39, 1.47 Hz, 1H), 2.86 (dd, J=16.84, 5.85 Hz, 1H), 2.75 (ddd, J=17.50, 11.34, 7.33 Hz, 1H), 2.18 (dt, J=12.60, 3.09 Hz, 1H), 1.92-1.88 (m, 1H), 1.86-1.82 (m, 1H), 1.67 (qd, J=12.37, 6.42 Hz, 1H), 1.20 (dd, J=12.15, 1.83 Hz, 1H), 1.15-1.11 (m, 3H), 1.14 (s, 3H), 1.11 (s, 3H), 0.94 (s, 3H)

$^{13}$C NMR (100 MHz, CDCl$_3$): 149.85, 143.59, 135.13, 135.05, 128.70, 128.09, 126.54, 126.23, 125.60, 125.10, 124.59, 115.92, 79.87, 69.82, 56.07, 51.97, 38.74, 37.99, 37.35, 31.04, 30.36, 24.87, 19.54, 18.40, 16.77

HRMS (EI): m/z calculated for C$_{27}$H$_{34}$O [M]$^+$: 374.2610. Found: 374.2608.

FTIR (NaCl): ν 3097, 3083, 3061, 3023, 2963, 2945, 2913, 2872, 2836, 1646, 1602, 1490, 1449, 1376, 1067, 916, 759, 702 cm$^{-1}$

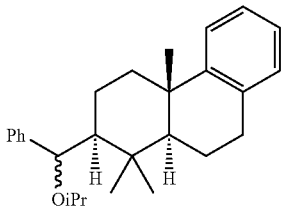

2d (2S,4aS,10aS)-2-(Isopropoxy(phenyl)methyl)-1,1,4a-trimethyl-1,2,3,4,4a,9,10,10a-octahydrophenanthrene (2d): colourless oil, 94% yield. Diastereoisomer ratio 2d:2d'=84:16, isomer ratio$^5$ 2d:3d=80:20.

R$_f$: 0.70 (Hexane:Et$_2$O=9:1)

Major Isomer:

$^1$H NMR (400 MHz, CDCl$_3$): 7.29-6.91 (m, 9H), 4.70 (s, 1H), 3.40 (septet, J=6.05 Hz, 1H), 2.85 (dd, J=17.08, 4.93 Hz, 1H), 2.74 (ddd, J=17.41, 11.23, 6.64 Hz, 1H), 2.16 (dt, J=12.83, 3.38 Hz, 1H), 1.85-1.83 (m, 1H), 1.81-1.79 (m, 1H), 1.66 (dd, J=12.37, 6.36 Hz, 1H), 1.54 (dq, J=4.32, 3.55 Hz, 1H), 1.16 (dd, J=12.14, 1.83 Hz, 1H), 1.13 (s, 3H), 1.11 (s, 3H), 1.10-0.90 (m, 2H), 1.06 (d, J=5.96 Hz, 3H), 0.99 (d, J=6.19 Hz, 3H), 0.95 (s, 3H)

$^{13}$C NMR (100 MHz, CDCl$_3$): 149.97, 145.18, 135.06, 128.76, 127.84, 126.49, 126.30, 125.57, 125.05, 124.58, 77.20, 69.28, 56.19, 52.20, 38.96, 38.00, 37.46, 31.03, 30.22, 24.96, 23.58, 21.29, 19.45, 18.51, 16.84

HRMS (EI): m/z calculated for C$_{27}$H$_{36}$O [M]$^+$: 376.2766. Found: 376.2767.

FTIR: ν 3102, 3084, 3060, 2968, 2930, 2973, 2831, 1602, 1489, 1451, 1378, 1120, 1103, 1059, 759, 739, 723, 702 cm$^{-1}$

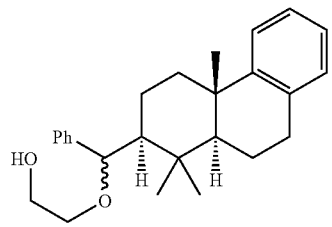

2e 2-(Phenyl((2S,4aS,10aS)-1,1,4a-trimethyl-1,2,3,4,4a,9,10,10a-octahydrophenanthren-2-yl)methoxy)ethanol (2e): colourless oil, 72% yield. Diastereoisomer ratio 2e:2e'=90:10.

R$_f$: 0.15 (Hexane:Ethyl Acetate=4:1)

Major Isomer:

$^1$H NMR (400 MHz, CDCl$_3$): 6.97-7.39 (m, 9H), 4.67 (s, 1H), 3.80-3.60 (m, 2H), 3.53 (ddd, J=9.76, 5.22, 3.48 Hz, 1H), 3.36 (ddd, J=9.93, 6.45, 3.48 Hz, 1H), 2.96 (ddd, J=17.25, 6.46, 1.74 Hz, 1H), 2.83 (ddd, J=17.68, 11.50, 6.62 Hz, 1H), 2.27 (dt, J=12.89, 3.14 Hz, 1H), 2.05-1.85 (m, 2H), 1.80-1.55 (m, 2H), 1.40-1.20 (m, 3H), 1.22 (s, 3H), 1.21 (s, 3H), 1.04 (s, 3H)

$^{13}$C NMR (125 MHz, CDCl$_3$): 149.70 (C), 143.18 (C), 135.00 (C), 128.82 (CH), 128.21 (CH), 126.73 (CH), 126.18 (CH), 125.63 (CH), 125.16 (CH), 124.53 (CH), 80.80 (CH), 70.16 (CH$_2$), 62.30 (CH$_2$), 56.03 (CH), 51.90 (CH), 38.67 (CH$_2$), 37.96 (C), 37.36 (C), 30.99 (CH$_2$), 30.31 (CH$_3$), 24.89 (CH$_3$), 19.55 (CH$_2$), 18.61 (CH$_3$), 16.66 (CH$_2$)

HRMS (ESI): m/z calculated for C$_{26}$H$_{34}$O$_2$ [M]$^+$: 378.2559. Found [M+Na]$^+$: 401.2450.

FTIR (KBr): ν 3369, 2958, 2873, 1653, 1489, 1448, 1375, 1116, 1053, 759, 723, 702 cm$^{-1}$.

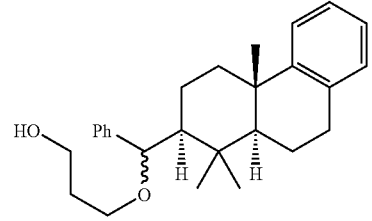

2f 3-(Phenyl((2S,4aS,10aS)-1,1,4a-trimethyl-1,2,3,4,4a,9,10,10a-octahydrophenanthren-2-yl)methoxy)propan-1-ol (2f): colourless oil, 76% yield. Diastereoisomer ratio 2f:2f'=88:12.

R$_f$: 0.15 (Hexane:Ethyl Acetate=4:1)

Major Isomer:

$^1$H NMR (500 MHz, CDCl$_3$): 7.38-7.17 (m, 6H), 7.10-6.84 (m, 3H), 4.59 (s, 1H), 3.84 (t, J=5.55 Hz, 2H), 3.56 (ddd, J=9.04, 6.68, 4.63 Hz, 1H), 3.47 (ddd, J=9.14, 6.49, 4.63 Hz, 1H), 2.95 (dd, J=17.11, 5.09 Hz, 1H), 2.83 (ddd, J=17.40, 11.93, 7.4 Hz, 1H), 2.67 (dt, J=12.95, 3.24 Hz, 1H), 1.93-1.60 (m, 5H), 1.60-1.50 (m, 2H), 1.40-1.10 (m, 2H), 1.22 (s, 3H), 1.21 (s, 3H), 1.03 (s, 3H)

$^{13}$C NMR (125 MHz, CDCl$_3$): 149.66 (C), 143.28 (C), 134.97 (C), 128.80 (CH), 128.25 (CH), 126.71 (CH), 126.04 (CH), 125.63 (CH), 125.15 (CH), 124.53 (CH), 81.13 (CH), 68.67 (CH$_2$), 62.46 (CH$_2$), 55.89 (CH), 51.86 (CH), 38.56 (CH$_2$), 37.94 (C), 37.33 (C), 32.33 (CH$_2$), 30.97 (CH$_2$), 30.35 (CH$_3$), 24.85 (CH$_3$), 19.55 (CH$_2$), 18.22 (CH$_3$), 16.75 (CH$_2$)

HRMS (EI): m/z calculated for C$_{27}$H$_{36}$O$_2$ [M]$^+$: 392.2715. Found [M+Na]$^+$: 415.2630.

FTIR (KBr): ν 3446, 2945, 1653, 1624, 1489, 1448, 1109, 1070, 758, 723, 702 cm$^{-1}$

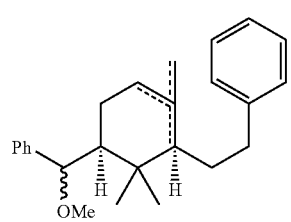

3a (S)-(Methoxy(2,2,4-trimethyl-3-phenethylcyclohex-3-enyl)methyl)benzene (3a): colourless oil, mixture of isomers $R_f$: 0.73 (Hexane:Et$_2$O=9:1)

$^1$H NMR (300 MHz, CDCl$_3$): as a mixture of isomers. Major isomer 7.38-7.01 (m, 10H), 4.48 (s, 1H), 3.24 (s, 3H), 2.63-2.54 (m, 2H), 2.30-2.22 (m, 2H), 1.88-1.82 (m, 1H), 1.75-1.65 (m, 1H), 1.68 (s, 3H), 1.56-1.47 (m, 2H), 1.37-1.33 (m, 1H), 1.30 (s, 3H), 1.09 (s, 3H)

$^{13}$C NMR (75 MHz, CDCl$_3$): 143.51, 143.18, 136.98, 128.38, 128.13, 128.10, 127.82, 126.56, 126.21, 125.73, 82.30, 56.75, 53.64, 39.02, 36.74, 32.91, 31.56, 27.44, 22.42, 20.14, 17.14

HRMS (EI): m/z calculated for C$_{25}$H$_{32}$O [M]$^+$: 348.2453. Found: 348.2452.

FTIR (NaCl): ν 3061, 2929, 2827, 1602, 1493, 1451, 1377, 1118, 1088, 1072, 758, 739, 701 cm$^{-1}$

Example 4

General Procedure for Asymmetric Cyclisation Reaction (2g~2l)

In all cases, only the data of major isomer 2 is reported. The ratio of isomers was determined by the integration of the respective signals in the $^1$H NMR spectra.

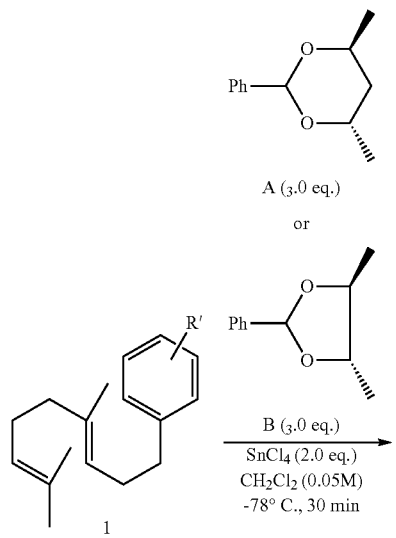

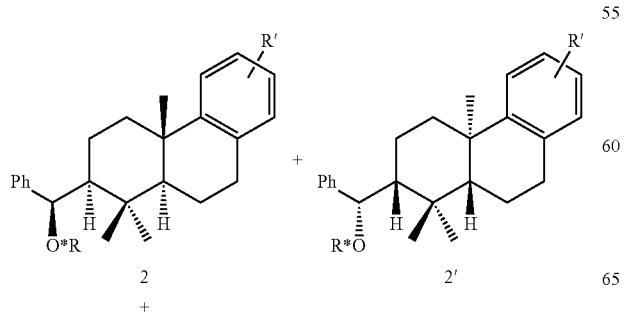

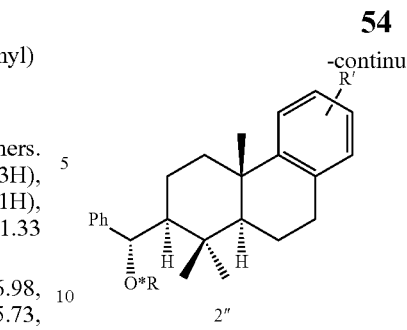

Procedures for asymmetric cyclisation are the same as cyclisation reaction of 1a, despite using chiral acetal as initiators.

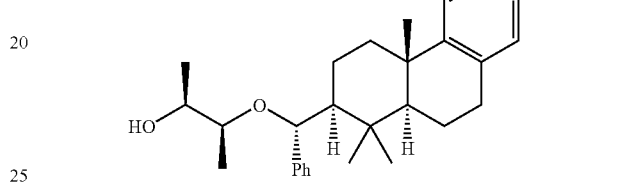

(2S,3R)-3-((R)-Phenyl((2S,4aS,10aS)-1,1,4a-trimethyl-1,2,3,4,4a,9,10,10a-octahydrophenanthren-2-yl)methoxy)butan-2-ol (2l): colourless oil, 58% yield. Diastereoisomer ratio 2i+2i":2i'+2i'"=89:11, isomer ratio$^6$ 2i:2i':2i":2i'"=76:8:13:3.

Side product (75/75') was obtained in 25% yield as well (see FIG. 22).

$R_f$: 0.15 (Hexane:Et$_2$O=9:1)

Major Isomer:

$^1$H NMR (500 MHz, CDCl$_3$): 7.38-6.96 (m, 9H), 4.94 (s, 1H), 3.64 (quintet, J=6.42 Hz, 1H), 3.25 (quintet, J=6.53 Hz, 1H), 2.98-2.92 (m, 1H), 2.82 (ddd, J=17.61, 15.06, 6.49 Hz, 1H), 2.30 (dt, J=12.94, 3.24 Hz, 1H), 1.98-1.83 (m, 2H), 1.83-1.60 (m, 3H), 1.30-1.20 (m, 2H), 1.21 (s, 3H), 1.17 (s, 3H), 1.15 (d, J=6.48 Hz, 3H), 1.10 (d, J=6.01 Hz, 3H), 1.03 (s, 3H)

$^{13}$C NMR (125 MHz, CDCl$_3$): 149.75 (C), 142.62 (C), 135.01 (C), 128.81 (CH), 128.28 (CH),126.89 (CH), 126.84 (CH), 125.65 (CH), 125.16 (CH), 124.52 (CH), 75.33 (CH), 74.81 (CH), 71.87 (CH), 55.85 (CH), 52.14 (CH), 38.86 (CH), 37.96 (C), 37.58 (C), 30.98 (CH$_2$), 30.17 (CH$_3$), 24.97 (CH$_3$), 19.45 (CH$_2$), 18.84 (CH$_3$), 18.83 (CH$_3$), 17.07 (CH$_2$), 14.21 (CH$_3$)

HRMS (EI): m/z calculated for C$_{28}$H$_{38}$O$_2$ [M]$^+$: 406.2872. Found: 406.2866.

FTIR (KBr): ν 3406, 2968, 2873, 1489, 1448, 1375, 1105, 1064, 758, 702 cm$^{-1}$ (2R,4R)-4-((R)-Phenyl((2S,4aS,10aS)-1,1,4a-trimethyl-1,2,3,4,4a,9,10,10a-octahydrophenanthren-2-yl)methoxy)pentan-2-ol (2j): colourless oil, 89% yield. Diastereoisomer ratio 2j+2j":2j'=82:18, isomer ratio⁶ 2j:2j':2j"=66:18:16

R*f*: 0.15 (Hexane:Et₂O=9:1)

Major Isomer:

¹H NMR (400 MHz, CDCl₃): 7.42-6.94 (m, 9H), 4.91 (s, 1H), 4.25 (t, J=7.32 Hz, 1H), 3.75-3.55 (m, 1H), 2.94 (dd, J=16.73, 6.27 Hz, 1H), 2.81 (ddd, J=16.90, 10.96, 7.32 Hz, 1H), 2.28 (dt, J=12.89, 3.48 Hz, 1H), 1.95-1.85 (m, 1H), 1.85-1.60 (m, 3H), 1.55-1.45 (m, 1H), 1.40-1.00 (m, 4H), 1.25 (d, J=6.27 Hz, 3H), 1.22 (s, 3H), 1.20 (s, 3H), 1.18 (s, 3H), 1.06 (s, 3H)

¹³C NMR (100 MHz, CDCl₃): 149.72 (C), 143.26 (C), 134.93 (C), 128.78 (CH), 128.30 (CH), 127.00 (CH), 126.50 (CH), 125.64 (CH), 125.16 (CH), 124.50 (CH), 77.10 (CH), 70.68 (CH), 64.20 (CH), 55.60 (CH), 52.13 (CH), 44.43 (CH₂), 38.83 (CH₂), 37.94 (C), 37.56 (C), 30.92 (CH₂), 30.10 (CH₃), 25.03 (CH₃), 23.43 (CH₃), 19.43 (CH₂), 18.61 (CH₃), 17.56 (CH₃), 17.22 (CH₂)

FTIR (KBr): ν 2446, 1662, 1635, 1448, 1375, 1120, 1056, 759, 725, 702 cm⁻¹

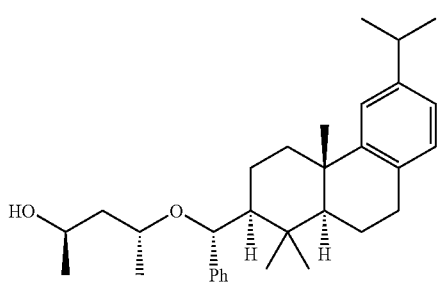

2k (2R,4R)-4-((R)-((2S,4aS,10aS)-6-Isopropyl-1,1,4a-trimethyl-1,2,3,4,4a,9,10,10a-octahydrophenanthren-2-yl)(phenyl)methoxy)pentan-2-ol (2k): colourless oil, 88% yield. Diastereoisomer ratio 2k+2k":2k'=86:14, isomer ratio 2k:2k': 2k"=73:14:13 (The three new chiral centers formed are considered as a chiral group of (fixed relative configuration within the group) based on the Stork-Eschenmoser postulate.)

R*f*: 0.15 (Hexane:Et₂O=9:1)

Major Isomer:

¹H NMR (400 MHz, CDCl₃): 7.43-7.22 (m, 5H), 7.19-6.89 (m, 3H), 4.93 (s, 1H), 4.27 (dd, J=14.28, 6.97 Hz, 1H), 4.00-3.60 (m, 1H), 3.55-3.45 (m, 1H), 2.93 (dd, J=16.55, 6.27 Hz, 1H), 3.00-2.85 (m, 1H), 2.79 (dt, J=13.94, 6.97 Hz, 1H), 2.32 (dt, J=12.89, 3.14 Hz, 1H), 2.00-1.90 (m, 1H), 1.85-1.60 (m, 3H), 1.53 (dd, J=13.07, 6.97 Hz, 1H), 1.50-1.00 (m, 3H), 1.27 (d, J=6.27 Hz, 3H), 1.23 (d, J=6.27 Hz, 3H), 1.23 (s, 3H), 1.21 (d, J=1.74 Hz, 3H), 1.20 (s, 3H), 1.18 (d, J=1.39 Hz, 3H), 1.08 (s, 3H)

¹³C NMR (100 MHz, CDCl₃): 149.60 (C), 146.06 (C), 143.29 (C), 132.31 (C), 128.67 (CH), 128.27 (CH), 126.99 (CH), 126.51 (CH), 123.18 (CH), 122.54 (CH), 77.16 (CH), 70.68 (CH), 64.22 (CH), 55.79 (CH), 52.25 (CH), 44.49 (CH₂), 38.94 (CH₂), 38.03 (C), 37.59 (C), 34.00 (CH₂), 30.52 (CH₂), 30.09 (CH₃), 25.03 (CH₃), 24.22 (CH₃), 24.08 (CH₃), 23.44 (CH₃), 19.50 (CH₂), 18.61 (CH₃), 17.59 (CH₃), 17.22 (CH₂)

HRMS (EI): m/z calculated for C₃₂H₄₆O₂ [M]⁺: 462.3498. Found: 462.3481.

FTIR (KBr): ν 3446, 2962, 2870, 1450, 1377, 1120, 1103, 1056, 704 cm⁻¹

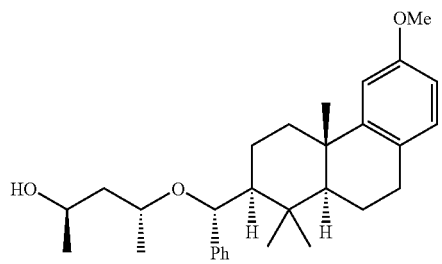

21

(2R,4R)-4-((R)-((2S,4aS,10aS)-6-Methoxy-1,1,4a-trimethyl-1,2,3,4,4a,9,10,10a-octahydrophenanthren-2-yl)(phenyl)methoxy)pentan-2-ol (21): colourless oil, 75% yield. Diastereoisomer ratio 2l+2l":2l'=84:16, isomer ratio⁶ 2l:2l': 2l"=72:16:12.

R*f*: 0.15 (Hexane:Et₂O=9:1)

Major Isomer:

¹H NMR (400 MHz, CDCl₃): 7.40-7.20 (m, 5H), 6.95-6.90 (m, 1H), 6.75-6.65 (m, 1H), 6.65-6.48 (m, 1H), 4.91 (s, 1H), 4.25 (dd, J=13.59, 6.62 Hz, 1H), 3.73 (s, 3H), 3.70-3.60 (m, 1H), 2.89 (dd, J=16.72, 6.27 Hz, 1H), 2.73 (ddd, J=16.72, 10.80, 6.97 Hz, 1H), 2.23 (dt, J=12.89, 3.13 Hz, 1H), 1.95-1.85 (m, 1H), 1.85-1.60 (m, 3H), 1.55-1.45 (m, 1H), 1.30-1.00 (m, 4H), 1.25 (d, J=6.27 Hz, 3H), 1.21 (d, J=5.52 Hz, 3H), 1.20 (s, 3H), 1.18 (s, 3H), 1.05 (s, 3H)

¹³C NMR (125 MHz, CDCl₃): 157.67 (C), 151.01 (C), 145.91 (C), 143.24 (C), 129.54 (CH), 128.30 (CH), 126.49 (CH), 125.98 (CH), 110.88 (CH), 110.16 (CH), 77.09 (CH), 70.67 (CH), 64.21 (CH), 55.65 (CH), 55.21 (CH₃), 52.12 (CH), 44.41 (CH₂), 38.85 (CH₂), 38.14 (C), 37.56 (C), 30.12 (CH₃), 30.11 (CH₂), 24.94 (CH₃), 23.42 (CH₃), 19.56 (CH₂), 18.63 (CH₃), 17.55 (CH₃), 17.22 (CH₂)

HRMS (EI): m/z calculated for C₃₀H₄₂O₃ [M]⁺: 450.3134. Found: 450.3121.

FTIR (KBr): ν 3500, 2976, 2873, 2252, 1608, 1510, 1502, 1490, 1456, 1377, 1251, 1132, 1058, 1043, 650 cm⁻¹

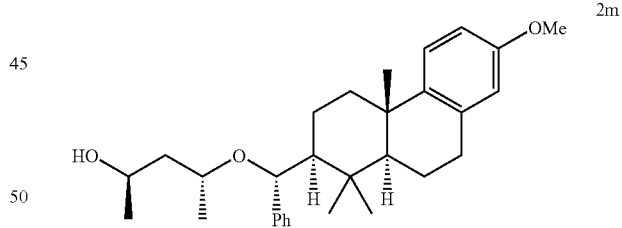

2m (2R,4R)-4-((R)-((2S,4aS,10aS)-7-Methoxy-1,1,4a-trimethyl-1,2,3,4,4a,9,10,10a-octahydrophenanthren-2-yl)(phenyl)methoxy)pentan-2-ol (2m): colourless oil, 65% yield. Diastereoisomer ratio 2m+2m":2m'=81:19, isomer ratio⁶ 2m:2m':2m"=66:19:15

15% yield product with benzene ring cyclised at meta position to OMe was observed as well.

R*f*: 0.15 (Hexane:Et₂O=9:1)

Major Isomer:

¹H NMR (500 MHz, CDCl₃): 7.39-7.22 (m, 5H), 7.12-7.03 (m, 1H), 6.82-6.06 (m, 1H), 6.58-6.44 (m, 1H), 4.89 (s, 1H), 4.30-4.20 (m, 1H), 3.73 (s, 3H), 3.70-3.60 (m, 1H), 2.90 (dd, J=17.11, 5.09 Hz, 1H), 2.79 (ddd, J=17.11, 11.56, 6.93 Hz, 1H), 2.24 (dt, J=12.95, 3.24 Hz, 1H), 1.95-1.85 (m, 1H), 1.85-1.60 (m, 3H), 1.60-1.45 (m, 1H), 1.45-1.10 (m, 4H), 1.25 (d, J=6.48 Hz, 3H), 1.21 (s, 3H), 1.93 (d, J=3.69 Hz, 3H), 1.17 (s, 3H), 1.05 (s, 3H)

$^{13}$C NMR (125 MHz, CDCl$_3$): 156.98 (C), 143.25 (C), 142.31 (C), 136.26 (C), 128.30 (CH), 127.00 (CH), 126.50 (CH), 125.60 (CH), 113.05 (CH), 111.88 (CH), 77.13 (CH), 70.70 (CH), 64.22 (CH), 55.68 (CH), 55.08 (CH$_3$), 52.38 (CH), 44.37 (CH$_2$), 39.03 (CH$_2$), 37.48 (C), 37.41 (C), 31.20 (CH$_2$), 30.13 (CH$_3$), 25.12 (CH$_3$), 23.42 (CH$_3$), 19.46 (CH$_2$), 18.59 (CH$_3$), 17.54 (CH$_3$), 17.22 (CH$_2$)

HRMS (EI): m/z calculated for C$_{30}$H$_{42}$O$_3$ [M]$^+$: 450.3134. Found: 450.3123.

FTIR (KBr): ν 3481, 2966, 1606, 1498, 1452, 1377, 1263, 1242, 1151, 1124, 1151, 1124, 1055, 1037, 704, 648 cm$^{-1}$ (2R,4R)-4((R)-Phenyl((2S,4aS,10aS)-1,1,4a,6-tetramethyl-1,2,3,4,4a,9,10,10a-octahydrophenanthren-2-yl)methoxy)pentan-2-ol (2n): colourless oil, 87% yield. Diastereoisomer ratio 2n+2n":2n'=83:17, isomer ratio$^6$ 2n:2n':2n"=66:17:17.

R$_f$: 0.15 (Hexane:Et$_2$O=9:1)

Major Isomer:
$^1$H NMR (400 MHz, CDCl$_3$): 7.41-7.19 (m, 5H), 6.99-6.77 (m, 3H), 4.90 (s, 1H), 4.35-4.19 (m, 1H), 3.80-3.60 (m, 1H), 2.90 (dd, J=16.55, 5.93 Hz, 1H), 2.76 (ddd, J=17.32, 10.80, 7.03 Hz, 1H), 2.30 (dt, J=9.75, 3.14 Hz, 1H), 2.40 (s, 3H), 1.95-1.85 (m, 1H), 1.80-1.60 (m, 3H), 1.58-1.45 (m, 1H), 1.40-1.10 (m, 4H), 1.24 (d, J=7.66 Hz, 3H), 1.22 (s, 3H), 1.19 (s, 3H), 1.17 (s, 3H), 1.05 (s, 3H)

$^{13}$C NMR (100 MHz, CDCl$_3$): 149.58 (C), 143.28 (C), 134.81 (C), 131.80 (C), 128.68 (CH), 128.28 (CH), 126.99 (CH), 126.50 (CH), 126.07 (CH), 125.01 (CH), 77.14 (CH), 70.69 (CH), 64.20 (CH), 55.72 (CH), 52.23 (CH), 44.42 (CH$_2$), 38.88 (CH$_2$), 37.87 (C), 37.56 (C), 30.50 (CH$_2$), 30.10 (CH$_3$), 25.00 (CH$_3$), 23.42 (CH$_3$), 21.23 (CH$_3$), 19.51 (CH$_2$), 18.61 (CH$_3$), 17.56 (CH$_3$), 17.20 (CH$_2$)

HRMS (EI): m/z calculated for C$_{30}$H$_{42}$O$_2$ [M]$^+$: 434.3185. Found: 434.3187.

FTIR (KBr): ν 3466, 2966, 1450, 1377, 1122, 1056, 704 cm$^{-1}$.

(2R,4R)-4-((R)-Phenyl((2S,4aS,10aS)-1,1,4a,7-tetramethyl-1,2,3,4,4a,9,10,10a-octahydrophenanthren-2-yl)methoxy)pentan-2-ol (2o): colourless oil, 85% yield. Diastereoisomer ratio 2o+2o":2o'=82:18, isomer ratio$^6$ 2o:2o':2o"=71:18:11.

R$_f$: 0.15 (Hexane:Et$_2$O=9:1)

Major Isomer:
$^1$H NMR (500 MHz, CDCl$_3$): 7.39-7.23 (m, 5H), 7.11-6.97 (m, 1H), 6.88-6.78 (m, 2H), 4.90 (s, 1H), 4.30-4.14 (m, 1H), 3.70 (dd, J=10.64, 4.62 Hz, 1H), 2.89 (dd, J=16.88, 5.32 Hz, 1H), 2.77 (ddd, J=17.10, 11.50, 6.47 Hz, 1H), 2.33 (d, J=6.01 Hz, 1H), 2.23 (s, 3H), 1.95-1.85 (m, 1H), 1.85-1.72 (m, 3H), 1.60-1.50 (m, 1H), 1.40-1.10 (m, 4H), 1.25 (d, J=6.01 Hz, 3H), 1.20 (d, J=6.47 Hz, 3H), 1.19 (s, 3H), 1.17 (s, 3H), 1.05 (s, 3H)

$^{13}$C NMR (75 MHz, CDCl$_3$): 146.91 (C), 143.29 (C), 134.80 (C), 134.50 (C), 129.33 (CH), 128.30 (CH), 127.94 (CH), 127.00 (CH), 126.53 (CH), 124.45 (CH), 77.14 (CH), 70.65 (CH), 64.20 (CH), 55.72 (CH), 52.34 (CH), 44.47 (CH$_2$), 38.92 (CH$_2$), 37.65 (C), 37.54 (C), 30.89 (CH$_2$), 30.14 (CH$_3$), 25.07 (CH$_3$), 23.44 (CH$_3$), 20.76 (CH$_3$), 19.46 (CH$_2$), 18.61 (CH$_3$), 17.58 (CH$_3$), 17.27 (CH$_2$)

HRMS (EI): m/z calculated for C$_{30}$H$_{42}$O$_3$ [M]$^+$: 434.3185. Found: 434.3164.

FTIR (KBr): ν 3488, 2966, 1494, 1450, 1377, 1122, 1056, 815, 704 cm$^{-1}$

Example 5

Functionalisation of Cyclisation Products

In all cases, only the data of major isomer 2 is reported. The ratio of isomers was determined by the integration of the respective signals in the $^1$H NMR spectra unless otherwise stated.

(R)-4-((R)-Phenyl((2S,4aS,10aS)-1,1,4a-trimethyl-1,2,3,4,4a,9,10,10a-octahydrophenanthren-2-yl)methoxy)pentan-2-one (72)

To an oven-dried 25 mL round-bottom flask equipped with a magnetic stirring bar was added PCC (0.324 g, 1.5 mmol, 3.0 eq.), 4 Å MS (1.0 g, oven-dried 48 hours), silica gel (1 g, oven-dried 48 hours) and CH$_2$Cl$_2$ (8 mL). The mixture was allowed to cool to 0° C. and alcohol 2j/2j'/2j" (0.21 g, 0.5 mmol, 1.0 eq.) in CH$_2$Cl$_2$ (2 mL) was added slowly. The reaction mixture was gradually warmed up to room temperature and was allowed to stir for another 12 hours. The mixture was filtered through a pad of silica gel and was flushed with 200 mL CH$_2$Cl$_2$. The solution was concentrated in vacuo. The residual product was purified by flash column chromatography to afford the desired product as a white solid in 81% yield. Diastereoisomer ratio 72+72":72'=81:19, isomer ratio, 72:72':72"=67:19:14

R$_f$: 0.66 (Hexane:Ethyl Acetate=4:1)

Major Product:
$^1$H NMR (400 MHz, CDCl$_3$): 7.34-7.18 (m, 7H), 7.09-7.00 (m, 2H), 4.83 (s, 1H), 3.89 (sextet, J=6.04 Hz, 1H), 2.94 (dd, J=16.40, 5.40 Hz, 1H), 2.86-2.81 (m, 1H), 2.65 (dd, J=14.84, 6.64 Hz, 1H), 2.41 (dd, J=14.95, 5.81 Hz, 1H), 2.23 (dt, J=12.98, 3.12 Hz, 1H), 2.20-2.10 (m, 1H), 2.19 (s, 3H), 1.95-1.80 (m, 2H), 1.77-1.68 (m, 1H), 1.66 (m, 2H), 1.24 (dd, J=12.04, 1.55 Hz, 1H), 1.24 (s, 3H), 1.22 (d, J=5.81 Hz, 3H), 1.21 (s, 3H), 1.07 (s, 3H)

$^{13}$C NMR (100 MHz, CDCl$_3$): 207.90, 149.77, 143.67, 135.04, 128.82, 128.11, 126.74, 126.64, 125.64, 125.15, 124.58, 76.80, 69.16, 56.01, 52.11, 51.40, 38.84, 37.95, 37.50, 31.40, 31.04, 30.24, 24.99, 19.49, 19.10, 19.67, 16.86

HRMS (EI): m/z calculated for C$_{29}$H$_{38}$O$_2$ [M]$^+$: 418.2872. Found: 418.2859.

FTIR (KBr): ν 2966, 1714, 1635, 1450, 1375, 1101, 1083, 1055, 760, 739, 704 cm$^{-1}$

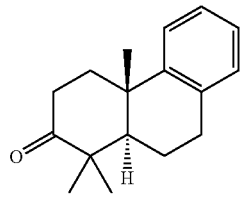

(4aS,10aR)-1,1,4a-Trimethyl-4,4a,10,10a-tetrahydrophenanthren-2(1H,3H,9H)-one (73)

To an oven-dried 25 mL round-bottom flask was added ketone 72/72'/72'' (42 mg, 0.1 mmol, 1.0 eq.), SeO$_2$ (33 mg, 0.3 mmol, 3.0 eq.), NaH (0.2 g, 70% in mineral oil, 5.8 mmol, 58 eq.) and THF (10 mL). tBuOK solution was added to the reaction mixture via syringe. The reaction mixture was refluxed for 24 hours and was quenched with MeOH (5 mL) at 0° C. The mixture was diluted with water and was extracted with diethyl ether (3×20 mL), and the combined organic layer was washed with water (20 mL) and brine (20 mL). The organic layer was dried over anhydrous Na$_2$SO$_4$, filtered and concentrated in vacuo. The residual crude product was purified by flash column chromatography to afford desired product as a colourless solid in 45% yield, 52% ee.

R$_f$: 0.74 (Hexane:Ethyl Acetate=4:1)

$^1$H NMR (400 MHz, CDCl$_3$): 7.18-7.03 (m, 4H), 3.01 (ddd, J=16.84, 6.00, 1.98 Hz, 1H), 2.90 (ddd, J=17.93, 11.23, 6.60 Hz, 1H), 2.75-2.67 (m, 1H), 2.60 (ddd, J=15.68, 7.59, 4.12 Hz, 1H), 2.53 (ddd, J=13.21, 7.43, 5.96 Hz, 1H), 1.98-1.91 (m, 2H), 1.84-1.77 (m, 2H), 1.30 (s, 3H), 1.17 (s, 3H), 1.14 (s, 3H)

$^{13}$C NMR (100 MHz, CDCl$_3$): 217.23, 147.37, 134.87, 129.06, 126.10, 125.80, 125.40, 50.59, 47.39, 37.49, 37.37, 34.63, 30.81, 26.85, 24.68, 21.11, 20.16

HRMS (EI): m/z Calculated for C$_{17}$H$_{22}$O [M]$^+$: 242.1671. Found: 242.1672.

FTIR: (NaCl): ν 1701, 1653, 1647, 761 cm$^{-1}$

The enantiomeric excess was determined by HPLC analysis employing Daicel Chiral OD-H and Daicel Chiral OD column in series (Hexane:i-propanol=99:1, 2 mL/min): t$_1$=19.78 min (minor), t$_2$=26.80 min (major) (see FIG. 27).

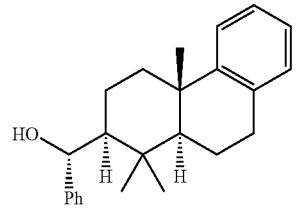

(R)-Phenyl((2S,4aS,10aS)-1,1,4a-trimethyl-1,2,3,4, 4a,9,10,10a-octahydrophenanthren-2-yl)methanol (75/75')

To a solution of ketone (72/72'/72'') (42 mg, 0.1 mmol, 1.0 eq.) in THF/MeOH (4 mL/2 mL) was added KOH aqueous solution (1 mL, 7.5 M). The reaction was allowed to stir at room temperature for 3 days. The reaction was quenched by adding 10 mL water. The mixture was extracted with CH$_2$Cl$_2$ (2×20 mL) and combined organic layer was washed with water (10 mL) and brine (10 mL). The organic layer was dried over anhydrous Na$_2$SO$_4$ and concentrated in vacuo. The residual crude product was purified by flash column chromatography to afford the alcohol as a white solid in 77% yield.

R$_f$: 0.36 (Hexane:Ethyl Acetate=4:1)

Ratio: 83:17. Ratio was determined by $^1$H NMR.

Major Isomer:

$^1$H NMR (400 MHz, CDCl$_3$): 7.01-7.38 (m, 9H), 5.21 (d, J=3.87 Hz, 1H), 2.97 (ddd, J=17.42, 6.62, 1.74 Hz, 1H), 2.83 (ddd, J=17.42, 11.50, 6.96 Hz, 1H), 2.30 (dt, J=12.54, 3.14 Hz, 1H), 2.01-1.91 (m, 1H), 1.87 (dd, J=13.45, 2.94 Hz. 1H), 1.84-1.70 (m, 2H), 1.66-1.58 (m, 1H), 1.43-1.26 (m, 2H), 1.25 (s, 3H), 1.24 (s, 3H), 1.11 (s, 3H)

$^{13}$C NMR (100 MHz, CDCl$_3$): 149.69, 146.07, 135.01, 128.85, 128.09, 126.58, 125.65, 125.35, 125.20, 124.53, 72.10, 55.55, 51.95, 38.47, 38.00, 37.32, 30.98, 30.09, 24.88, 19.43, 18.70, 16.19

HRMS (EI): m/z calculated for C$_{24}$H$_{30}$O [M]$^+$: 334.2297. Found: 334.2293.

FTIR (KBr): ν 3342, 2966, 2914, 1487, 1448, 1377, 1215, 1051, 756, 700 cm$^{-1}$

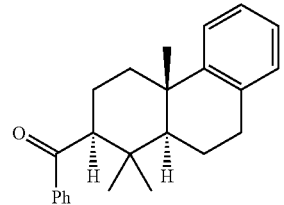

Phenyl((2S,4aS,10aS)-1,1,4a-trimethyl-1,2,3,4,4a,9, 10,10a-octahydrophenanthren-2-yl)methanone (76)

To an oven-dried 25 mL round-bottom flask equipped with a magnetic stirring bar was added PCC (0.129 g, 0.6 mmol, 3.0 eq.), 4 Å MS (0.3 g, oven-dried 48 hours), silica gel (0.3 g, oven-dried 48 hours) and CH$_2$Cl$_2$ (5 mL). The mixture was allowed to cool to 0° C. and alcohol 75/75' (67 mg, 0.2 mmol, 1.0 eq.) in CH$_2$Cl$_2$ (1 mL) was added dropwise. The reaction was gradually warmed up to room temperature and was allowed to stir for another 12 hours. The mixture was filtered through a pad of silica gel and flushed with 100 mL CH$_2$Cl$_2$. The solution was concentrated in vacuo. The residual crude product was purified by flash column chromatography to afford the ketone as a colourless solid in 93% yield, 52% ee.

R$_f$: 0.70 (Hexane:Ethyl acetate=4:1)

$^1$H NMR (300 MHz, CDCl$_3$): 8.0-7.97 (m, 1H), 7.54-7.45 (m, 2H), 7.27-7.09 (m, 6H), 3.42 (dd, J=12.56, 2.45 Hz, 1H), 2.99 (dd, J=17.17, 6.11 Hz, 1H), 2.88 (ddd, J=17.50, 11.07, 7.01 Hz, 1H), 2.45 (dt, J=13.04, 2.97 Hz, 1H), 2.40-2.15 (m, 1H), 1.93 (dd, J=13.71, 6.27 Hz, 1H), 1.92-1.50 (m, 4H), 1.29 (s, 3H), 1.06 (s, 3H), 0.95 (s, 3H)

$^{13}$C NMR (75 MHz, CDCl$_3$): 204.37, 149.49, 139.11, 134.96, 132.72, 129.00, 128.58, 128.22, 125.85, 125.43, 124.56, 54.38, 52.24, 38.59, 38.06, 37.04, 31.42, 30.78, 25.21, 23.30, 18.58, 18.25

HRMS (EI): m/z calculated for C$_{24}$H$_{28}$O [M]$^+$: 332.2140. Found: 332.2134.

FTIR (KBr): ν 3070.68, 2868.15, 1670.36, 1653.00, 1629.85, 1377.17, 1288.45, 1120.64, 1001.06, 873.75, 759.95, 723.31 cm$^{-1}$

The enantiomeric excess was determined by HPLC analysis employing Daicel Chiral AD and Daicel Chiral OJ column in series (Hexane:i-propanol=99.2:0.8, 1 mL/min): t$_1$=16.84 min (minor), t$_2$=21.88 min (major) (see FIG. 28)

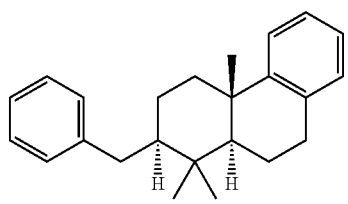

74

(2R,4aS,10aS)-2-Benzyl-1,1,4a-trimethyl-1,2,3,4,4a, 9,10,10a-octahydrophenanthrene (74)

To a hydrogenator flask was added 2j/2j'2j" (42 mg, 0.1 mmol, 1.0 eq.), Pd (11 mg, 10%, on activated carbon, 0.01 mmol, 0.1 eq.) and EtOH 10 mL. The flask was connected to hydrogen tank and hydrogen gas pressure inside the flask was maintained at 60 p.s.i. The mixture was allowed to shake for four days. The mixture was then filtered through a pad of Celite® and flushed with 100 mL Et$_2$O. The solution was concentrated in vacuo. The residual crude product was purified by flash column chromatography to afford the alkene as a colourless solid in 70% yield.

R$_f$: 0.90 (Hexane:Ethyl acetate=4:1)

$^1$H NMR (500 MHz, CDCl$_3$): 7.40-7.05 (m, 9H), 3.05 (dd, J=1.69 Hz, 1H), 3.00 (ddd, J=17.40, 6.46, 1.33 Hz, 1H), 2.91 (ddd, J=18.07, 11.60, 6.96 Hz, 1H), 2.24 (dt, J=13.09, 3.15 Hz, 1H), 2.16 (dd, J=13.33, 11.23 Hz, 1H), 2.00 (ddt, J=13.56, 6.78, 1.87 Hz, 1H), 1.85-1.70 (m, 1H), 1.63-1.55 (m, 1H), 1.50-1.27 (m, 4H), 1.24 (s, 3H), 1.20 (s, 3H), 0.94 (s, 3H)

$^{13}$C NMR (125 MHz, CDCl$_3$): 149.84, 142.47, 135.09, 129.20, 128.85, 128.14, 125.63, 125.53, 125.15, 124.51, 51.74, 50.23, 38.55, 37.94, 37.33, 36.92, 30.99, 29.17, 24.85, 23.86, 19.55, 17.12.

HRMS (EI): m/z calculated for C$_{24}$H$_{30}$ [M]$^+$: 318.2348. Found: 318.2339.

FTIR (KBr): ν 2964, 2924, 1490, 1475, 1448, 1375, 1041, 758, 734, 721, 698 cm$^{-1}$

Example 6

Utilisation of the Method of the Present Invention in Natural Substance Synthesis Reference is made to FIG. 9, which depicts reaction scheme of the present example. The reaction conditions used generally correspond to those already described above.

(4S,6S)-4,6-Dimethyl-2-phenyl-1,3-dioxane (see above, 0.3 mmol, 2.0 eq.) was added to a solution of (E)-9-(3-bromophenyl)-2,6-dimethyl-2,6-nonadienyl]-1-oxy-(tert.-butyl)diphenyl-silane (compound 41, 0.1 mmol, 1.0 eq.) in dichloromethane (2 mL) at room temperature. The solution was cooled to −78° C. prior to addition of SnCl$_4$ (1.0 M in dichloromethane, 0.2 mL, 2.0 eq.). The reaction was allowed to stir at −78° C. for 2 hrs before quenching with saturated NaHCO$_3$ aqueous solution (5 mL). The mixture was gradually warmed up to room temperature and was allowed to stir for another 1 hour. The aqueous layer was extracted with dichloromethane (3×20 mL), and the combined organic layer was washed with water (20 mL), brine (20 mL) and dried over anhydrous Na$_2$SO$_4$, filtered and concentrated in vacuo. (2R,4R)-4-((R)-((1R,2S,4aS,10aR)-7-bromo-1,4-a-dimethyl-1-(tert.-butyl)diphenyl-siloxymethyl -1,2,3,4,4a,9,10,10a-octahydro-phenanthren-2-yl)(phenyl)methoxy)-propan-3-ol (compound 42) was isolated in a yield of 46% by flash column chromatography.

Pyridinium chlorochromate (0.324 g, 1.5 mmol, 3.0 eq.), 4 Å MS (1.0 g, oven-dried 48 hours), silica gel (1 g, oven-dried 48 hours) and dichloromethane (8 mL) were added to an oven-dried 25 mL round-bottom flask equipped with a magnetic stirring bar. The mixture was allowed to cool to 0° C. and alcohol 42 (0.21 g, 0.5 mmol, 1.0 eq.) in dichloromethane (2 mL) was added slowly. The reaction mixture was gradually warmed up to room temperature and was allowed to stir for another 4 hours. The mixture was filtered through a pad of silica gel and was flushed with 200 mL dichloromethane. The solution was concentrated in vacuo. The residual product was purified by flash column chromatography to afford (2R,4R)-4-((R)-((1R,2S,4aS,10aR)-7-bromo-1,4a-dimethyl-1-(tert.-butyl)diphenyl-siloxymethyl-1,2,3,4,4a,9,10,10a-octahydro-phenanthren-2-yl)(phenyl)methoxy)propan-3-al 54 in 92%.

To a solution of ketone 72 (42 mg, 0.1 mmol, 1.0 eq.) in THF/MeOH (4 mL/2 mL) was added KOH aqueous solution (1 mL, 7.5 M). The reaction was allowed to stir at room temperature for 2 days. The reaction was quenched by adding 10 mL water. The mixture was extracted with dichloromethane (2×20 mL) and the combined organic layer was washed with water (10 mL) and brine (10 mL). The organic layer was dried over anhydrous Na$_2$SO$_4$ and concentrated in vacuo. The residual crude product was purified by flash column chromatography to afford phenyl((1R,2S,4aS,10aR)-1,4a-dimethyl-1-(tert.-butyl)diphenyl-silyl-methoxy-1,2,3,4,4a,9,10,10a-octahydro-phenanthren-2-yl)methanol 55. The same sequence of reactions as described in this and the previous paragraph were used to convert compound (38) ((E,E)-6,10,14-trimethyl-5,9,13-pentadecatrien-1-yne) to the (7-dodecahydro-3a,6,6,9a-tetramethyl-3-chloromethyliden-benzindenyl)-α-benzyl alcohol isomer (45) and compound (39) to compound (45) (cf. FIG. 8).

What is claimed is:

1. A cyclisation process for forming a multiple ring compound, the process comprising reacting an isoprenoid compound with an acetal initiator under conditions sufficient to form the multiple ring compound, wherein the cyclisation process comprises an intramolecular cyclisation reaction of the isoprenoid compound, and wherein the acetal initiator is an oxygen acetal, a thioacetal or a selenoacetal having one of the following general formulas (I) or (II):

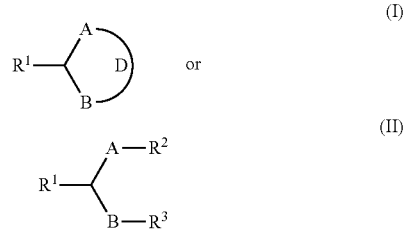

wherein:
A and B are independently heteroatoms selected from the group consisting of O, S and Se;
$R^1$ is selected from the group consisting of aliphatic, cycloaliphatic, aromatic, arylaliphatic, and arylcycloaliphatic groups, comprising from 0 to about 3 heteroatoms selected from the group consisting of N, O, S, Se and Si;
D is an aliphatic, cycloaliphatic or arylaliphatic bridge containing from 1 to about 12 carbon atoms, completing a non-aromatic ring that includes from 0 to about 2 heteroatoms; and
$R^2$ and $R^3$ are independently selected from the group consisting of aliphatic, cycloaliphatic, aromatic, arylaliphatic, and arylcycloaliphatic groups, comprising from 0 to about 3 heteroatoms selected from the group N, O, S, Se and Si, and wherein one of $R^2$ and $R^3$ may be H.

2. The cyclisation process of claim 1, comprising contacting said isoprenoid compound with said acetal initiator in the presence of a catalyst.

3. The cyclisation process of claim 2, wherein said catalyst is an acid.

4. The cyclisation process of claim 3, wherein said catalyst is a Lewis acid or a Brønsted acid.

5. The cyclisation process of claim 4, wherein the Lewis acid is derived from an element of Group IIIA of the Periodic Table of Elements, titanium, tin, antimony, tantalum, rhenium, iron or zinc.

6. The cyclisation process of claim 4, wherein said Lewis acid is selected from the group consisting of $AgBF_4$, $Ag(OTf)$, $AlCl_3$, $AlBr_3$, $Al(OTf)_3$, $BCl_3$, $BBr_3$, $BF_3$, $Ce(OTf)_4$, $Cu(OTf)_2$, $InCl_3$, $InBr_3$, $In(OTf)_3$, $La(OTf)_3$, $Sc(OTf)_3$, $Sm(OTf)_3$, $SnBr_4$, $Sn(OTf)_4$, $SnCl_4$, $Sn(OTf)_2$, $TiBr_4$, $TiCl_4$, $Ti(OTf)_4$, and $Zn(OTf)_2$.

7. The cyclisation process of claim 4, wherein said Brønsted acid is $CF_3SO_3H$, $FSO_3H$, $MeSO_3H$, $CCl_3SO_3H$, HBr, HCl, $CF_3CO_2H$ or $(CF_3SO_2)_2NH$.

8. The cyclisation process of claim 1, wherein reacting the isoprenoid compound with the acetal initiator comprises allowing the acetal initiator to form a covalent bond with the isoprenoid compound.

9. The cyclisation process of claim 8, wherein the acetal initiator is allowed to add to the terminal double bond of said isoprenoid compound.

10. The cyclisation process of claim 8, wherein said acetal initiator adds to the third carbon atom ($C_3$) of an isoprenoid unit of said isoprenoid compound.

11. The cyclisation process of claim 1, wherein the acetal initiator has one of the following general formulas (III), (IV) or (V):

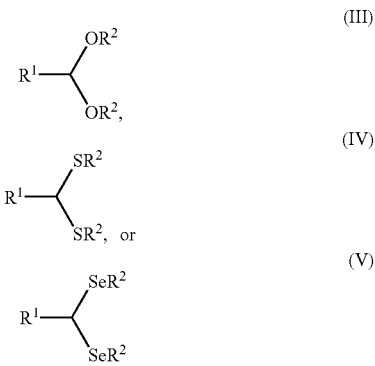

wherein $R^1$ and $R^2$ are independently selected from the group consisting of aliphatic, cycloaliphatic, aromatic, arylaliphatic, and arylcycloaliphatic groups, comprising from 0 to about 3 heteroatoms selected from the group consisting of N, O, S, Se and Si.

12. The cyclisation process of claim 1, wherein the isoprenoid compound comprises a number of terpenoid units selected in the range of between about one and about six.

13. The cyclisation process of claim 1, wherein the cyclisation process results in the formation of a multiple ring compound that is a cyclic terpenoid compound.

14. The cyclisation process of claim 13, wherein the cyclic terpenoid compound has a bicyclic, a tricyclic, a tetracyclic, or a pentacyclic ring system.

15. The cyclisation process of claim 12, wherein the isoprenoid compound has the following general formula (VI):

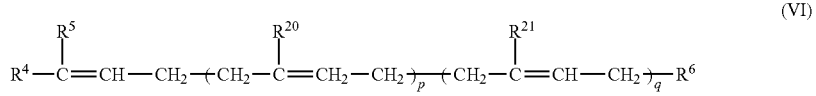

wherein $R^4$ and $R^5$ are independently an aliphatic, cycloaliphatic, aromatic, arylaliphatic, or arylcycloaliphatic moiety;
$R^{20}$ and $R^{21}$ are independently selected from the group consisting of an aliphatic, cycloaliphatic, aromatic, arylaliphatic or arylcycloaliphatic moiety, halogen, a hydroxyl group, a thiol group, a seleno group, a carboxyl group, an amino group, an imino group, an amido group, an imido group, an azido group, a diazo group, a cyano group, an isocyano group, a nitro group, a nitroso group, a sulfo group, a sulfido group, a sulfonyl group and a silyl group;
$R^6$ is a terminating moiety; and
p and q are an independently selected from an integer between 0 and about 4.

16. The cyclisation process of claim 15, wherein the isoprenoid compound has the following general formula (VII):

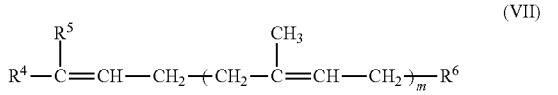

(VII)

wherein $R^4$ and $R^5$ are independently an aliphatic, cycloaliphatic, aromatic, arylaliphatic, or arylcycloaliphatic moiety;
$R^6$ is a terminating moiety; and
m is an integer between 0 and about 5.

17. The cyclisation process of claim 15, wherein $R^6$ is selected from the group consisting of H, an aliphatic, cycloaliphatic, aromatic, arylaliphatic or arylcycloaliphatic moiety, halogen, a hydroxyl group, a thiol group, a seleno group, a carboxyl group, an amino group, an imino group, an amido group, an imido group, an azido group, a diazo group, a cyano group, an isocyano group, a nitro group, a nitroso group, a sulfo group, a sulfido group, a sulfonyl-group and a silyl group.

18. The cyclisation process of claim 12, wherein the isoprenoid compound has the following general formula (VIII):

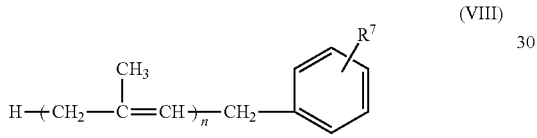

(VIII)

wherein n is 1 or 2 and $R^7$ is selected from the group consisting of H, aliphatic, cycloaliphatic, aromatic, arylaliphatic, and arylcycloaliphatic groups, comprising from 0 to about 3 heteroatoms selected from the group consisting of N, O, S, Se and Si.

19. The cyclisation process of claim 13, wherein the acetal initiator has general formula (I) or (II), and wherein the cyclisation process results in the formation of a multiple ring compound having the following general formula (XII):

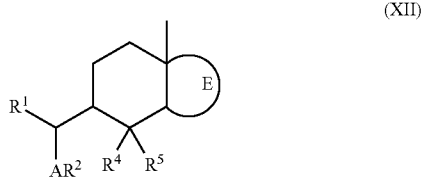

(XII)

wherein E is an aliphatic, cycloaliphatic or arylaliphatic bridge containing from about 3 to about 8 carbon atoms, completing a non-aromatic ring comprising from 0 to about 2 heteroatoms;
A is selected from the group consisting of O, S and Se; and
$R^1$, $R^2$, $R^4$ and $R^5$ are independently selected from the group consisting of aliphatic, cycloaliphatic, aromatic, arylaliphatic, and arylcycloaliphatic groups, comprising from 0 to about 3 heteroatoms selected from the group consisting of N, O, S, Se and Si.

20. The cyclisation process of claim 18, wherein the isoprenoid compound has general formula (VIII), wherein n=2 and $R^7$ is selected from the group consisting of H, aliphatic, cycloaliphatic, aromatic, arylaliphatic, and arylcycloaliphatic groups, comprising from 0 to about 3 heteroatoms selected from the group consisting of N, O, S, Se and Si, and wherein the multiple ring compound has the following general formula (XIII):

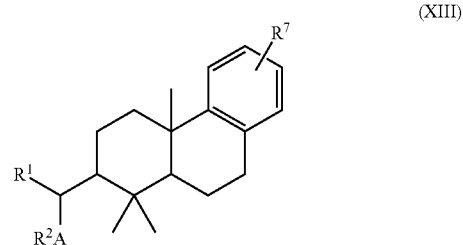

(XIII)

wherein A is selected from the group consisting of O, S and Se, and
$R^1$, $R^2$ and $R^7$ are independently selected from the group consisting of aliphatic, cycloaliphatic, aromatic, arylaliphatic, and arylcycloaliphatic groups, comprising from 0 to about 3 heteroatoms selected from the group consisting of N, O, S, Se and Si, and wherein $R^7$ may be H.

21. The cyclisation process of claim 2, wherein contacting said isoprenoid compound with said catalyst and said initiator is carried out at or below room temperature.

22. The cyclisation process of claim 1, wherein the temperature is selected in the range between about −78° C. and about 25° C.

23. The cyclisation process of claim 22, wherein the temperature is selected in the range between about −78° C. and about 0° C.

24. The cyclisation process of claim 1, wherein contacting said isoprenoid compound with said catalyst and said initiator is performed in a nonpolar solvent.

25. The cyclisation process of claim 24, wherein the nonpolar solvent is hexane, heptane, carbon disulfide, benzene, toluene, p-xylene, pyridine, aniline, dichloromethane, dichloroethane, chloroform, carbon tetrachloride, tetrahydrofuran, methyl ethyl ketone, methyl isobutyl ketone, acetone, cyclohexanone, ethyl acetate, isobutyl isobutyrate, dioxane, diethyl ether, diisopropylether, ethylene glycol monobutyl ether, or tetrahydrofuran.

26. The cyclisation process of claim 2, comprising using a molar ratio of isoprenoid compound to acetal selected in the range from about 1:10 to about 10:1.

27. The cyclisation process of claim 26, wherein said molar ratio is selected in the range from about 1:3 to about 3:1.

28. The cyclisation process of claim 1, wherein the initiator comprises at least two chiral centers.

29. The cyclisation process of claim 28, wherein the acetal initiator has one of the following general formulas (IX), (X) or (XI):

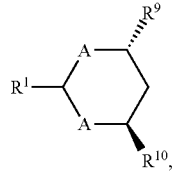
(IX)

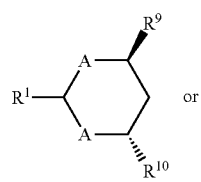
(X) or

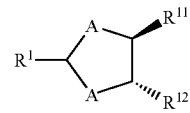
(XI)

wherein $R^9$, $R^{10}$, $R^{11}$ and $R^{12}$ are independently selected from the group consisting of H, aliphatic, cycloaliphatic, aromatic, arylaliphatic, and arylcycloaliphatic groups, comprising from 0 to about 3 heteroatoms selected from the group consisting of N, O, S, Se and Si.

30. The cyclisation process of claim 29, wherein $R^1$ is phenyl or:

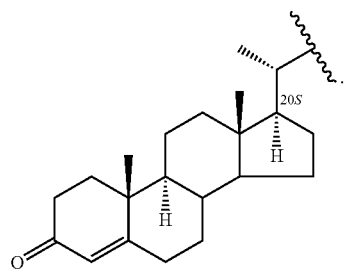

31. The cyclisation process of claim 28, wherein the intramolecular cyclisation reaction is an enantioselective cyclisation.

32. The cyclisation process of claim 28, wherein the acetal initiator induces enantioselectivity.

33. The cyclisation process of claim 28, wherein the acetal initiator has formula (IX), (X) or (XI), and wherein only $R^1$ of the acetal initiator induces enantioselectivity.

34. The cyclisation process of claim 33, wherein $R^1$ is:

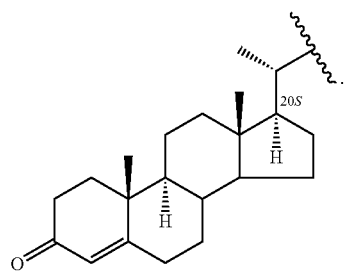

* * * * *

UNITED STATES PATENT AND TRADEMARK OFFICE
CERTIFICATE OF CORRECTION

PATENT NO.          : 8,227,645 B2
APPLICATION NO.     : 12/280158
DATED               : July 24, 2012
INVENTOR(S)         : Teck Peng Loh et al.

It is certified that error appears in the above-identified patent and that said Letters Patent is hereby corrected as shown below:

In the Claims

Column 68, Line 21:
"33. The cyclisation process of claim 28, wherein the acetal" should read, --33. The cyclisation process of claim 32, wherein the acetal--.

Signed and Sealed this
Twenty-fifth Day of June, 2013

Teresa Stanek Rea
*Acting Director of the United States Patent and Trademark Office*